US010934553B2

(12) United States Patent
Roemer et al.

(10) Patent No.: US 10,934,553 B2
(45) Date of Patent: Mar. 2, 2021

(54) AGROBACTERIUM FOR TRANSIENT TRANSFECTION OF WHOLE PLANTS

(71) Applicant: Nomad Bioscience GmbH, Munich (DE)

(72) Inventors: Patrick Roemer, Zoerbig (DE); Luisa Bortesi, Aachen (DE); Doreen Tiede, Kothen (DE); Anatoli Giritch, Halle (DE); Yuri Gleba, Berlin (DE)

(73) Assignee: Nomad Bioscience GmbH, Munich (DE)

( * ) Notice: Subject to any disclaimer, the term of this patent is extended or adjusted under 35 U.S.C. 154(b) by 0 days.

(21) Appl. No.: 16/519,323

(22) Filed: Jul. 23, 2019

(65) Prior Publication Data

US 2019/0338297 A1 Nov. 7, 2019

Related U.S. Application Data

(63) Continuation of application No. 14/386,441, filed as application No. PCT/EP2013/000994 on Apr. 3, 2013, now abandoned.

(30) Foreign Application Priority Data

Apr. 3, 2012 (EP) .................................... 12002402

(51) Int. Cl.
*C12N 15/82* (2006.01)

(52) U.S. Cl.
CPC ................................ *C12N 15/8205* (2013.01)

(58) Field of Classification Search
CPC ................................................. C12N 15/8205
See application file for complete search history.

(56) References Cited

U.S. PATENT DOCUMENTS

| | | | | |
|---|---|---|---|---|
| 5,929,306 A * | 7/1999 | Torisky | .............. | C12N 15/8205 435/252.2 |
| 2007/0006351 A1* | 1/2007 | Torisky | .............. | C12N 15/8205 800/320 |
| 2010/0319089 A1* | 12/2010 | Azhakanandam | .......................... | C12N 15/8241 800/294 |

OTHER PUBLICATIONS

Chandrasekaran et al (Isolation and Characterization of Avirulent and Virulent Strains of Agrobacterium tumefaciens from Rose Crown Gall in Selected Regions of South Korea. Plants, 8, 452: 1-12, 2019) (Year: 2019).*

Akcay et al (Agrobacterium tumefaciens-mediated genetic transformation of a recalcitrant grain legume, lentil (*Lens culinaris* Medik) . Plant Cell Rep 28:407-417, 2009) (Year: 2009).*

Fits et al (The ternary transformation system: constitutive virG on a compatible plasmid dramatically increases Agrobacterium-mediated plant transformation. Plant Molecular Biology 43: 495-502, 2000) (Year: 2000).*

Pao et al (Response regulators of bacterial signal transduction systems: selective domain shuffling during evolution. J Mol Evol. 40(2):136-54, 1995) (Year: 1995).*

Radchuk et al, Institute of Cell Biology and Genetic Engineering, National Academy of Sciences of Ukraine, Kiev, Ukraine. 2000 in Russian. (Year: 2000).*

Sheludko YV. Institute of Cell Biology and Genetic Engineering NAS of Ukraine, Zabolotnogo Street 148, Kiev 03680, Ukraine. 2008 (Year: 2008).*

Ackay, U., et al., "*Agrobacterium tumefaciens*-mediated genetic transformation of a recalcitrant grain legume, lentil (*Lens culinaris* Medlik)," *Plant Cell Rep*, 2009, vol. 28(13), pp. 407-417.

Giritch, A., et anon, "Transient Expression Technologies as an Alternative to Genetically Modified Plants," Nomad Bioscience GmbH, retrieved from the Internet: URL:http://conference.icbge.org.ua/en/abstracts/30-transient-expression-technologies-as-an-alternative-to-genetically-modified-plants, 2011, retrieved on May 23, 2012, abstract only.

Hood, E., et al., "The Hyperviralence of *Agrobacterium tumefaciens* A281 Is Encoded in a Region of pTiBo542 Outside of T-DNA," *Journal of Bacteriology*, 1986, vol. 168(3), pp. 1291-1301.

Jin, S., et al., "Characterization of a virG mutation that confers constitutive virulence gene expression in*Agrobacterium," Molecular Microbiology*, 1993, vol. 7(4), pp. 555-562.

Joh, L., et anon, "Perspective Agroinfiltration of plant tissues for production of high-value recombinant proteins: an alternative to production in transgenic crops," *Journal of the Science of Food and Agriculture*, 2006, vol. 86(13), pp. 2002-2004.

Kovács, L., et anon, "The Chromosomal Background of*Agrobacterium tumefaciens* Chry5 Conditions High Virulence on Soybean," *MPMI*, 1993, vol. 6(5), pp. 601-608.

Palanichelvam, K., et al., "A Second T-Region of the Soybean-Supervirulent Chrysopine-Type Ti Plasmid pTiChry5, and Construction of a Fully Disarmed vir Helper Plasmid," *MPMI*, 2000, vol. 13(10), pp. 1081-1091.

Sheludko, Yuriv V., "*Agrobacterium*-Mediated Transient Expression as an Approach to Production of Recombinant Proteins in Plants," *Recent Patents on Biotechnology*, 2008, vol. 2(3), pp. 198-208.

Torisky, R., et al., "Development of a binary vector system for plant transformation based on the supervirulent*Agrobacterium tumefaciens* strain Chry5," *Plant Cell Reports*, 1997, vol. 17(2), pp. 102-108.

(Continued)

*Primary Examiner* — Ashley K Buran
*Assistant Examiner* — Wayne Zhong
(74) *Attorney, Agent, or Firm* — Williams Mullen; David M. Saravitz

(57) ABSTRACT

A process of transiently transfecting a plant or leaves on a plant, comprising contacting said plant or said leaves with a suspension comprising *Agrobacterium* cells of strain CryX or a derivative strain of strain CryX, wherein said derivative strain has the chromosomal background of strain CryX or said derivative strain contains the vir plasmid of strain CryX or a derivative of said vir plasmid.

7 Claims, 13 Drawing Sheets

Specification includes a Sequence Listing.

(56) References Cited

OTHER PUBLICATIONS

Radchuk et al, Institute of Cell Biology and Genetic Engineering NAS of Ukraine, Zabolotnogo Street 148, Kiev 03680, Ukraine. Production of transgenic rape plants (*Brassica napus* L.) using *Agrobacterium tumefaciens*. Genetika. Jul; 36(7):932-41, 2000.

Fits et al (The ternary transformation system: constitutive virG on a compatible plasmid dramatically increases Agrobacterium-mediated plant transformation. Plant Molecular Biology 43: 495-502, 2000).

* cited by examiner $10^{-3}$ $10^{-4}$ $10^{-5}$ 4 dpi $10^{-5}$ 5 dpi

SEQUENCE LISTING

<160> NUMBER OF SEQ ID NOS: 8

<210> SEQ ID NO 1
<211> LENGTH: 241
<212> TYPE: PRT
<213> ORGANISM: Agrobacterium tumefaciens

<400> SEQUENCE: 1

```
Leu Lys His Val Leu Leu Val Asp Asp Asp Val Ala Met Arg His Leu
1               5                   10                  15

Ile Ile Glu Tyr Leu Thr Ile His Ala Phe Lys Val Thr Ala Val Ala
            20                  25                  30

Asp Ser Thr Gln Phe Thr Arg Val Leu Ser Ser Ala Thr Val Asp Val
        35                  40                  45

Val Val Val Asp Leu Asn Leu Gly Arg Glu Asp Gly Leu Glu Ile Val
    50                  55                  60

Arg Asn Leu Ala Ala Lys Ser Asp Ile Pro Ile Ile Ile Ile Ser Gly
65                  70                  75                  80

Asp Arg Leu Glu Glu Thr Asp Lys Val Val Ala Leu Glu Leu Gly Ala
                85                  90                  95

Ser Asp Phe Ile Ala Lys Pro Phe Ser Ile Arg Glu Phe Leu Ala Arg
            100                 105                 110

Ile Arg Val Ala Leu Arg Val Arg Pro Asn Val Val Arg Ser Lys Asp
        115                 120                 125

Arg Arg Ser Phe Cys Phe Thr Asp Trp Thr Leu Asn Leu Arg Gln Arg
    130                 135                 140

Arg Leu Met Ser Glu Ala Gly Gly Glu Val Lys Leu Thr Ala Gly Glu
145                 150                 155                 160

Phe Asn Leu Leu Leu Ala Phe Leu Glu Lys Pro Arg Asp Val Leu Ser
                165                 170                 175

Arg Glu Gln Leu Leu Ile Ala Ser Arg Val Arg Asp Glu Glu Val Tyr
            180                 185                 190

Asp Arg Ser Ile Asp Val Leu Ile Leu Arg Leu Arg Arg Lys Leu Glu
        195                 200                 205

Ala Asp Pro Ser Ser Pro Gln Leu Ile Lys Thr Ala Arg Gly Ala Gly
    210                 215                 220

Tyr Phe Phe Asp Ala Asp Val Gln Val Ser His Gly Gly Thr Met Ala
225                 230                 235                 240

Ala
```

<210> SEQ ID NO 2
<211> LENGTH: 10393
<212> TYPE: DNA
<213> ORGANISM: Artificial Sequence
<220> FEATURE:
<223> OTHER INFORMATION: T-DNA region sequences of pNMD560

<400> SEQUENCE: 2

```
cctgtggttg gcacatacaa atggacgaac ggataaacct tttcacgccc ttttaaatat      60

ccgattattc taataaacgc tcttttctct taggtttacc cgccaatata tcctgtcaaa     120

cactgatagt ttaaactgaa ggcgggaaac gacaatctga tctaagctag cttggaattg     180

gtaccacgcg tttcgacaaa atttagaacg aacttaatta tgatctcaaa tacattgata     240

catatctcat ctagatctag gttatcatta tgtaagaaag ttttgacgaa tatggcacga     300

caaaatggct agactcgatg taattggtat ctcaactcaa cattatactt ataccaaaca     360
```

-continued

```
ttagttagac aaaatttaaa caactatttt ttatgtatgc aagagtcagc atatgtataa    420
ttgattcaga atcgttttga cgagttcgga tgtagtagta gccattattt aatgtacata    480
ctaatcgtga atagtgaata tgatgaaaca ttgtatctta ttgtataaat atccataaac    540
acatcatgaa agacactttc tttcacggtc tgaattaatt atgatacaat tctaatagaa    600
aacgaattaa attacgttga attgtatgaa atctaattga acaagccaac cacgacgacg    660
actaacgttg cctggattga ctcggtttaa gttaaccact aaaaaaacgg agctgtcatg    720
taacacgcgg atcgagcagg tcacagtcat gaagccatca aagcaaaaga actaatccaa    780
gggctgagat gattaattag tttaaaaatt agttaacacg agggaaaagg ctgtctgaca    840
gccaggtcac gttatcttta cctgtggtcg aaatgattcg tgtctgtcga ttttaattat    900
ttttttgaaa ggccgaaaat aaagttgtaa gagataaacc cgcctatata aattcatata    960
ttttcctctc cgctttgaag ttttagtttt attgcaacaa caacaacaaa ttacaataac   1020
aacaaacaaa atacaaacaa caacaacatg gcacaatttc aacaaacaat tgacatgcaa   1080
actctccaag ccgctgcggg acgcaacagc ttggtgaatg atttggcatc tcgtcgcgtt   1140
tacgataatg cagtcgagga gctgaatgct cgttccagac gtcccaaggt aataggaact   1200
ttctggatct actttatttg ctggatctcg atcttgtttt ctcaatttcc ttgagatctg   1260
gaattcgttt aatttggatc tgtgaacctc cactaaatct tttggtttta ctagaatcga   1320
tctaagttga ccgatcagtt agctcgatta tagctaccag aatttggctt gaccttgatg   1380
gagagatcca tgttcatgtt acctgggaaa tgatttgtat atgtgaattg aaatctgaac   1440
tgttgaagtt agattgaatc tgaacactgt caatgttaga ttgaatctga acactgttta   1500
aggttagatg aagtttgtgt atagattctt cgaaacttta ggatttgtag tgtcgtacgt   1560
tgaacagaaa gctatttctg attcaatcag ggtttatttg actgtattga actctttttg   1620
tgtgtttgca ggtccacttc tccaaggcag tgtctacgga acagaccctg attgcaacaa   1680
acgcatatcc ggagttcgag atttccttta ctcatacgca atccgctgtg cactccttgg   1740
ccggaggcct tcggtcactt gagttggagt atctcatgat gcaagttccg ttcggttctc   1800
tgacgtacga catcggcggt aacttttccg cgcacctttt caaagggcgc gattacgttc   1860
actgctgcat gcctaatctg gatgtacgtg acattgctcg ccatgaagga cacaaggaag   1920
ctatttacag ttatgtgaat cgtttgaaaa ggcagcagcg tcctgtgcct gaataccaga   1980
gggcagcttt caacaactac gctgagaacc cgcacttcgt ccattgcgac aaacctttcc   2040
aacagtgtga attgacgaca gcgtatggca ctgacaccta cgctgtagct ctccatagca   2100
tttatgatat ccctgttgag gagttcggtt ctgcgctact caggaagaat gtgaaaactt   2160
gtttcgcggc ctttcatttc catgagaata tgcttctaga ttgtgataca gtcacactcg   2220
atgagattgg agctacgttc cagaaatcag gtaacattcc ttagttacct ttcttttctt   2280
tttccatcat aagtttatag attgtacatg ctttgagatt tttctttgca aacaatctca   2340
ggtgataacc tgagcttctt cttccataat gagagcactc tcaattacac ccacagcttc   2400
agcaacatca tcaagtacgt gtgcaagacg ttcttccctg ctagtcaacg cttcgtgtac   2460
cacaaggagt tcctggtcac tagagtcaac acttggtact gcaagttcac gagagtggat   2520
acgttcactc tgttccgtgg tgtgtaccac aacaatgtgg attgcgaaga gttttacaag   2580
gctatggacg atgcgtggca ctacaaaaag acgttagcaa tgcttaatgc cgagaggacc   2640
atcttcaagg ataacgctgc gttaaacttc tggttcccga aggtgctctt gaaattggaa   2700
gtcttctttt gttgtctaaa cctatcaatt tctttgcgga aatttatttg aagctgtaga   2760
```

-continued

```
gttaaaattg agtcttttaa acttttgtag gtgagagaca tggttatcgt ccctctcttt   2820
gacgcttcta tcacaactgg taggatgtct aggagagagg ttatggtgaa caaggacttc   2880
gtctacacgg tcctaaatca catcaagacc tatcaagcta aggcactgac gtacgcaaac   2940
gtgctgagct tcgtggagtc tattaggtct agagtgataa ttaacggtgt cactgccagg   3000
taagttgtta cttatgattg ttttcctctc tgctacatgt attttgttgt tcatttctgt   3060
aagatataag aattgagttt tcctctgatg atattattag gtctgaatgg gacacagaca   3120
aggcaattct aggtccatta gcaatgacat tcttcctgat cacgaagctg ggtcatgtgc   3180
aagatgaaat aatcctgaaa aagttccaga agttcgacag aaccaccaat gagctgattt   3240
ggacaagtct ctgcgatgcc ctgatggggg ttattccctc ggtcaaggag acgcttgtgc   3300
gcggtggttt tgtgaaagta gcagaacaag ccttagagat caaggttagt atcatatgaa   3360
gaaataccta gtttcagttg atgaatgcta ttttctgacc tcagttgttc tcttttgaga   3420
attatttctt ttctaatttg cctgattttt ctattaattc attaggttcc cgagctatac   3480
tgtaccttcg ccgaccgatt ggtactacag tacaagaagg cggaggagtt ccaatcgtgt   3540
gatctttcca aacctctaga agagtcagag aagtactaca acgcattatc cgagctatca   3600
gtgcttgaga atctcgactc ttttgactta gaggcgttta agactttatg tcagcagaag   3660
aatgtggacc cggatatggc agcaaaggta aatcctggtc cacactttta cgataaaaac   3720
acaagatttt aaactatgaa ctgatcaata atcattccta aaagaccaca cttttgtttt   3780
gtttctaaag taatttttac tgttataaca ggtggtcgta gcaatcatga agtcagaatt   3840
gacgttgcct ttcaagaaac ctacagaaga ggaaatctcg gagtcgctaa aaccaggaga   3900
ggggtcgtgt gcagagcata aggaagtgtt gagcttacaa aatgatgctc cgttcccgtg   3960
tgtgaaaaat ctagttgaag gttccgtgcc ggcgtatgga atgtgtccta agggtggtgg   4020
tttcgacaaa ttggatgtgg acattgctga tttccatctc aagagtgtag atgcagttaa   4080
aaagggaact atgatgtctg cggtgtacac agggtctatc aaagttcaac aaatgaagaa   4140
ctacatagat tacttaagtg cgtcgctggc agctacagtc tcaaacctct gcaaggtaag   4200
aggtcaaaag gtttccgcaa tgatccctct tttttgttt ctctagtttc aagaatttgg   4260
gtatatgact aacttctgag tgttccttga tgcatatttg tgatgagaca aatgtttgtt   4320
ctatgtttta ggtgcttaga gatgttcacg gcgttgaccc agagtcacag gagaaatctg   4380
gagtgtggga tgttaggaga ggacgttggt tacttaaacc taatgcgaaa agtcacgcgt   4440
ggggtgtggc agaagacgcc aaccacaagt tggttattgt gttactcaac tgggatgacg   4500
gaaagccggt ttgtgatgag acatggttca gggtggcggt gtcaagcgat tccttgatat   4560
attcggatat gggaaaactt aagacgctca cgtcttgcag tccaaatggt gagccaccgg   4620
agcctaacgc caaagtaatt ttggtcgatg gtgttcccgg ttgtggaaaa acgaaggaga   4680
ttatcgaaaa ggtaagttct gcatttggtt atgctccttg cattttaggt gttcgtcgct   4740
cttccatttc catgaatagc taagattttt tttctctgca ttcattcttc ttgcctcagt   4800
tctaactgtt tgtggtattt ttgttttaat tattgctaca ggtaaacttc tctgaagact   4860
tgattttagt ccctgggaag gaagcttcta agatgatcat ccggagggcc aaccaagctg   4920
gtgtgataag agcggataag gacaatgtta gaacggtgga ttccttcttg atgcatcctt   4980
ctagaagggt gtttaagagg ttgtttatcg atgaaggact aatgctgcat acaggttgtg   5040
taaatttcct actgctgcta tctcaatgtg acgtcgcata tgtgtatggg gacacaaagc   5100
```

-continued aaattccgtt catttgcaga gtcgcgaact ttccgtatcc agcgcatttt gcaaaactcg 5160
tcgctgatga gaaggaagtc agaagagtta cgctcaggta aagcaactgt gttttaatca 5220
atttcttgtc aggatatatg gattataact taatttttga gaaatctgta gtatttggcg 5280
tgaaatgagt ttgctttttg gtttctcccg tgttataggt gcccggctga tgttacgtat 5340
ttccttaaca agaagtatga cggggcggtg atgtgtacca gcgcggtaga gagatccgtg 5400
aaggcagaag tggtgagagg aaagggtgca ttgaacccaa taaccttacc gttggagggt 5460 aaaatttga ccttcacaca agctgacaag ttcgagttac tggagaaggg ttacaaggta 5520
aagtttccaa ctttccttta ccatatcaaa ctaaagttcg aaacttttta tttgatcaac 5580
ttcaaggcca cccgatcttt ctattcctga ttaatttgtg atgaatccat attgactttt 5640
gatggttacg caggatgtga acactgtgca cgaggtgcaa ggggagacgt acgagaagac 5700
tgctattgtg cgcttgacat caactccgtt agagatcata tcgagtgcgt cacctcatgt 5760
tttggtggcg ctgacaagac acacaacgtg ttgtaaatat tacaccgttg tgttggaccc 5820
gatggtgaat gtgatttcag aaatggagaa gttgtccaat ttccttcttg acatgtatag 5880
agttgaagca ggtctgtctt tcctatttca tatgtttaat cctaggaatt tgatcaattg 5940
attgtatgta tgtcgatccc aagactttct tgttcactta tatcttaact ctctctttgc 6000
tgtttcttgc aggtgtccaa tagcaattac aaatcgatgc agtattcagg ggacagaact 6060
tgtttgttca gacgcccaag tcaggagatt ggcgagatat gcaattttac tatgacgctc 6120
ttcttcccgg aaacagtact attctcaatg aatttgatgc tgttacgatg aatttgaggg 6180
atatttcctt aaacgtcaaa gattgcagaa tcgacttctc caaatccgtg caacttccta 6240
aagaacaacc tattttcctc aagcctaaaa taagaactgc ggcagaaatg ccgagaactg 6300
caggtaaaat attggatgcc agacgatatt ctttcttttg atttgtaact ttttcctgtc 6360
aaggtcgata aattttattt tttttggtaa aaggtcgata attttttttt ggagccatta 6420
tgtaattttc ctaattaact gaaccaaaat tatacaaacc aggtttgctg gaaaatttgg 6480
ttgcaatgat caaaagaaac atgaatgcgc cggatttgac agggacaatt gacattgagg 6540
atactgcatc tctggtggtt gaaaagtttt gggattcgta tgttgacaag gaatttagtg 6600
gaacgaacga aatgaccatg acaagggaga gcttctccag gtaaggactt ctcatgaata 6660
ttagtggcag attagtgttg ttaaagtctt tggttagata atcgatgcct cctaattgtc 6720
catgttttac tggttttcta caattaaagg tggctttcga aacaagagtc atctacagtt 6780
ggtcagttag cggactttaa ctttgtggat ttgccggcag tagatgagta caagcatatg 6840
atcaagagtc aaccaaagca aaagttagac ttgagtattc aagacgaata tcctgcattg 6900
cagacgatag tctaccattc gaaaaagatc aatgcgattt tcggtccaat gttttcagaa 6960
cttacgagga tgttactcga aaggattgac tcttcgaagt ttctgttcta caccagaaag 7020
acacctgcac aaatagagga cttcttttct gacctagact caacccaggc gatggaaatt 7080
ctggaactcg acatttcgaa gtacgataag tcacaaaacg agttccattg tgctgtagag 7140
tacaagatct gggaaaagtt aggaattgat gagtggctag ctgaggtctg gaaacaaggt 7200
gagttcctaa gttccatttt tttgtaatcc ttcaatgtta ttttaacttt tcagatcaac 7260
atcaaaatta ggttcaattt tcatcaacca aataatattt ttcatgtata tataggtcac 7320
agaaaaacga ccttgaaaga ttatacggcc ggaatcaaaa catgtctttg gtatcaaagg 7380
aaaagtggtg atgtgacaac ctttattggt aataccatca tcattgccgc atgtttgagc 7440
tcaatgatcc ccatggacaa agtgataaag gcagcttttt gtggagacga tagcctgatt 7500

```
tacattccta aaggtttaga cttgcctgat attcaggcgg gcgcgaacct catgtggaac   7560
ttcgaggcca aactcttcag gaagaagtat ggttacttct gtggtcgtta tgttattcac   7620
catgatagag gagccattgt gtattacgat ccgcttaaac taatatctaa gttaggttgt   7680
aaacatatta gagatgttgt tcacttagaa gagttacgcg agtctttgtg tgatgtagct   7740
agtaacttaa ataattgtgc gtatttttca cagttagatg aggccgttgc cgaggttcat   7800
aagaccgcgg taggcggttc gtttgctttt tgtagtataa ttaagtattt gtcagataag   7860
agattgttta gagatttgtt ctttgtttga taatgtcgat agtctcgtac gaacctaagg   7920
tgagtgattt cctcaatctt tcgaagaagg aagagatctt gccgaaggct ctaacgaggt   7980
taaaaaccgt gtctattagt actaaagata ttatatctgt caaggagtcg gagactttgt   8040
gtgatataga tttgttaatc aatgtgccat tagataagta tagatatgtg ggtatcctag   8100
gagccgtttt taccggagag tggctagtgc cagacttcgt taaaggtgga gtgacgataa   8160
gtgtgataga taagcgtctg gtgaactcaa aggagtgcgt gattggtacg tacagagccg   8220
cagccaagag taagaggttc cagttcaaat tggttccaaa ttactttgtg tccaccgtgg   8280
acgcaaagag gaagccgtgg caggtaagga tttttatgat atagtatgct tatgtatttt   8340
gtactgaaag catatcctgc ttcattggga tattactgaa agcatttaac tacatgtaaa   8400
ctcacttgat gatcaataaa cttgattttg caggttcatg ttcgtataca agacttgaag   8460
attgaggcgg gttggcagcc gttagctctg gaagtagttt cagttgctat ggtcaccaat   8520
aacgttgtca tgaagggttt gagggaaaag gtcgtcgcaa taaatgatcc ggacgtcgaa   8580
ggtttcgaag gtaagccatc ttcctgctta tttttataat gaacatagaa ataggaagtt   8640
gtgcagagaa actaattaac ctgactcaaa atctaccctc ataattgttg tttgatattg   8700
gtcttgtatt ttgcaggtgt ggttgacgaa ttcgtcgatt cggttgcagc atttaaagcg   8760
gttgacaact ttaaaagaag gaaaaagaag gttgaagaaa agggtgtagt aagtaagtat   8820
aagtacagac cggagaagta cgccggtcct gattcgttta atttgaaaga agaaaacgtc   8880
ttacaacatt acaaacccga ataatcgata actcgagtat ttttacaaca attaccaaca   8940
acaacaaaca acaaacaaca ttacaattac atttacaatt atcatggtga gcaagggcga   9000
ggagctgttc accggggtgg tgcccatcct ggtcgagctg gacggcgacg taaacggcca   9060
caagttcagc gtgtccggcg agggcgaggg cgatgccacc tacggcaagc tgaccctgaa   9120
gttcatctgc accaccggca agctgcccgt gccctggccc accctcgtga ccaccttcag   9180
ctacggcgtg cagtgcttca gccgctaccc cgaccacatg aagcagcacg acttcttcaa   9240
gtccgccatg cccgaaggct acgtccagga gcgcaccatc ttcttcaagg acgacggcaa   9300
ctacaagacc cgcgccgagg tgaagttcga gggcgacacc ctggtgaacc gcatcgagct   9360
gaagggcatc gacttcaagg aggacggcaa catcctgggg cacaagctgg agtacaacta   9420
caacagccac aacgtctata tcatggccga caagcagaag aacggcatca aggtgaactt   9480
caagatccgc cacaacatcg aggacggcag cgtgcagctc gccgaccact accagcagaa   9540
cacccccatc ggcgacggcc ccgtgctgct gcccgacaac cactacctga gcacccagtc   9600
cgccctgagc aaagacccca acgagaagcg cgatcacatg gtcctgctgg agttcgtgac   9660
cgccgccggg atcactcacg gcatggacga gctgtacaag taaagcggcc cctagagcgt   9720
ggtgcgcacg atagcgcata gtgtttttct ctccacttga atcgaagaga tagacttacg   9780
gtgtaaatcc gtaggggtgg cgtaaaccaa attacgcaat gttttgggtt ccatttaaat   9840
```

cgaaacccct tatttcctgg atcacctgtt aacgcacgtt tgacgtgtat tacagtggga 9900
ataagtaaaa gtgagaggtt cgaatcctcc ctaaccccgg gtaggggccc agcggccgct 9960
ctagctagag tcaagcagat cgttcaaaca tttggcaata aagtttctta agattgaatc 10020
ctgttgccgg tcttgcgatg attatcatat aatttctgtt gaattacgtt aagcatgtaa 10080
taattaacat gtaatgcatg acgttattta tgagatgggt ttttatgatt agagtcccgc 10140
aattatacat ttaatacgcg atagaaaaca aaatatagcg cgcaaactag gataaattat 10200
cgcgcgcggt gtcatctatg ttactagatc gacctgcatc caccccagta cattaaaaac 10260
gtccgcaatg tgttattaag ttgtctaagc gtcaatttgt ttacaccaca atatatcctg 10320
ccaccagcca gccaacagct ccccgaccgg cagctcggca caaaatcacc actcgataca 10380
ggcagcccat cag 10393

<210> SEQ ID NO 3
<211> LENGTH: 10397
<212> TYPE: DNA
<213> ORGANISM: Artificial Sequence
<220> FEATURE:
<223> OTHER INFORMATION: T-DNA region of pNMD570

<400> SEQUENCE: 3
cctgtggttg gcacatacaa atggacgaac ggataaacct tttcacgccc ttttaaatat 60
ccgattattc taataaacgc tcttttctct taggtttacc cgccaatata tcctgtcaaa 120
cactgatagt ttaaactgaa ggcgggaaac gacaatctga tctaagctag cttggaattg 180
gtaccacgcg tttcgacaaa atttagaacg aacttaatta tgatctcaaa tacattgata 240
catatctcat ctagatctag gttatcatta tgtaagaaag ttttgacgaa tatggcacga 300
caaaatggct agactcgatg taattggtat ctcaactcaa cattatactt ataccaaaca 360
ttagttagac aaaatttaaa caactatttt ttatgtatgc aagagtcagc atatgtataa 420
ttgattcaga atcgttttga cgagttcgga tgtagtagta gccattattt aatgtacata 480
ctaatcgtga atagtgaata tgatgaaaca ttgtatctta ttgtataaat atccataaac 540
acatcatgaa agacactttc tttcacggtc tgaattaatt atgatacaat tctaatagaa 600
aacgaattaa attacgttga attgtatgaa atctaattga acaagccaac cacgacgacg 660
actaacgttg cctggattga ctcggtttaa gttaaccact aaaaaaacgg agctgtcatg 720
taacacgcgg atcgagcagg tcacagtcat gaagccatca aagcaaaaga actaatccaa 780
gggctgagat gattaattag tttaaaaatt agttaacacg agggaaaagg ctgtctgaca 840
gccaggtcac gttatcttta cctgtggtcg aaatgattcg tgtctgtcga ttttaattat 900
ttttttgaaa ggccgaaaat aaagttgtaa gagataaacc cgcctatata aattcatata 960
ttttcctctc cgctttgaag ttttagtttt attgcaacaa caacaacaaa ttacaataac 1020
aacaaacaaa atacaaacaa caacaacatg gcacaatttc aacaaacaat tgacatgcaa 1080
actctccaag ccgctgcggg acgcaacagc ttggtgaatg atttggcatc tcgtcgcgtt 1140
tacgataatg cagtcgagga gctgaatgct cgttccagac gtcccaaggt aataggaact 1200
ttctggatct actttatttg ctggatctcg atcttgtttt ctcaatttcc ttgagatctg 1260
gaattcgttt aatttggatc tgtgaacctc cactaaatct tttggtttta ctagaatcga 1320
tctaagttga ccgatcagtt agctcgatta tagctaccag aatttggctt gaccttgatg 1380
gagagatcca tgttcatgtt acctgggaaa tgatttgtat atgtgaattg aaatctgaac 1440
tgttgaagtt agattgaatc tgaacactgt caatgttaga ttgaatctga acactgttta 1500

```
aggttagatg aagtttgtgt atagattctt cgaaacttta ggatttgtag tgtcgtacgt   1560
tgaacagaaa gctatttctg attcaatcag ggtttatttg actgtattga actcttttttg   1620
tgtgtttgca ggtccacttc tccaaggcag tgtctacgga acagaccctg attgcaacaa   1680
acgcatatcc ggagttcgag atttccttta ctcatacgca atccgctgtg cactccttgg   1740
ccggaggcct tcggtcactt gagttggagt atctcatgat gcaagttccg ttcggttctc   1800
tgacgtacga catcggcggt aacttttccg cgcacctttt caaagggcgc gattacgttc   1860
actgctgcat gcctaatctg gatgtacgtg acattgctcg ccatgaagga cacaaggaag   1920
ctatttacag ttatgtgaat cgtttgaaaa ggcagcagcg tcctgtgcct gaataccaga   1980
gggcagcttt caacaactac gctgagaacc cgcacttcgt ccattgcgac aaacctttcc   2040
aacagtgtga attgacgaca gcgtatggca ctgacaccta cgctgtagct ctccatagca   2100
tttatgatat ccctgttgag gagttcggtt ctgcgctact caggaagaat gtgaaaactt   2160
gtttcgcggc ctttcatttc catgagaata tgcttctaga ttgtgataca gtcacactcg   2220
atgagattgg agctacgttc cagaaatcag gtaacattcc ttagttacct ttcttttctt   2280
tttccatcat aagtttatag attgtacatg ctttgagatt tttctttgca aacaatctca   2340
ggtgataacc tgagcttctt cttccataat gagagcactc tcaattacac ccacagcttc   2400
agcaacatca tcaagtacgt gtgcaagacg ttcttccctg ctagtcaacg cttcgtgtac   2460
cacaaggagt tcctggtcac tagagtcaac acttggtact gcaagttcac gagagtggat   2520
acgttcactc tgttccgtgg tgtgtaccac aacaatgtgg attgcgaaga gttttacaag   2580
gctatggacg atgcgtggca ctacaaaaag acgttagcaa tgcttaatgc cgagaggacc   2640
atcttcaagg ataacgctgc gttaaacttc tggttcccga aggtgctctt gaaattggaa   2700
gtcttctttt gttgtctaaa cctatcaatt tctttgcgga aatttatttg aagctgtaga   2760
gttaaaattg agtcttttaa acttttgtag gtgagagaca tggttatcgt ccctctcttt   2820
gacgcttcta tcacaactgg taggatgtct aggagagagg ttatggtgaa caaggacttc   2880
gtctacacgg tcctaaatca catcaagacc tatcaagcta aggcactgac gtacgcaaac   2940
gtgctgagct tcgtggagtc tattaggtct agagtgataa ttaacggtgt cactgccagg   3000
taagttgtta cttatgattg ttttcctctc tgctacatgt attttgttgt tcatttctgt   3060
aagatataag aattgagttt tcctctgatg atattattag gtctgaatgg gacacagaca   3120
aggcaattct aggtccatta gcaatgacat tcttcctgat cacgaagctg ggtcatgtgc   3180
aagatgaaat aatcctgaaa aagttccaga agttcgacag aaccaccaat gagctgattt   3240
ggacaagtct ctgcgatgcc ctgatggggg ttattccctc ggtcaaggag acgcttgtgc   3300
gcggtggttt tgtgaaagta gcagaacaag ccttagagat caaggttagt atcatatgaa   3360
gaaataccta gtttcagttg atgaatgcta ttttctgacc tcagttgttc tcttttgaga   3420
attatttctt ttctaatttg cctgattttt ctattaattc attaggttcc cgagctatac   3480
tgtaccttcg ccgaccgatt ggtactacag tacaagaagg cggaggagtt ccaatcgtgt   3540
gatctttcca aacctctaga agagtcagag aagtactaca acgcattatc cgagctatca   3600
gtgcttgaga atctcgactc ttttgactta gaggcgttta agactttatg tcagcagaag   3660
aatgtggacc cggatatggc agcaaaggta aatcctggtc cacactttta cgataaaaac   3720
acaagatttt aaactatgaa ctgatcaata atcattccta aaagaccaca cttttgtttt   3780
gtttctaaag taatttttac tgttataaca ggtggtcgta gcaatcatga agtcagaatt   3840
```

-continued gacgttgcct ttcaagaaac ctacagaaga ggaaatctcg gagtcgctaa aaccaggaga 3900
ggggtcgtgt gcagagcata aggaagtgtt gagcttacaa aatgatgctc cgttcccgtg 3960
tgtgaaaaat ctagttgaag gttccgtgcc ggcgtatgga atgtgtccta agggtggtgg 4020
tttcgacaaa ttggatgtgg acattgctga tttccatctc aagagtgtag atgcagttaa 4080
aaagggaact atgatgtctg cggtgtacac agggtctatc aaagttcaac aaatgaagaa 4140
ctacatagat tacttaagtg cgtcgctggc agctacagtc tcaaacctct gcaaggtaag 4200
aggtcaaaag gtttccgcaa tgatccctct ttttttgttt ctctagtttc aagaatttgg 4260
gtatatgact aacttctgag tgttccttga tgcatatttg tgatgagaca aatgtttgtt 4320
ctatgtttta ggtgcttaga gatgttcacg gcgttgaccc agagtcacag gagaaatctg 4380
gagtgtggga tgttaggaga ggacgttggt tacttaaacc taatgcgaaa agtcacgcgt 4440
ggggtgtggc agaagacgcc aaccacaagt tggttattgt gttactcaac tgggatgacg 4500
gaaagccggt ttgtgatgag acatggttca gggtggcggt gtcaagcgat tccttgatat 4560
attcggatat gggaaaactt aagacgctca cgtcttgcag tccaaatggt gagccaccgg 4620
agcctaacgc caaagtaatt ttggtcgatg gtgttcccgg ttgtggaaaa acgaaggaga 4680
ttatcgaaaa ggtaagttct gcatttggtt atgctccttg cattttaggt gttcgtcgct 4740
cttccatttc catgaatagc taagattttt tttctctgca ttcattcttc ttgcctcagt 4800
tctaactgtt tgtggtattt ttgttttaat tattgctaca ggtaaacttc tctgaagact 4860
tgattttagt ccctgggaag gaagcttcta agatgatcat ccggagggcc aaccaagctg 4920
gtgtgataag agcggataag gacaatgtta gaacggtgga ttccttcttg atgcatcctt 4980
ctagaagggt gtttaagagg ttgtttatcg atgaaggact aatgctgcat acaggttgtg 5040
taaatttcct actgctgcta tctcaatgtg acgtcgcata tgtgtatggg gacacaaagc 5100
aaattccgtt catttgcaga gtcgcgaact ttccgtatcc agcgcatttt gcaaaactcg 5160
tcgctgatga gaaggaagtc agaagagtta cgctcaggta aagcaactgt gttttaatca 5220
atttcttgtc aggatatatg gattataact taatttttga gaaatctgta gtatttggcg 5280
tgaaatgagt ttgctttttg gtttctcccg tgttataggt gcccggctga tgttacgtat 5340
ttccttaaca agaagtatga cggggcggtg atgtgtacca gcgcggtaga gagatccgtg 5400
aaggcagaag tggtgagagg aaagggtgca ttgaacccaa taaccttacc gttggagggt 5460 aaaatttga ccttcacaca agctgacaag ttcgagttac tggagaaggg ttacaaggta 5520
aagtttccaa ctttccttta ccatatcaaa ctaaagttcg aaacttttta tttgatcaac 5580
ttcaaggcca cccgatcttt ctattcctga ttaatttgtg atgaatccat attgactttt 5640
gatggttacg caggatgtga acactgtgca cgaggtgcaa ggggagacgt acgagaagac 5700
tgctattgtg cgcttgacat caactccgtt agagatcata tcgagtgcgt cacctcatgt 5760
tttggtggcg ctgacaagac acacaacgtg ttgtaaatat tacaccgttg tgttggaccc 5820
gatggtgaat gtgatttcag aaatggagaa gttgtccaat ttccttcttg acatgtatag 5880
agttgaagca ggtctgtctt tcctatttca tatgtttaat cctaggaatt tgatcaattg 5940
attgtatgta tgtcgatccc aagactttct tgttcactta tatcttaact ctctctttgc 6000
tgtttcttgc aggtgtccaa tagcaattac aaatcgatgc agtattcagg ggacagaact 6060
tgtttgttca gacgcccaag tcaggagatt ggcgagatat gcaattttac tatgacgctc 6120
ttcttcccgg aaacagtact attctcaatg aatttgatgc tgttacgatg aatttgaggg 6180
atatttcctt aaacgtcaaa gattgcagaa tcgacttctc caaatccgtg caacttccta 6240

```
aagaacaacc tattttcctc aagcctaaaa taagaactgc ggcagaaatg ccgagaactg   6300
caggtaaaat attggatgcc agacgatatt ctttcttttg atttgtaact ttttcctgtc   6360
aaggtcgata aattttattt tttttggtaa aaggtcgata attttttttt ggagccatta   6420
tgtaattttc ctaattaact gaaccaaaat tatacaaacc aggtttgctg gaaaatttgg   6480
ttgcaatgat caaaagaaac atgaatgcgc cggatttgac agggacaatt gacattgagg   6540
atactgcatc tctggtggtt gaaaagtttt gggattcgta tgttgacaag gaatttagtg   6600
gaacgaacga aatgaccatg acaagggaga gcttctccag gtaaggactt ctcatgaata   6660
ttagtggcag attagtgttg ttaaagtctt tggttagata atcgatgcct cctaattgtc   6720
catgttttac tggttttcta caattaaagg tggctttcga aacaagagtc atctacagtt   6780
ggtcagttag cggactttaa ctttgtggat ttgccggcag tagatgagta caagcatatg   6840
atcaagagtc aaccaaagca aaagttagac ttgagtattc aagacgaata tcctgcattg   6900
cagacgatag tctaccattc gaaaaagatc aatgcgattt tcggtccaat gttttcagaa   6960
cttacgagga tgttactcga aaggattgac tcttcgaagt ttctgttcta caccagaaag   7020
acacctgcac aaatagagga cttcttttct gacctagact caacccaggc gatggaaatt   7080
ctggaactcg acatttcgaa gtacgataag tcacaaaacg agttccattg tgctgtagag   7140
tacaagatct gggaaaagtt aggaattgat gagtggctag ctgaggtctg gaaacaaggt   7200
gagttcctaa gttccatttt tttgtaatcc ttcaatgtta ttttaacttt tcagatcaac   7260
atcaaaatta ggttcaattt tcatcaacca aataatattt ttcatgtata tataggtcac   7320
agaaaaacga ccttgaaaga ttatacggcc ggaatcaaaa catgtctttg gtatcaaagg   7380
aaaagtggtg atgtgacaac ctttattggt aataccatca tcattgccgc atgtttgagc   7440
tcaatgatcc ccatggacaa agtgataaag gcagcttttt gtggagacga tagcctgatt   7500
tacattccta aaggtttaga cttgcctgat attcaggcgg gcgcgaacct catgtggaac   7560
ttcgaggcca aactcttcag gaagaagtat ggttacttct gtggtcgtta tgttattcac   7620
catgatagag gagccattgt gtattacgat ccgcttaaac taatatctaa gttaggttgt   7680
aaacatatta gagatgttgt tcacttagaa gagttacgcg agtctttgtg tgatgtagct   7740
agtaacttaa ataattgtgc gtatttttca cagttagatg aggccgttgc cgaggttcat   7800
aagaccgcgg taggcggttc gtttgctttt tgtagtataa ttaagtattt gtcagataag   7860
agattgttta gagatttgtt ctttgtttga taatgtcgat agtctcgtac gaacctaagg   7920
tgagtgattt cctcaatctt tcgaagaagg aagagatctt gccgaaggct ctaacgaggt   7980
taaaaaccgt gtctattagt actaaagata ttatatctgt caaggagtcg gagactttgt   8040
gtgatataga tttgttaatc aatgtgccat tagataagta tagatatgtg ggtatcctag   8100
ctaggagccg tttttaccgg agagtggcta gtgccagact tcgttaaagg tggagtgacg   8160
ataagtgtga tagataagcg tctggtgaac tcaaaggagt gcgtgattgg tacgtacaga   8220
gccgcagcca agagtaagag gttccagttc aaattggttc caaattactt tgtgtccacc   8280
gtggacgcaa agaggaagcc gtggcaggta aggattttta tgatatagta tgcttatgta   8340
ttttgtactg aaagcatatc ctgcttcatt gggatattac tgaaagcatt taactacatg   8400
taaactcact tgatgatcaa taaacttgat tttgcaggtt catgttcgta tacaagactt   8460
gaagattgag gcgggttggc agccgttagc tctggaagta gtttcagttg ctatggtcac   8520
caataacgtt gtcatgaagg gtttgaggga aaaggtcgtc gcaataaatg atccggacgt   8580
```

```
cgaaggtttc gaaggtaagc catcttcctg cttattttta taatgaacat agaaatagga   8640

agttgtgcag agaaactaat taacctgact caaaatctac cctcataatt gttgtttgat   8700

attggtcttg tattttgcag gtgtggttga cgaattcgtc gattcggttg cagcatttaa   8760

agcggttgac aactttaaaa gaaggaaaaa gaaggttgaa gaaaagggtg tagtaagtaa   8820

gtataagtac agaccggaga agtacgccgg tcctgattcg tttaatttga aagaagaaaa   8880

cgtcttacaa cattacaaac ccgaataatc gataactcga gtatttttac aacaattacc   8940

aacaacaaca aacaacaaac aacattacaa ttacatttac aattatcatg gtgagcaagg   9000

gcgaggagct gttcaccggg gtggtgccca tcctggtcga gctggacggc gacgtaaacg   9060

gccacaagtt cagcgtgtcc ggcgagggcg agggcgatgc cacctacggc aagctgaccc   9120

tgaagttcat ctgcaccacc ggcaagctgc ccgtgccctg gcccaccctc gtgaccacct   9180

tcagctacgg cgtgcagtgc ttcagccgct accccgacca catgaagcag cacgacttct   9240

tcaagtccgc catgcccgaa ggctacgtcc aggagcgcac catcttcttc aaggacgacg   9300

gcaactacaa gacccgcgcc gaggtgaagt tcgagggcga caccctggtg aaccgcatcg   9360

agctgaaggg catcgacttc aaggaggacg gcaacatcct ggggcacaag ctggagtaca   9420

actacaacag ccacaacgtc tatatcatgg ccgacaagca gaagaacggc atcaaggtga   9480

acttcaagat ccgccacaac atcgaggacg gcagcgtgca gctcgccgac cactaccagc   9540

agaacacccc catcggcgac ggccccgtgc tgctgcccga caaccactac ctgagcaccc   9600

agtccgccct gagcaaagac cccaacgaga agcgcgatca catggtcctg ctggagttcg   9660

tgaccgccgc cgggatcact cacggcatgg acgagctgta caagtaaagc ggcccctaga   9720

gcgtggtgcg cacgatagcg catagtgttt ttctctccac ttgaatcgaa gagatagact   9780

tacggtgtaa atccgtaggg gtggcgtaaa ccaaattacg caatgttttg ggttccattt   9840

aaatcgaaac cccttatttc ctggatcacc tgttaacgca cgtttgacgt gtattacagt   9900

gggaataagt aaaagtgaga ggttcgaatc ctccctaacc ccgggtaggg gcccagcggc   9960

cgctctagct agagtcaagc agatcgttca aacatttggc aataaagttt cttaagattg  10020

aatcctgttg ccggtcttgc gatgattatc atataatttc tgttgaatta cgttaagcat  10080

gtaataatta acatgtaatg catgacgtta tttatgagat gggtttttat gattagagtc  10140

ccgcaattat acatttaata cgcgatagaa aacaaaatat agcgcgcaaa ctaggataaa  10200

ttatcgcgcg cggtgtcatc tatgttacta gatcgacctg catccacccc agtacattaa  10260

aaacgtccgc aatgtgttat taagttgtct aagcgtcaat ttgtttacac cacaatatat  10320

cctgccacca gccagccaac agctccccga ccggcagctc ggcacaaaat caccactcga  10380

tacaggcagc ccatcag                                                 10397
```

<210> SEQ ID NO 4
<211> LENGTH: 7351
<212> TYPE: DNA
<213> ORGANISM: Artificial Sequence
<220> FEATURE:
<223> OTHER INFORMATION: T-DNA region of pNMD620

<400> SEQUENCE: 4

```
cctgtggttg gcacatacaa atggacgaac ggataaacct tttcacgccc ttttaaatat     60

ccgattattc taataaacgc tcttttctct taggtttacc cgccaatata tcctgtcaaa    120

cactgatagt ttaaactgaa ggcgggaaac gacaatctga tctaagctag gcatgcctgc    180

aggtcaacat ggtggagcac gacacgcttg tctactccaa aaatatcaaa gatacagtct    240
```

```
cagaagacca aagggcaatt gagacttttc aacaaagggt aatatccgga aacctcctcg    300
gattccattg cccagctatc tgtcacttta ttgtgaagat agtggaaaag gaaggtggct    360
cctacaaatg ccatcattgc gataaaggaa aggccatcgt tgaagatgcc tctgccgaca    420
gtggtcccaa agatggaccc ccacccacga ggagcatcgt ggaaaaagaa gacgttccaa    480
ccacgtcttc aaagcaagtg gattgatgtg atatctccac tgacgtaagg gatgacgcac    540
aatcccacta tccttcgcaa gacccttcct ctatataagg aagttcattt catttggaga    600
ggagaaaact aaaccataca ccaccaacac aaccaaaccc accacgccca attgttacac    660
acccgcttga aaaagaaagt ttaacaaatg gccaaggtgc gcgaggttta ccaatctttt    720
acagactcca ccacaaaaac tctcatccaa gatgaggctt atagaaacat tcgccccatc    780
atggaaaaac acaaactagc taacccttac gctcaaacgg ttgaagcggc taatgatcta    840
gaggggttcg gcatagccac caatccctat agcattgaat tgcatacaca tgcagccgct    900
aagaccatag agaataaact tctagaggtg cttggttcca tcctaccaca agaacctgtt    960
acatttatgt ttcttaaacc cagaaagcta aactacatga gaagaaaccc gcggatcaag   1020
gacattttcc aaaatgttgc cattgaacca agagacgtag ccaggtaccc caaggaaaca   1080
ataattgaca aactcacaga gatcacaacg gaaacagcat acattagtga cactctgcac   1140
ttcttggatc cgagctacat agtggagaca ttccaaaact gcccaaaatt gcaaacattg   1200
tatgcgacct tagttctccc cgttgaggca gcctttaaaa tggaaagcac tcacccgaac   1260
atatacagcc tcaaatactt cggagatggt ttccagtata taccaggcaa ccatggtggc   1320
ggggcatacc atcatgaatt cgctcatcta caatggctca aagtgggaaa gatcaagtgg   1380
agggacccca aggatagctt tctcggacat ctcaattaca cgactgagca ggttgagatg   1440
cacacagtga cagtacagtt gcaggaatcg ttcgcggcaa accacttgta ctgcatcagg   1500
agaggagact tgctcacacc ggaggtgcgc actttcggcc aacctgacag gtacgtgatt   1560
ccaccacaga tcttcctccc aaaagttcac aactgcaaga agccgattct caagaaaact   1620
atgatgcagc tcttcttgta tgttaggaca gtcaaggtcg caaaaaattg tgacattttt   1680
gccaaagtca gacaattaat taaatcatct gacttggaca aatactctgc tgtggaactg   1740
gtttacttag taagctacat ggagttcctt gccgatttac aagctaccac ctgcttctca   1800
gacacacttt ctggtggctt gctaacaaag acccttgcac cggtgagggc ttggatacaa   1860
gagaaaaaga tgcagctgtt tggtcttgag gactacgcga agttagtcaa agcagttgat   1920
ttccacccgg tggatttttc tttcaaagtg gaaacttggg acttcagatt ccaccccttg   1980
caagcgtgga aagccttccg accaagggaa gtgtcggatg tagaggaaat ggaaagtttg   2040
ttctcagatg ggacctgct tgattgcttc acaagaatgc cagcttatgc ggtaaacgca    2100
gaggaagatt tagctgcaat caggaaaacg cccgagatgg atgtcggtca agaagttaaa   2160
gagcctgcag gagacagaaa tcaatactca aaccctgcag aaactttcct caacaagctc   2220
cacaggaaac acagtaggga ggtgaaacac caggccgcaa agaaagctaa acgcctagct   2280
gaaatccagg agtcaatgag agctgaaggt gatgccgaac caaatgaaat aagcgggacg   2340
atgggggcaa tacccagcaa cgccgaactt cctggcacga atgatgccag acaagaactc   2400
acactcccaa ccactaaacc tgtccctgca aggtgggaag atgcttcatt cacagattct   2460
agtgtggaag aggagcaggt taaactcctt ggaaaagaaa ccgttgaaac agcgacgcaa   2520
caagtcatcg aaggacttcc ttggaaacac tggattcctc aattaaatgc tgttggattc   2580
```

-continued

```
aaggcgctgg aaattcagag ggataggagt ggaacaatga tcatgcccat cacagaaatg   2640
gtctccgggc tggaaaaaga ggacttccct gaaggaactc caaaagagtt ggcacgagaa   2700
ttgttcgcta tgaacagaag ccctgccacc atccctttgg acctgcttag agccagagac   2760
tacggcagtg atgtaaagaa caagagaatt ggtgccatca caaagacaca ggcaacgagt   2820
tggggcgaat acttgacagg aaagatagaa agcttaactg agaggaaagt tgcgacttgt   2880
gtcattcatg gagctggagg ttctggaaaa agtcatgcca tccagaaggc attgagagaa   2940
attggcaagg gctcggacat cactgtagtc ctgccgacca atgaactgcg gctagattgg   3000
agtaagaaag tgcctaacac tgagccctat atgttcaaga cctctgaaaa ggcgttaatt   3060
gggggaacag gcagcatagt catctttgac gattactcaa aacttcctcc cggttacata   3120
gaagccttag tctgtttcta ctctaaaatc aagctaatca ttctaacagg agatagcaga   3180
caaagcgtct accatgaaac tgctgaggac gcctccatca ggcatttggg accagcaaca   3240
gagtacttct caaaatactg ccgatactat ctcaatgcca cacaccgcaa caagaaagat   3300
cttgcgaaca tgcttggtgt ctacagtgag agaacgggag tcaccgaaat cagcatgagc   3360
gccgagttct tagaaggaat cccaactttg gtaccctcgg atgagaagag aaagctgtac   3420
atgggcaccg ggaggaatga cacgttcaca tacgctggat gccaggggct aactaagccg   3480
aaggtacaaa tagtgttgga ccacaacacc caagtgtgta gcgcgaatgt gatgtacacg   3540
gcactttcta gagccaccga taggattcac ttcgtgaaca caagtgcaaa ttcctctgcc   3600
ttctgggaaa agttggacag caccccttac ctcaagactt tcctatcagt ggtgagagaa   3660
caagcactca gggagtacga gccggcagag gcagagccaa ttcaagagcc tgagccccag   3720
acacacatgt gtgtcgagaa tgaggagtcc gtgctagaag agtacaaaga ggaactcttg   3780
gaaaagtttg acagagagat ccactctgaa tcccatggtc attcaaactg tgtccaaact   3840
gaagacacaa ccattcagtt gttttcgcat caacaagcaa aagatgagac cctcctctgg   3900
gcgactatag atgcgcggct caagaccagc aatcaagaaa caaacttccg agaattcctg   3960
agcaagaagg acattgggga cgttctgttt ttaaactacc aaaaagctat gggtttaccc   4020
aaagagcgta ttcctttttc ccaagaggtc tgggaagctt gtgcccacga agtacaaagc   4080
aagtacctca gcaagtcaaa gtgcaacttg atcaatggga ctgtgagaca gagcccagac   4140
ttcgatgaaa ataagattat ggtattcctc aagtcgcagt gggtcacaaa ggtggaaaaa   4200
ctaggtctac ccaagattaa gccaggtcaa accatagcag ccttttacca gcagactgtg   4260
atgctttttg gaactatggc taggtacatg cgatggttca gacaggcttt ccagccaaaa   4320
gaagtcttca taaactgtga gaccacgcca gatgacatgt ctgcatgggc cttgaacaac   4380
tggaatttca gcagacctag cttggctaat gactacacag ctttcgacca gtctcaggat   4440
ggagccatgt tgcaatttga ggtgctcaaa gccaaacacc actgcatacc agaggaaatc   4500
attcaggcat acatagatat taagactaat gcacagattt tcctaggcac gttatcaatt   4560
atgcgcctga ctggtgaagg tcccactttt gatgcaaaca ctgagtgcaa catagcttac   4620
acccatacaa agtttgacat cccagccgga actgctcaag tttatgcagg agacgactcc   4680
gcactggact gtgttccaga agtgaagcat agtttccaca ggcttgagga caaattactc   4740
ctaaagtcaa agcctgtaat cacgcagcaa aagaagggca gttggcctga gttttgtggt   4800
tggctgatca caccaaaagg ggtgatgaaa gacccaatta agctccatgt tagcttaaaa   4860
ttggctgaag ctaagggtga actcaagaaa tgtcaagatt cctatgaaat tgatctgagt   4920
tatgcctatg accacaagga ctctctgcat gacttgttcg atgagaaaca gtgtcaggca   4980
```

-continued

```
cacacactca cttgcagaac actaatcaag tcagggagag gcactgtctc actttcccgc   5040
ctcagaaact ttctttaacc gttaagttac cttagagatt tgaataagat ggatattctc   5100
atcagtagtt tgaaaagttt aggttattct aggacttcca aatctttaga ttcaggacct   5160
ttggtagtac atgcagtagc cggagccggt aagtccacag ccctaaggaa gttgatcctc   5220
agacacccaa cattcaccgt gcatacactc ggtgtccctg acaaggtgag tatcagaact   5280
agaggcatac agaagccagg acctattcct gagggcaact tcgcaatcct cgatgagtat   5340
actttggaca acaccacaag gaactcatac caggcacttt ttgctgaccc ttatcaggca   5400
ccggagttta gcctagagcc ccacttctac ttggaaacat catttcgagt tccgaggaaa   5460
gtggcagatt tgatagctgg ctgtggcttc gatttcgaga cgaactcacc ggaagaaggg   5520
cacttagaga tcactggcat attcaaaggg cccctactcg gaaaggtgat agccattgat   5580
gaggagtctg agacaacact gtccaggcat ggtgttgagt ttgttaagcc ctgccaagtg   5640
acgggacttg agttcaaagt agtcactatt gtgtctgccg caccaataga ggaaattggc   5700
cagtccacag ctttctacaa cgctatcacc aggtcaaagg gattgacata tgtccgcgca   5760
gggccatagg ctgaccgctc cggtcaattc tgaaaaagtg tacatagtat taggtctatc   5820
atttgcttta gtttcaatta cctttctgct ttctagaaat agcttacccc acgtcggtga   5880
caacattcac agcttgccac acggaggagc ttacagagac ggcaccaaag caatcttgta   5940
caactcccca aatctagggt cacgagtgag tctacacaac ggaaagaacg cagcatttgc   6000
tgccgttttg ctactgactt tgctgatcta tggaagtaaa tacatatctc aacgcaatca   6060
tacttgtgct tgtggtaaca atcatagcag tcattagcac ttccttagtg aggactgaac   6120
cttgtgtcat caagattact ggggaatcaa tcacagtgtt ggcttgcaaa ctagatgcag   6180
aaaccataag ggccattgcc gatctcaagc cactctccgt tgaacggtta agtttccatt   6240
gatactcgaa agaggtcagc accagctagc aacaaacaag aaaggtatgg tgagcaaggg   6300
cgaggagctg ttcaccgggg tggtgcccat cctggtcgag ctggacggcg acgtaaacgg   6360
ccacaagttc agcgtgtccg gcgagggcga gggcgatgcc acctacggca agctgaccct   6420
gaagttcatc tgcaccaccg gcaagctgcc cgtgccctgg cccaccctcg tgaccacctt   6480
cagctacggc gtgcagtgct tcagccgcta ccccgaccac atgaagcagc acgacttctt   6540
caagtccgcc atgcccgaag gctacgtcca ggagcgcacc atcttcttca aggacgacgg   6600
caactacaag acccgcgccg aggtgaagtt cgagggcgac accctggtga accgcatcga   6660
gctgaagggc atcgacttca aggaggacgg caacatcctg gggcacaagc tggagtacaa   6720
ctacaacagc cacaacgtct atatcatggc cgacaagcag aagaacggca tcaaggtgaa   6780
cttcaagatc cgccacaaca tcgaggacgg cagcgtgcag ctcgccgacc actaccagca   6840
gaacaccccc atcggcgacg gccccgtgct gctgcccgac aaccactacc tgagcaccca   6900
gtccgccctg agcaaagacc ccaacgagaa gcgcgatcac atggtcctgc tggagttcgt   6960
gaccgccgcc gggatcactc acggcatgga cgagctgtac aagtaagctt ggtcgtatca   7020
ctggaacaac aaccgctgag gctgttgtca ctctaccacc accataacta cgtctacata   7080
accgacgcct accccagttt catagtattt tctggtttga ttgtatgaat aatataaata   7140
aaaaaaaaaa aaaaaaaaaa aaactagtga gctcttctgt cagcgggccc actgcatcca   7200
ccccagtaca ttaaaaacgt ccgcaatgtg ttattaagtt gtctaagcgt caatttgttt   7260
acaccacaat atatcctgcc accagccagc caacagctcc ccgaccggca gctcggcaca   7320
```

aaatcaccac tcgatacagg cagcccatca g 7351

<210> SEQ ID NO 5
<211> LENGTH: 1018
<212> TYPE: DNA
<213> ORGANISM: Artificial Sequence
<220> FEATURE:
<223> OTHER INFORMATION: Plasmid backbone insertion containing virG gene of pNMD062

<400> SEQUENCE: 5
ctgtcgatca gatctggctc gcggcggacg cacgacgccg gggcgagacc ataggcgatc 60
tcctaaatca atagtagctg taacctcgaa gcgtttcact tgtaacaacg attgagaatt 120
tttgtcataa aattgaaata cttggttcgc atttttgtca tccgcggtca gccgcaattc 180
tgacgaactg cccatttagc tggagatgat tgtacatcct tcacgtgaaa atttctcaag 240
cgctgtgaac aagggttcag attttagatt gaaaggtgag ccgttgaaac acgttcttct 300
tgtcgatgac gacgtcgcta tgcggcatct tattattgaa taccttacga tccacgcctt 360
caaagtgacc gcggtagccg acagcaccca gttcacaaga gtactctctt ccgcgacggt 420
cgatgtcgtg gttgttgatc taaatttagg tcgtgaagat gggctcgaga tcgttcgtaa 480
tctggcggca aagtctgata ttccaatcat aattatcagt ggcgaccgcc ttgaggagac 540
ggataaagtt gttgcactcg agctaggagc aagtgatttt atcgctaagc cgttcagtat 600
cagagagttt ctagcacgca ttcgggttgc cttgcgcgtg cgccccaacg ttgtccgctc 660
caaagaccga cggtcttttt gttttactga ctggacactt aatctcaggc aacgtcgctt 720
gatgtccgaa gctggcggtg aggtgaaact tacggcaggt gagttcaatc ttctcctcgc 780
gtttttagag aaaccccgcg acgttctatc gcgcgagcaa cttctcattg ccagtcgagt 840
acgcgacgag gaggtttatg acaggagtat agatgttctc attttgaggc tgcgccgcaa 900
acttgaggcg gatccgtcaa gccctcaact gataaaaaca gcaagaggtg ccggttattt 960
ctttgacgcg gacgtgcagg tttcgcacgg ggggacgatg gcagcctaag atcgacag 1018

<210> SEQ ID NO 6
<211> LENGTH: 1018
<212> TYPE: DNA
<213> ORGANISM: Artificial Sequence
<220> FEATURE:
<223> OTHER INFORMATION: Plasmid backbone insertion containing virG gene of pNMD063

<400> SEQUENCE: 6
ctgtcgatca gatctggctc gcggcggacg cacgacgccg gggcgagacc ataggcgatc 60
tcctaaatca atagtagctg taacctcgaa gcgtttcact tgtaacaacg attgagaatt 120
tttgtcataa aattgaaata cttggttcgc atttttgtca tccgcggtca gccgcaattc 180
tgacgaactg cccatttagc tggagatgat tgtacatcct tcacgtgaaa atttctcaag 240
tgctgtgaac aagggttcag attttagatt gaaaggtgag ccgttgaaac acgttcttct 300
tgtcgatgac gacgtcgcta tgcggcatct tattattgaa taccttacga tccacgcctt 360
caaagtgacc gcggtagccg acagcaccca gttcacaaga gtactctctt ccgcgacggt 420
cgatgtcgtg gttgttgatc tagatttagg tcgtgaagat gggctcgaga tcgttcgtaa 480
tctggcggca aagtctgata ttccaatcat aattatcagt ggcgaccgcc ttgaggagac 540
ggataaagtt gttgcactcg agctaggagc aagtgatttt atcgctaagc cgttcagtat 600
cagagagttt ctagcacgca ttcgggttgc cttgcgcgtg cgccccaacg ttgtccgctc 660

```
caaagaccga cggtcttttt gttttactga ctggacactt aatctcaggc aacgtcgctt    720

gatgtccgaa gctggcggtg aggtgaaact tacggcaggt gagttcaatc ttctcctcgc    780

gtttttagag aaaccccgcg acgttctatc gcgcgagcaa cttctcattg ccagtcgagt    840

acgcgacgag gaggtttatg acaggagtat agatgttctc attttgaggc tgcgccgcaa    900

acttgaggcg gatccgtcaa gccctcaact gataaaaaca gcaagaggtg ccggttattt    960

ctttgacgcg gacgtgcagg tttcgcacgg ggggacgatg gcagcctaag atcgacag     1018
```

<210> SEQ ID NO 7
<211> LENGTH: 10627
<212> TYPE: DNA
<213> ORGANISM: Artificial Sequence
<220> FEATURE:
<223> OTHER INFORMATION: full-length nucleotide sequence of pNMD1971

<400> SEQUENCE: 7

```
ttaagattga atcctgttgc cggtcttgcg atgattatca tataatttct gttgaattac     60

gttaagcatg taataattaa catgtaatgc atgacgttat ttatgagatg ggtttttatg    120

attagagtcc cgcaattata catttaatac gcgatagaaa acaaaatata gcgcgcaaac    180

taggataaat tatcgcgcgc ggtgtcatct atgttactag atcgacctgc aggcatgcca    240

attccaatcc cacaaaaatc tgagcttaac agcacagttg ctcctctcag agcagaatcg    300

ggtattcaac accctcatat caactactac gttgtgtata acggtccaca tgccggtata    360

tacgatgact ggggttgtac aaaggcggca acaaacggcg ttcccggagt tgcacacaag    420

aaatttgcca ctattacaga ggcaagagca gcagctgacg cgtacacaac aagtcagcaa    480

acagacaggt tgaacttcat ccccaaagga gaagctcaac tcaagcccaa gagctttgct    540

aaggccctaa caagcccacc aaagcaaaaa gcccactggc tcacgctagg aaccaaaagg    600

cccagcagtg atccagcccc aaaagagatc tcctttgccc cggagattac aatggacgat    660

ttcctctatc tttacgatct aggaaggaag ttcgaaggtg aaggtgacga cactatgttc    720

accactgata atgagaaggt tagcctcttc aatttcagaa agaatgctga cccacagatg    780

gttagagagg cctacgcagc aggtctcatc aagacgatct acccgagtaa caatctccag    840

gagatcaaat accttcccaa gaaggttaaa gatgcagtca aaagattcag gactaattgc    900

atcaagaaca cagagaaaga catatttctc aagatcagaa gtactattcc agtatggacg    960

attcaaggct tgcttcataa accaaggcaa gtaatagaga ttggagtctc taaaaaggta   1020

gttcctactg aatctaaggc catgcatgga gtctaagatt caaatcgagg atctaacaga   1080

actcgccgtg aagactggcg aacagttcat acagagtctt ttacgactca atgacaagaa   1140

gaaaatcttc gtcaacatgg tggagcacga cactctggtc tactccaaaa atgtcaaaga   1200

tacagtctca gaagaccaaa gggctattga gacttttcaa caaaggataa tttcgggaaa   1260

cctcctcgga ttccattgcc cagctatctg tcacttcatc gaaaggacag tagaaaagga   1320

aggtggctcc tacaaatgcc atcattgcga taaaggaaag gctatcattc aagatctctc   1380

tgccgacagt ggtcccaaag atggaccccc acccacgagg agcatcgtgg aaaaagaaga   1440

cgttccaacc acgtcttcaa agcaagtgga ttgatgtgac atctccactg acgtaaggga   1500

tgacgcacaa tcccactatc cttcgcaaga cccttcctct atataaggaa gttcatttca   1560

tttggagagg acacgctcga gtataagagc tctattttta caacaattac caacaacaac   1620

aaacaacaaa caacattaca attacattta caattaccat ggaacgagct atacaaggaa   1680
```

-continued acgatgctag ggaacaagct tatggtgaac gttggaatgg aggatcagga agttccactt 1740
ctcccttcaa acttcctgac gaaagtccga gttggactga gtggcggcta cataacgatg 1800
agacgatttc gaatcaagat aatccccttg gtttcaagga aagctggggt ttcgggaaag 1860
ttgtatttaa gagatatctc agatacgacg ggacggaaac ttcactgcac agagtccttg 1920
gatcttggac gggagattcg gttaactatg cagcatctcg atttctcggt ttcgaccaga 1980
tcggatgtac ctatagtatt cggtttcgag gagttagtgt caccatttct ggagggtcgc 2040
gaactcttca gcatctcagt gaaatggcaa ttcggtctaa gcaagaactg ctacagctta 2100
ccccagtcaa agtggaaagt gatgtatcaa gaggatgccc tgaaggtgtt gaaaccttcg 2160
aagaagaaag cgagtaagga tcctctagag tcctgcttta atgagatatg cgagacgcct 2220
atgatcgcat gatatttgct ttcaattctg ttgtgcacgt tgtaaaaaac ctgagcatgt 2280
gtagctcaga tccttaccgc cggtttcggt tcattctaat gaatatatca cccgttacta 2340
tcgtattttt atgaataata ttctccgttc aatttactga ttgtacccta ctacttatat 2400
gtacaatatt aaaatgaaaa caatatattg tgctgaatag gtttatagcg acatctatga 2460
tagagcgcca caataacaaa caattgcgtt ttattattac aaatccaatt ttaaaaaaag 2520
cggcagaacc ggtcaaacct aaaagactga ttacataaat cttattcaaa tttcaaaagt 2580
gccccagggg ctagtatcta cgacacaccg agcggcgaac taataacgct cactgaaggg 2640
aactccggtt ccccgccggc gcgcatgggt gagattcctt gaagttgagt attggccgtc 2700
cgctctaccg aaagttacgg gcaccattca acccggtcca gcacggcggc cgggtaaccg 2760
acttgctgcc ccgagaatta tgcagcattt ttttggtgta tgtgggcccc aaatgaagtg 2820
caggtcaaac cttgacagtg acgacaaatc gttgggcggg tccagggcga attttgcgac 2880
aacatgtcga ggctcagcag gacctgcata agctcttctg tcagcgggcc cactgcatcc 2940
accccagtac attaaaaacg tccgcaatgt gttattaagt tgtctaagcg tcaatttgtt 3000
tacaccacaa tatatcctgc caccagccag ccaacagctc cccgaccggc agctcggcac 3060
aaaatcacca ctcgatacag gcagcccatc agtcagatca ggatctcctt tgcgacgctc 3120
accgggctgg ttgccctcgc cgctgggctg gcggccgtct atggccctgc aaacgcgcca 3180
gaaacgccgt cgaagccgtg tgcgagacac cgcggccgcc ggcgttgtgg atacctcgcg 3240
gaaaacttgg ccctcactga cagatgaggg gcggacgttg acacttgagg ggccgactca 3300
cccggcgcgg cgttgacaga tgaggggcag gctcgatttc ggccggcgac gtggagctgg 3360
ccagcctcgc aaatcggcga aaacgcctga ttttacgcga gtttcccaca gatgatgtgg 3420
acaagcctgg ggataagtgc cctgcggtat tgacacttga ggggcgcgac tactgacaga 3480
tgaggggcgc gatccttgac acttgagggg cagagtgctg acagatgagg ggcgcaccta 3540
ttgacatttg aggggctgtc cacaggcaga aaatccagca tttgcaaggg tttccgcccg 3600
tttttcggcc accgctaacc tgtcttttaa cctgctttta aaccaatatt tataaacctt 3660
gtttttaacc agggctgcgc cctgtgcgcg tgaccgcgca cgccgaaggg gggtgccccc 3720
ccttctcgaa ccctcccggc ccgctaacgc gggcctccca tccccccagg ggctgcgccc 3780
ctcggccgcg aacggcctca ccccaaaaat ggcagcgctg gccaattcgt gcgcggaacc 3840
cctatttgtt tatttttcta aatacattca aatatgtatc cgctcatgag acaataaccc 3900
tgataaatgc ttcaataata ttgaaaaagg aagagtatgg ctaaaatgag aatatcaccg 3960
gaattgaaaa aactgatcga aaaataccgc tgcgtaaaag atacggaagg aatgtctcct 4020
gctaaggtat ataagctggt gggagaaaat gaaaacctat atttaaaaat gacggacagc 4080

-continued cggtataaag ggaccaccta tgatgtggaa cgggaaaagg acatgatgct atggctggaa 4140
ggaaagctgc ctgttccaaa ggtcctgcac tttgaacggc atgatggctg gagcaatctg 4200
ctcatgagtg aggccgatgg cgtcctttgc tcggaagagt atgaagatga acaaagccct 4260
gaaaagatta tcgagctgta tgcggagtgc atcaggctct ttcactccat cgacatatcg 4320
gattgtccct atacgaatag cttagacagc cgcttagccg aattggatta cttactgaat 4380
aacgatctgg ccgatgtgga ttgcgaaaac tgggaagaag acactccatt taaagatccg 4440
cgcgagctgt atgatttttt aaagacggaa aagcccgaag aggaacttgt cttttcccac 4500
ggcgacctgg gagacagcaa catctttgtg aaagatggca aagtaagtgg ctttattgat 4560
cttgggagaa gcggcagggc ggacaagtgg tatgacattg ccttctgcgt ccggtcgatc 4620
agggaggata tcggggaaga acagtatgtc gagctatttt ttgacttact ggggatcaag 4680
cctgattggg agaaaataaa atattatatt ttactggatg aattgtttta gctgtcagac 4740
caagtttact catatatact ttagattgat ttaaaacttc atttttaatt taaaaggatc 4800
taggtgaaga tcctttttga taatctcatg accaaaatcc cttaacgtga gttttcgttc 4860
cactgagcgt cagaccccgt agaaaagatc aaaggatctt cttgagatcc tttttttctg 4920
cgcgtaatct gctgcttgca aacaaaaaaa ccaccgctac cagcggtggt ttgtttgccg 4980
gatcaagagc taccaactct ttttccgaag gtaactggct tcagcagagc gcagatacca 5040
aatactgtcc ttctagtgta gccgtagtta ggccaccact tcaagaactc tgtagcaccg 5100
cctacatacc tcgctctgct aatcctgtta ccagtggctg ctgccagtgg cgataagtcg 5160
tgtcttaccg ggttggactc aagacgatag ttaccggata aggcgcagcg gtcgggctga 5220
acggggggtt cgtgcacaca gcccagcttg gagcgaacga cctacaccga actgagatac 5280
ctacagcgtg agctatgaga aagcgccacg cttcccgaag ggagaaaggc ggacaggtat 5340
ccggtaagcg gcagggtcgg aacaggagag cgcacgaggg agcttccagg gggaaacgcc 5400
tggtatcttt atagtcctgt cgggtttcgc cacctctgac ttgagcgtcg atttttgtga 5460
tgctcgtcag gggggcggag cctatggaaa aacgccagca acgcggcctt tttacggttc 5520
ctggcagatc ctagatgtgg cgcaacgatg ccggcgacaa gcaggagcgc accgacttct 5580
tccgcatcaa gtgttttggc tctcaggccg aggcccacgg caagtatttg ggcaaggggt 5640
cgctggtatt cgtgcagggc aagattcgga ataccaagta cgagaaggac ggccagacgg 5700
tctacgggac cgacttcatt gccgataagg tggattatct ggacaccaag gcaccaggcg 5760
ggtcaaatca ggaataaggg cacattgccc cggcgtgagt cggggcaatc ccgcaaggag 5820
ggtgaatgaa tcggacgttt gaccggaagg catacaggca agaactgatc gacgcggggt 5880
tttccgccga ggatgccgaa accatcgcaa gccgcaccgt catgcgtgcg ccccgcgaaa 5940
ccttccagtc cgtcggctcg atggtccagc aagctacggc caagatcgag cgcgacagcg 6000
tgcaactggc tccccctgcc ctgcccgcgc catcggccgc cgtggagcgt tcgcgtcgtc 6060
tcgaacagga ggcggcaggt ttggcgaagt cgatgaccat cgacacgcga ggaactatga 6120
cgaccaagaa gcgaaaaacc gccggcgagg acctggcaaa acaggtcagc gaggccaagc 6180
aggccgcgtt gctgaaacac acgaagcagc agatcaagga aatgcagctt tccttgttcg 6240
atattgcgcc gtggccggac acgatgcgag cgatgccaaa cgacacggcc cgctctgccc 6300
tgttcaccac gcgcaacaag aaaatcccgc gcgaggcgct gcaaaacaag gtcattttcc 6360
acgtcaacaa ggacgtgaag atcacctaca ccggcgtcga gctgcgggcc gacgatgacg 6420

-continued aactggtgtg gcagcaggtg ttggagtacg cgaagcgcac ccctatcggc gagccgatca 6480
ccttcacgtt ctacgagctt tgccaggacc tgggctggtc gatcaatggc cggtattaca 6540
cgaaggccga ggaatgcctg tcgcgcctac aggcgacggc gatgggcttc acgtccgacc 6600
gcgttgggca cctggaatcg gtgtcgctgc tgcaccgctt ccgcgtcctg gaccgtggca 6660
agaaaacgtc ccgttgccag gtcctgatcg acgaggaaat cgtcgtgctg tttgctggcg 6720
accactacac gaaattcata tgggagaagt accgcaagct gtcgccgacg gcccgacgga 6780
tgttcgacta tttcagctcg caccgggagc cgtacccgct caagctggaa accttccgcc 6840
tcatgtgcgg atcggattcc acccgcgtga agaagtggcg cgagcaggtc ggcgaagcct 6900
gcgaagagtt gcgaggcagc ggcctggtgg aacacgcctg ggtcaatgat gacctggtgc 6960
attgcaaacg ctagggcctt gtggggtcag ttccggctgg gggttcagca gccagcgcct 7020
gatctgggga accctgtggt tggcacatac aaatggacga acggataaac cttttcacgc 7080
ccttttaaat atccgattat tctaataaac gctcttttct cttaggttta cccgccaata 7140
tatcctgtca aacactgata gtttaaactg aaggcgggaa acgacaatct gatctaagct 7200
aggcatggaa ttccaatccc acaaaaatct gagcttaaca gcacagttgc tcctctcaga 7260
gcagaatcgg gtattcaaca ccctcatatc aactactacg ttgtgtataa cggtccacat 7320
gccggtatat acgatgactg gggttgtaca aaggcggcaa caaacggcgt tcccggagtt 7380
gcacacaaga aatttgccac tattacagag gcaagagcag cagctgacgc gtacacaaca 7440
agtcagcaaa cagacaggtt gaacttcatc cccaaaggag aagctcaact caagcccaag 7500
agctttgcta aggccctaac aagcccacca aagcaaaaag cccactggct cacgctagga 7560
accaaaaggc ccagcagtga tccagcccca aaagagatct cctttgcccc ggagattaca 7620
atggacgatt tcctctatct ttacgatcta ggaaggaagt tcgaaggtga aggtgacgac 7680
actatgttca ccactgataa tgagaaggtt agcctcttca atttcagaaa gaatgctgac 7740
ccacagatgg ttagagaggc ctacgcagca ggtctcatca agacgatcta cccgagtaac 7800
aatctccagg agatcaaata ccttcccaag aaggttaaag atgcagtcaa aagattcagg 7860
actaattgca tcaagaacac agagaaagac atatttctca agatcagaag tactattcca 7920
gtatggacga ttcaaggctt gcttcataaa ccaaggcaag taatagagat tggagtctct 7980
aaaaaggtag ttcctactga atctaaggcc atgcatggag tctaagattc aaatcgagga 8040
tctaacagaa ctcgccgtga agactggcga acagttcata cagagtcttt tacgactcaa 8100
tgacaagaag aaaatcttcg tcaacatggt ggagcacgac actctggtct actccaaaaa 8160
tgtcaaagat acagtctcag aagaccaaag ggctattgag acttttcaac aaaggataat 8220
ttcgggaaac ctcctcggat tccattgccc agctatctgt cacttcatcg aaaggacagt 8280
agaaaaggaa ggtggctcct acaaatgcca tcattgcgat aaaggaaagg ctatcattca 8340
agatctctct gccgacagtg gtcccaaaga tggaccccca cccacgagga gcatcgtgga 8400
aaaagaagac gttccaacca cgtcttcaaa gcaagtggat tgatgtgaca tctccactga 8460
cgtaagggat gacgcacaat cccactatcc ttcgcaagac ccttcctcta tataaggaag 8520
ttcatttcat ttggagagga cacgctcgag tataagagct catttttaca acaattacca 8580
acaacaacaa acaacaaaca acattacaat tacatttaca attatcgatg ggtcagtccc 8640
ttatgttacg tcctgtagaa accccaaccc gtgaaatcaa aaaactcgac ggcctgtggg 8700
cattcagtct ggatcgcgaa aactgtggaa ttgatcagcg ttggtgggaa agcgcgttac 8760
aagaaagccg ggcaattgct gtgccaggca gttttaacga tcagttcgcc gatgcagata 8820

-continued

```
ttcgtaatta tgcgggcaac gtctggtatc agcgcgaagt ctttataccg aaaggtaagt   8880

agtgtttttg gataactgag tttgcctatg attttgtatt tactgagatg tttgtcctct   8940

ttgtgcaggt tgggcaggcc agcgtatcgt gctgcgtttc gatgcggtca ctcattacgg   9000

caaagtgtgg gtcaataatc aggaagtgat ggagcatcag ggcggctata cgccatttga   9060

agccgatgtc acgccgtatg ttattgccgg gaaaagtgta cgtatcaccg tttgtgtgaa   9120

caacgaactg aactggcaga ctatcccgcc gggaatggtg attaccgacg aaaacggcaa   9180

gaaaaagcag tcttacttcc atgatttctt taactatgcc ggaatccatc gcagcgtaat   9240

gctctacacc acgccgaaca cctgggtgga cgatatcacc gtggtgacgc atgtcgcgca   9300

agactgtaac cacgcgtctg ttgactggca ggtggtggcc aatggtgatg tcagcgttga   9360

actgcgtgat gcggatcaac aggtggttgc aactggacaa ggcactagcg ggactttgca   9420

agtggtgaat ccgcacctct ggcaaccggg tgaaggttat ctctatgaac tgtgcgtcac   9480

agccaaaagc cagacagagt gtgatatcta cccgcttcgc gtcggcatcc ggtcagtggc   9540

agtgaagggc caacagttcc tgattaacca caaaccgttc tactttactg gctttggtcg   9600

tcatgaagat gcggacttac gtggcaaagg attcgataac gtgctgatgg tgcacgacca   9660

cgcattaatg gactggattg gggccaactc ctaccgtacc tcgcattacc cttacgctga   9720

agagatgctc gactgggcag atgaacatgg catcgtggtg attgatgaaa ctgctgctgt   9780

cggctttaac ctctctttag gcattggttt cgaagcgggc aacaagccga aagaactgta   9840

cagcgaagag gcagtcaacg gggaaactca gcaagcgcac ttacaggcga ttaaagagct   9900

gatagcgcgt gacaaaaacc acccaagcgt ggtgatgtgg agtattgcca acgaaccgga   9960

tacccgtccg caaggtgcac gggaatattt cgcgccactg gcggaagcaa cgcgtaaact  10020

cgacccgacg cgtccgatca cctgcgtcaa tgtaatgttc tgcgacgctc acaccgatac  10080

catcagcgat ctctttgatg tgctgtgcct gaaccgttat tacggatggt atgtccaaag  10140

cggcgatttg gaaacggcag agaaggtact ggaaaaagaa cttctggcct ggcaggagaa  10200

actgcatcag ccgattatca tcaccgaata cggcgtggat acgttagccg ggctgcactc  10260

aatgtacacc gacatgtgga gtgaagagta tcagtgtgca tggctggata tgtatcaccg  10320

cgtctttgat cgcgtcagcg ccgtcgtcgg tgaacaggta tggaatttcg ccgattttgc  10380

gacctcgcaa ggcatattgc gcgttggcgg taacaagaaa gggatcttca ctcgcgaccg  10440

caaaccgaag tcggcggctt ttctgctgca aaaacgctgg actggcatga acttcggtga  10500

aaaaccgcag cagggaggca aacaatgaat caacaactct cctggcgcac catcgtcggc  10560

tacagcctcg ggaattggga tcctctagag tcaagcagat cgttcaaaca tttggcaata  10620

aagtttc                                                           10627
```

<210> SEQ ID NO 8
<211> LENGTH: 11
<212> TYPE: DNA
<213> ORGANISM: Artificial Sequence
<220> FEATURE:
<223> OTHER INFORMATION: 3'-terminus

<400> SEQUENCE: 8

```
aagatcgaca g                                                         11
```

AGROBACTERIUM FOR TRANSIENT TRANSFECTION OF WHOLE PLANTS

CROSS-REFERENCE TO RELATED APPLICATIONS

This application is a continuation of U.S. application Ser. No. 14/386,441, which was filed on Sep. 19, 2014, has a § 371(c) date of Sep. 19, 2014, and is the U.S. National Stage of International Application No. PCT/EP2013/000994, filed Apr. 3, 2013, which designates the U.S. and was published by the International Bureau in English on Oct. 10, 2013, and which claims the benefit of European Application 12002402.1, filed Apr. 3, 2012; the contents of all of which are hereby incorporated herein in their entirety by reference.

FIELD OF THE INVENTION

The present invention relates to a process of transiently transfecting a plant or leaves on a plant. The invention also relates to a process of transiently expressing a DNA sequence of interest in a plant or in leaves on a plant. Further, the invention relates to an *Agrobacterium* strain.

BACKGROUND OF THE INVENTION

Current genetic engineering processes for agriculture are all based on stable genetic modification of crop species, demonstrated first in 1983 (Fraley et al 1983; Barton et al 1983) and commercialized since 1996. Although agriculture processes based on plant stable genetic transformation is a reality today and is a basis of successful new practices, it has multiple limitations, the main ones being very long time and high cost required for development of transgenic crops. General consensus among the companies involved in plant biotechnology is that the R&D process requires, depending on the crop species, between 8 and 16 years, and the total average development cost is estimated to be between $100 and $150 million. Because of these limitations, after more than 25 years since the discovery of a plant genetic transformation process, only a handful traits and few GM crop species have been commercialized thus far.

It is known that plant cells and whole plants can also be re-programmed transiently (i.e. without stable integration of new genetic material on a plant chromosome), and the transient processes, such as viral infections, are fast. Such transient processes could in principle allow a very fast modification of plant metabolism in favor of certain products that are of interest to the user. Such processes require a DNA or RNA vector (a virus or a bacterium), that has been engineered to effectively and safely transfect the plant. Earlier attempts to use vectors based on plant viruses have been partially successful in that they allow transfection of plants for manufacturing of high-value recombinant proteins such as certain biopharmaceuticals (Gleba et al 2007, 2008; Lico et al 2008). Use of viruses for manipulation of other traits, such as input traits (for example, herbicide resistance, Shiboleth et al 2001; Zhang and Ghabiral 2006) have been described in the literature, but virus transfection introduces so many undesired changes in the infected host that this kind of transient process is not pursued anymore for input traits. Transient processes can also be built around the ability of *Agrobacterium* species to transfer part of their Ti plasmid to eukaryotic, in particular, plant cells. Use of *Agrobacterium*-based transfection is a basis for genetic manipulations such as genetic transformation protocols and of laboratory transient transfection assays. Industrial applications of *Agrobacterium*-based transfection have also been limited to recombinant protein manufacturing, because the optimal application conditions such as vacuum infiltration of plants with bacterial suspensions cannot be used on a large scale in the field, whereas spraying aerial parts or watering plants with bacterial solutions results in a supposedly very small proportion of plant cells to be transfected, and previous studies simply did not address that specific question.

*Agrobacterium tumefaciens* and *A. rhizogenes* are broadly used in research laboratories worldwide for transient transfection and stable genetic transformation of plants. These applications are based on the ability of *Agrobacterium* to transfer genetic information to eukaryotic cells. Many of the transgenic plants cultivated today, such as soybeans, canola and cotton, have been generated through *Agrobacterium*-mediated genetic transformation. The essential difference between the transient and stable transformation is that in the process of stable transformation, *Agrobacterium*-delivered DNA is eventually integrated into a plant chromosome, and is afterwards inherited by the plant progeny. Such integration events are rare even in laboratory experiments specifically designed to provide massive contacts between plant cells and bacteria: thus for the selection of stable transformants, specific selective screening methods have to be utilized and specific plant explants (rich in meristematic tissues) selected for optimum transformation and regeneration into whole plants are employed. Subsequently, the knowledge accumulated in this science domain is of limited value to those interested in transient processes where many cells of the plant body should be affected without selection for transfected cells.

Transient transfection, on the other hand, takes into account only earlier steps of *Agrobacterium*-driven DNA delivery into a nucleus of a plant cell, along with the fact that such delivered DNA molecules can be transcribed in a nucleus even in the absence of DNA integration into a plant chromosome, such expression resulting in a transient metabolic reprogramming of a plant cell. Such reprogramming has been developed into a laboratory tool for rapid evaluation of different genetic experiments. Whereas there is considerable body of knowledge about. *Agrobacterium*-mediated DNA transfer to plant cells, that information is invariably limited to laboratory scale experiments, and thus far, there were very few attempts to develop industrial scale applications involving *Agrobacterium*, as a DNA vector.

One of the limitations of laboratory applications is the fact that *Agrobacterium*-based DNA delivery requires certain treatments that are difficult or impossible to apply in open field or on a large scale. In typical transient experiments, cultured plant cells or parts of plants (explants) are treated with an excess of bacteria to provide for maximum delivery. In typical research experiments, one is also interested in expression levels that are not economically viable if done on an industrial scale. In general, the research done in this domain has led the inventors to the conclusion that the parameters seriously affecting transient expression are those allowing for the best interaction access of agrobacteria to plant cells within a plant body. Most such studies utilize vacuum infiltration, injection into plant leaf or surfactant treatment, wounding of plant surface e.g. with razor blades, or combination thereof. In fact, the only group that is developing an *Agrobacterium*-based transfection process for commercial production of recombinant proteins that does not involve further (virus-based) amplification of the original DNA, is the group of Medicago (D'Aoust et al 2008, 2009: Vezina et al, 2009). Their process relies entirely on vacuum infiltration as a delivery method. However, because of being based on great excess of bacteria to plant cell ratio, current laboratory protocols used for transient transfection of plants do not have serious translational value, i.e. they cannot be directly replicated on an industrial level. Except in few cases (e.g. Vaquero et al, 1999, D'Aoust et al, 2008, 2009) they also have not addressed quantitatively the issue of efficiency of the transient transfection process. (Examples of such research are multiple, we provide a citation for just a few representative ones: Li et al, 1992; Liu et al, 1992; Clough and Bent, 1998; De Buck et al, 1998, 2000; Chung et al, 2000; Yang et al, 2000; Zambre et al, 2003; Wroblewski et al, 2005; Lee and Yang, 2006; Zhao et al, 2006; Shang et al, 2007; Jones et al., 2009; Li et al, 2009; De Felippes and Weigel, 2010).

One of the industrial processes being under development today is magnifection, a process that is based on vacuum-infiltration of agrobacteria into leaves of plants. The magnifection process (trademarked by Icon Genetics GmbH as magnICON® and covered by several patents/patent applications) is a simple and indefinitely scalable protocol for heterologous protein expression in plants, which is devoid of stable genetic transformation of a plant, but instead relies on transient amplification of viral vectors delivered to multiple areas of a plant body (systemic delivery) by *Agrobacterium* as DNA precursors. Such a process is in essence an infiltration of whole mature plants with a diluted suspension of agrobacteria carrying T-DNAs encoding viral RNA replicons. In this process, the bacteria assume the (formerly viral) functions of primary infection and systemic movement, whereas the viral vector provides for cell-to-cell (short distance) spread, amplification and high-level protein expression. The scale-up (industrial) version is built around fully assembled viral vectors (rather than pro-vectors requiring in planta assembly) and requires apparatuses for high-throughput *Agrobacterium* delivery to whole plants by vacuum infiltration. The process can be scaled up but it requires submersion of aerial parts of plants into bacterial suspension under vacuum (the process involves inverting plants grown in pots or in trays), a procedure that imposes limitations on the volumes of biomass that can be treated in this way, on the throughput of the process, on the ways the plants can be cultivated prior to treatment, and it also carries certain costs that limit the use of the process to high-cost products, such as recombinant biopharmaceuticals only. The magnifection process is efficient as it allows transfection of almost all leaf cells in treated plants, or approximately 50% of the total aerial plant biomass (the rest being stems and leaf petioles). The process has been optimized in many ways, see e.g. Marillonnet et al, 2005. However, the current process has been built entirely around bacterial delivery methods such as injection into a plant leaf or vacuum-infiltration (e.g. Simmons et al, 2009), wounding of leaves (Andrews and Curtis, 2005), or pouring agrobacteria into soil ('agro-drenching', Ryu et al, 2004; Yang et al, 2008), but these methods can not be applied for the mass treatment of the plants in a field (reviewed in Gleba et al, 2004, 2007, 2008; Gleba & Giritch, 2010, 2011; Lico et al, 2008; original articles of our group include Giritch et at 2006; Marillonnet et al., 2004, 2005; Santi et at, 2006; and ideologically similar papers from other research groups—Voinnet et al, 2003; Sudarshana et al, 2006; Geo et al, 2006; Mett et al, 2007; Lindbo, 2007a,b; Plesha et al, 2007, 2009; Huang et al, 2006; Regnard et al 2009; Green et al, 2009; Shoji et al, 2009).

Attempts to use *Agrobacterium* treatment on whole plants (in planta) without vacuum-infiltration have resulted in a very low number of initially transfected cells, thus greatly limiting the practical application of the process. Moreover, since no selection for transfected plant cells is done in transient transfection systems, the entire transient transfection process is of too low efficiency for large scale applications if vacuum-infiltration is to be avoided. Further, several plant species such as soybean or rape seed are difficult to transfect by *Agrobacterium*, unless specific plant tissue is used, whereby in planta transient transfection has not been achieved to a significant extent.

SUMMARY OF THE INVENTION

Departing from the prior art, it is an object of the present invention to provide an efficient process of transient in planta transfection. It is another object of the invention to provide an efficient process of transiently expressing a DNA sequence of interest in planta. Further, it is an object of the invention to provide an efficient process allowing transient plant transfection using *Agrobacterium* on a large (industrial) scale (i.e. to many plants in parallel) without the need for the application of pressure differences to introduce *Agrobacterium* into the intercellular space of plants. It is also an object to provide an *Agrobacterium* cell and strain suitable for this purpose.

These problems are solved by a process of transiently transfecting a plant or leaves on a plant, comprising contacting said plant or said leaves with a suspension comprising *Agrobacterium* cells of strain CryX deposited under accession No: DSM25686 or a derivative strain of strain CryX, wherein said derivative strain has the chromosomal background of strain CryX or said derivative strain contains the vir plasmid of strain CryX or a derivative of said vir plasmid.

Further provided is a process of transiently expressing a DNA sequence of interest in a plant, comprising contacting said plant or said leaves on said plant with a suspension comprising *Agrobacterium* cells of strain CryX deposited under accession No: DSM25686 or a derivative strain of strain CryX, wherein said derivative strain has the chromosomal background of strain CryX or said derivative strain contains the vir plasmid of strain CryX or a derivative of said vir plasmid.

The invention also provides *Agrobacterium* strain CryX having DSM accession No: DSM25686 or a derivative strain of strain CryX, wherein said derivative strain has the chromosomal background of strain CryX, or said derivative strain contains the vir plasmid of strain CryX or a derivative of said vir plasmid; or an *Agrobacterium* cell of strain CryX or of said derivative strain.

The invention also provides *Agrobacterium* cells of strain CryX having DSM accession No: DSM25686 or a derivative thereof, said cells containing a binary vector containing in T-DNA a DNA sequence of interest to be transfected into cells of a plant, wherein the binary vector may encode a VirG protein from strain CryX or a closely related VirG protein as defined below.

The invention further provides a kit comprising:

- an *Agrobacterium* cell of said strain or said derivative strain as defined above and
- a binary vector containing in T-DNA a DNA sequence of interest to be transfected into cells of a plant.

The binary vector may encode a VirG protein from strain CryX or a closely related VirG protein as defined below.

The invention also provides the vir plasmid of strain CryX and *Agrobacterium* cells having the chromosome of strain CryX.

The invention further provides an aqueous cell suspension of *Agrobacterium* strain CryX having DSM accession No: DSM25686 or a derivative strain of strain CryX (as defined herein), said suspension having a cell concentration of at most $1.1\cdot10^6$ cfu/ml of the suspension, preferably at most $4.4\cdot10^6$ cfu/ml of the suspension, and more preferably of at most $1.1\cdot10^5$ cfu/ml of the suspension.

The inventors of the present invention have found a way of strongly increasing the transient transfection efficiency of plants by *Agrobacterium*. The inventors have identified an *Agrobacterium* strain (*Agrobacterium* strain CryX) that achieves particularly high efficiency in transient transfection in planta with a wide variety of plants. Notably, strain CryX achieves much higher transient transfection efficiency in planta than other *Agrobacterium* strains that are used as a standard for plant transformation or transfection such as strain LBA4404 or EHA105 (see page 64 of Slater et al., in: Plant Biotechnology, 2$^{nd}$ edition, Oxford University Press, 2008). The inventors have further found that strain CryX achieves higher transient transfection efficiency than related *Agrobacterium* strains such as Chry5/KYRT1. Moreover, the inventors have found that a particularly high transfection efficiency can be obtained when a virG gene, notably the virG gene from *Agrobacterium* strain LBA4404 or a virG gene that is closely related to that from LBA4404 is expressed in chrysopine or succinamopine-type *Agrobacterium tumefaciens* strains.

(A) TMV-based vector capable of cell-to-cell movement: TMV(MP)-GFP (pNMD560).

(B) TMV-based vector lacking cell-to-cell movement ability: TMV(fsMP)-GFP (pNMD570).

1- *Agrobacterium tumefaciens* strain AGL1;
2- *Agrobacterium tumefaciens* strain EHA105;
3- *Agrobacterium tumefaciens* strain GV3101;
4- *Agrobacterium tumefaciens* strain ICF320;
5- *Agrobacterium tumefaciens* strain CryX;
6- *Agrobacterium tumefaciens* strain LBA4404;
7- *Agrobacterium tumefaciens* strain LBA9402.

Figure 3A:
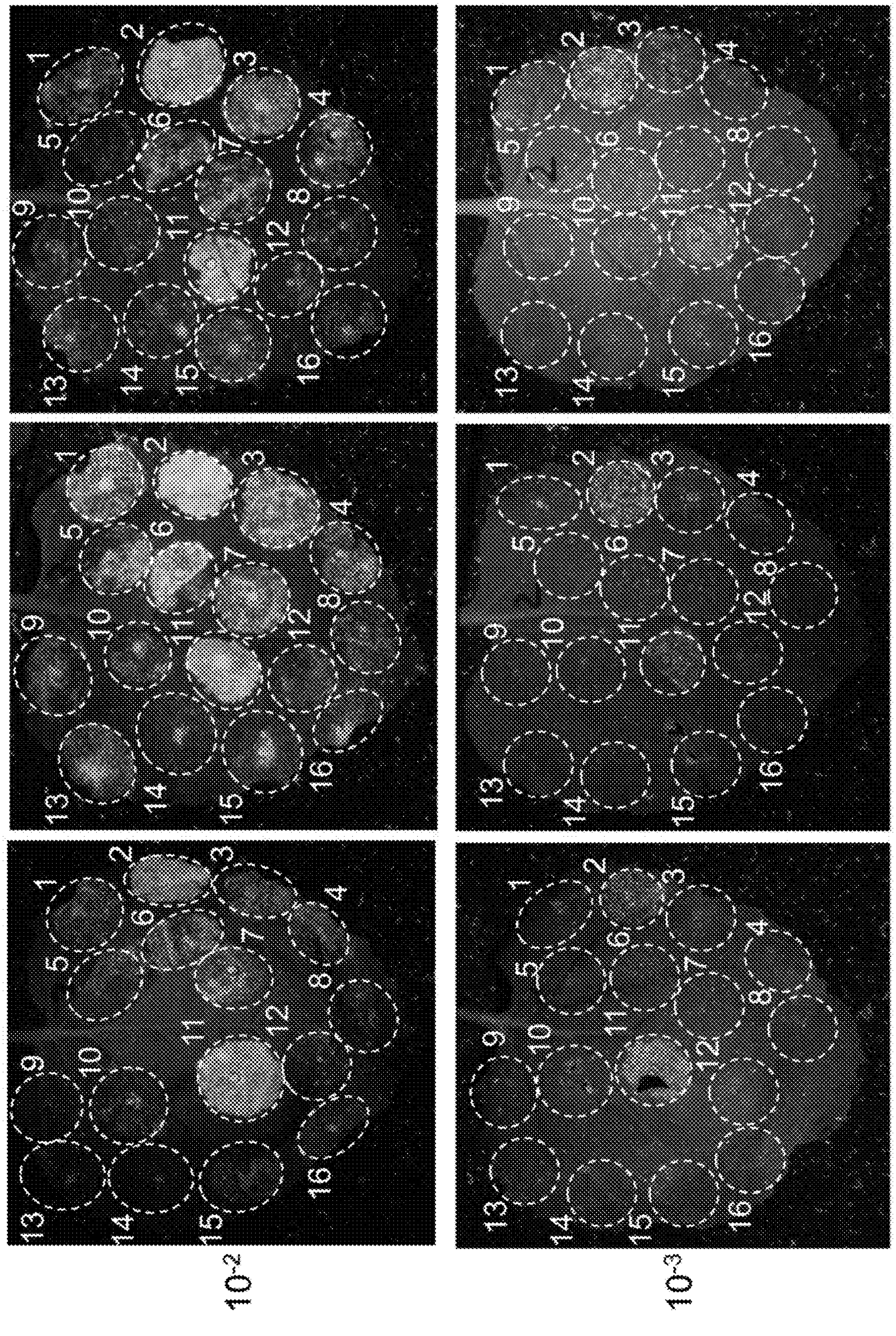
Figure 3B:
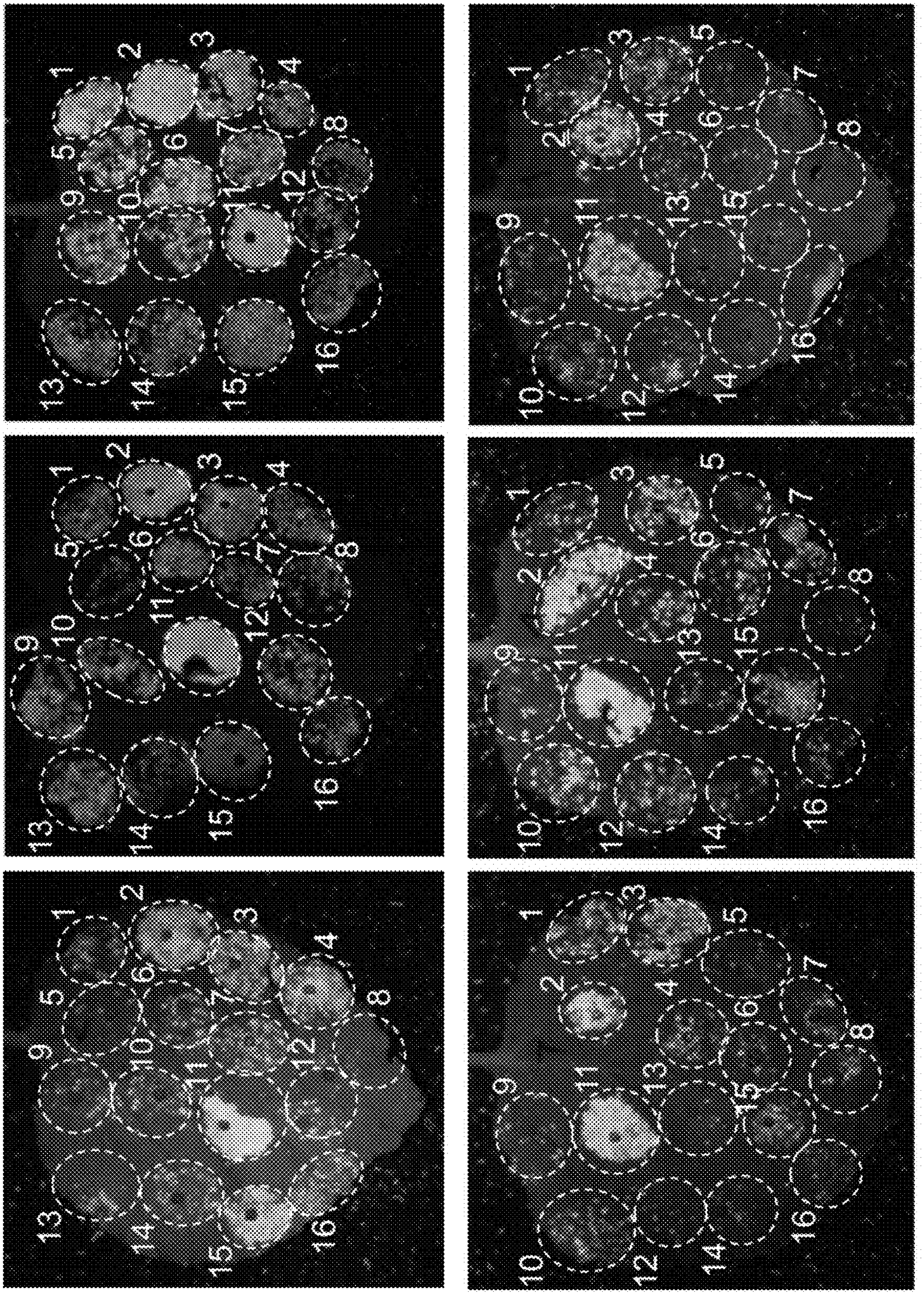

FIG. 3 demonstrates the influence of virG gene overexpression on transient transfection efficiency for AGL1, EHA105, ICF320 and GV3101 strains, virG sequences from GV3101 and LBA4404 strains carrying the N54D mutation as well as native sequence from LBA4404 strain were used for comparison. Photographs show GFP fluorescence 4 (FIG. 3A) and 6 (FIG. 3B) dpi under uv light due to TMV-based GFP expression after syringe infiltration of *Nicotiana benthamiana* leaves of the same age from 3 independent plants with diluted agrobacterial cultures as described in Example 3. Numerals $10^{-2}$, $10^{-3}$ and $10^{-4}$ indicate the factors by which the cell concentrations of the overnight agrobacterial cultures of OH=1.3 at 600 nm were reduced. Thus, the factors $10^{-2}$, $10^{-3}$ and $10^{-4}$ correspond to $10^2$-, $10^3$- and $10^4$-fold dilutions, respectively. The composition of the buffer for infiltration; 5 mM MES, pH5.3 and 10 mM $MgCl_2$. In all cases TMV-based vectors capable of cell-to-cell movement were used.

1- pNMD560 (no virG) in GV3101;
2- pNMD064 (virGN54D/GV3101) in GV3101;
3- pNMD063 (virGN54D/LBA4404) in GV3101;
4- pNMD062 (virG/LBA4404) in GV3101;
5- pNMD560 (no virG) in ICF320;
6- pNMD064 (virGN54D/GV3101) in ICF320;
7- pNMD063 (virGN54D/LBA4404) in ICF320;
8- pNMD062 (virG/LBA4404) in ICF320;
9- pNMD560 (no virG) in EHA105;
10- pNMD064 (virGN54D/GV3101) in EHA105;
11- pNMD063 (virGN54D/LBA4404) in EHA105:
12- pNMD062 (virG/LBA4404) in EHA105;
13- pNMD560 (no virG) in AGL1;
14- pNMD064 (virGN540/GV3101) in AGL1;
15- pNMD063 (virGN54D/LBA4404) in AGL1;
16- pNMD062 (virG/LBA4404) in AGL1.

Figure 4A:
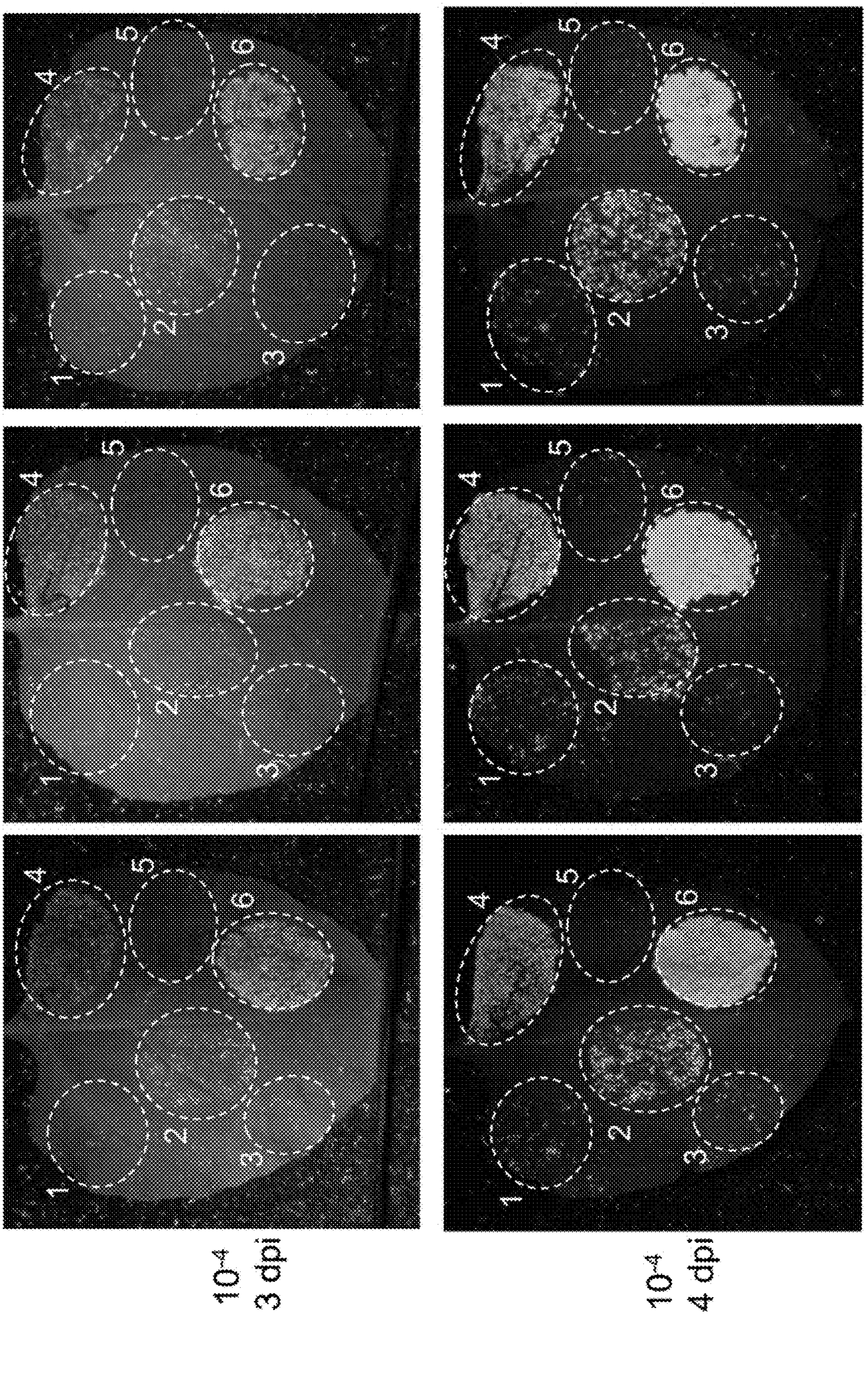
Figure 4B:
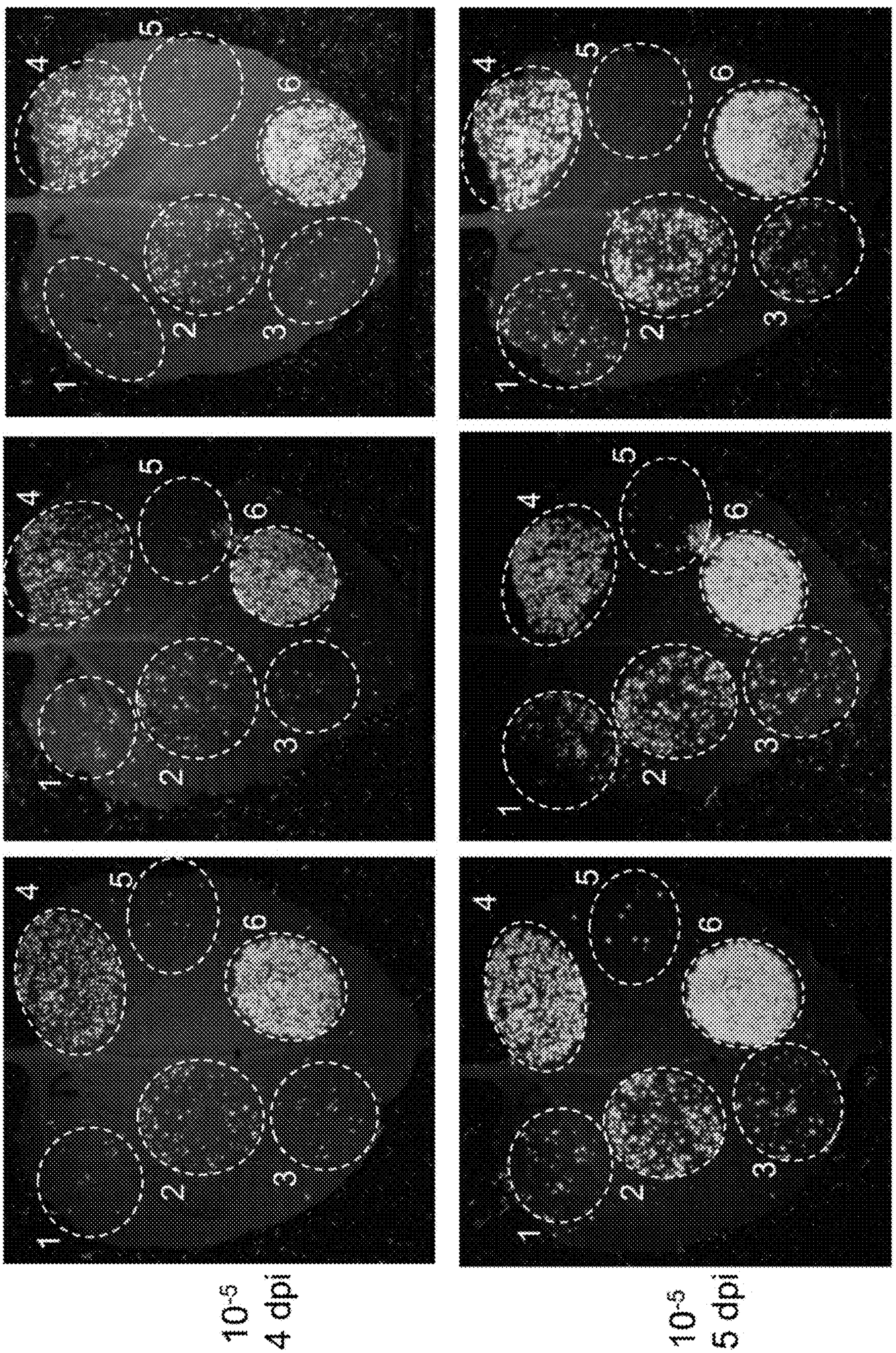

FIGS. 4A and 4B show the influence of virG gene overexpression on the transient transfection efficiency of GV3101 and CryX strains. virG sequences from GV3101 and LBA4404 strains carrying N54D mutation as well as native sequence from LBA4404 strain were used for comparison. Photographs show GFP fluorescence 3, 4 and 5 dpi under uv light due to TMV-based GFP expression after the syringe infiltration of *Nicotiana benthamiana* leaves of the same age from 3 independent plants with diluted agrobacterial cultures as described in Example 3. Numerals $10^{-4}$ and $10^{-5}$ indicate the concentration factors of the overnight agrobacterial cultures of OD=1.3 at 600 nm. The composition of the buffer for infiltration; 5 mM MES, pH5.3 and 10 mM $MgCl_2$. TMV-based vectors capable of cell-to-cell movement were used.

1- pNMD560 (no virG) in GV3101 strain;
2- pNMD064 (virGN54D/GV3101) in GV3101 strain;
3- pNMD063 (virGN54D/LBA4404) in GV3101 strain;
4- pNMD560 (no virG) in CryX strain;
5- pNMD064 (virGN54D/GV3101) in CryX strain;
6- pNMD063 (virGN54D/LBA4404) in CryX strain.

Figure 5:
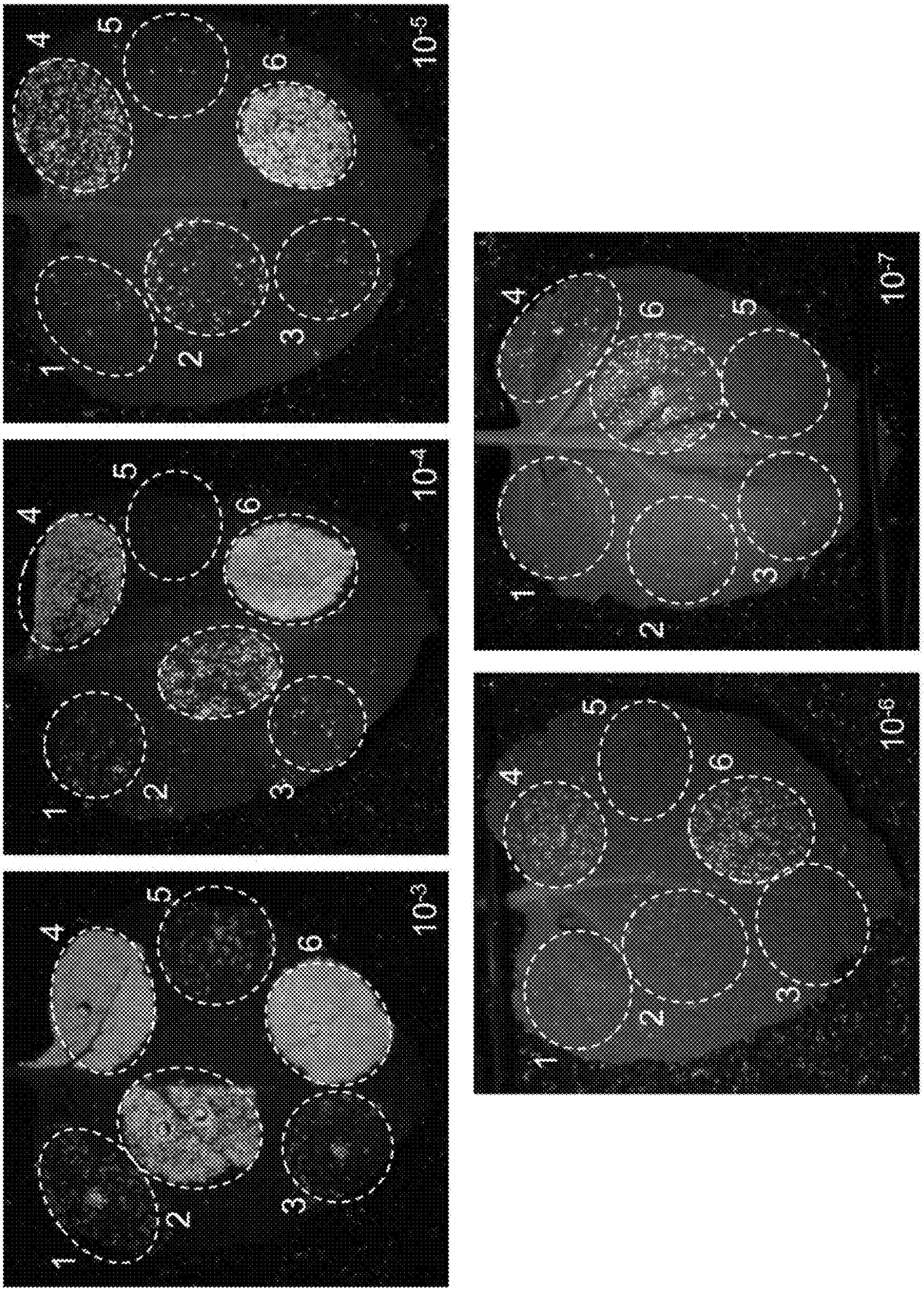

FIG. 5 shows a comparison of transient transfection efficiencies for CryX and GV3101 strains in a range of dilutions of overnight agrobacterial cultures from $10^{-3}$ to $10^{-7}$ using syringe infiltration of *Nicotiana benthamiana* leaves. Numerals $10^{-3}$, $10^{-4}$, $10^{-5}$, $10^{-6}$ and $10^{-7}$ indicate the concentration factors of the overnight agrobacterial cultures of OD=1.3 at 600 nm. These correspond to $10^3$, $10^4$, $10^5$, $10^6$ and $10^7$-fold dilutions, respectively. The composition of the buffer for infiltration: 5 mM MES, pH5.3 and 10 mM $MgCl_2$ in water. Photographs are taken at 4 dpi.
1- pNMD560 (no virG) in GV3101 strain;
2- pNMD064 (virGN54D/GV3101) in GV3101 strain;
3- pNMD063 (virGN54D/LBA4404) in GV3101 strain;
4- pNMD560 (no virG) in CryX strain;
5- pNMD064 (virGN54D/GV3101) in CryX strain;
6- pNM0063 (virGN54D/LBA4404) in CryX strain.

FIG. 6 shows the results of testing different *Agrobacterium* strains for transient transfection of soybean using spraying with suspension of agrobacterial cells. pNMD2190 construct (35S:GUS; 35S:p19 and virGN54D/LBA4404 in the plasmid backbone) was used with AGL1, EHA105, CryX and LBA4404 strains; pNMD2180 construct (35S:GUS; 35S:p19 and virGN54D/GV3101 in the plasmid backbone) was used with GV3101 and ICF320 strains. Staining of leaves for the GUS activity was performed at 11 dps.
(A) For spraying, liquid *Agrobacterium* cultures of $OD_{600}$=1.3 were diluted in the ratio 1:10 with buffer containing 5 mM MES, pH5.3; 10 mM $MgCl_2$ and 0.05% (v/v) Tween®20.
(B) For spraying, liquid *Agrobacterium* cultures of $OD_{600}$=1.3 were diluted in ratios 1:10, 1:100 and 1:1000 with buffer containing (5 mM MES, pH5.3; 10 mM $MgCl_2$ and 0.05% (v/v) Tween®20) supplemented with silicon carbide particles of size 800 in the concentration 0.3% (w/v).

Figure 7:
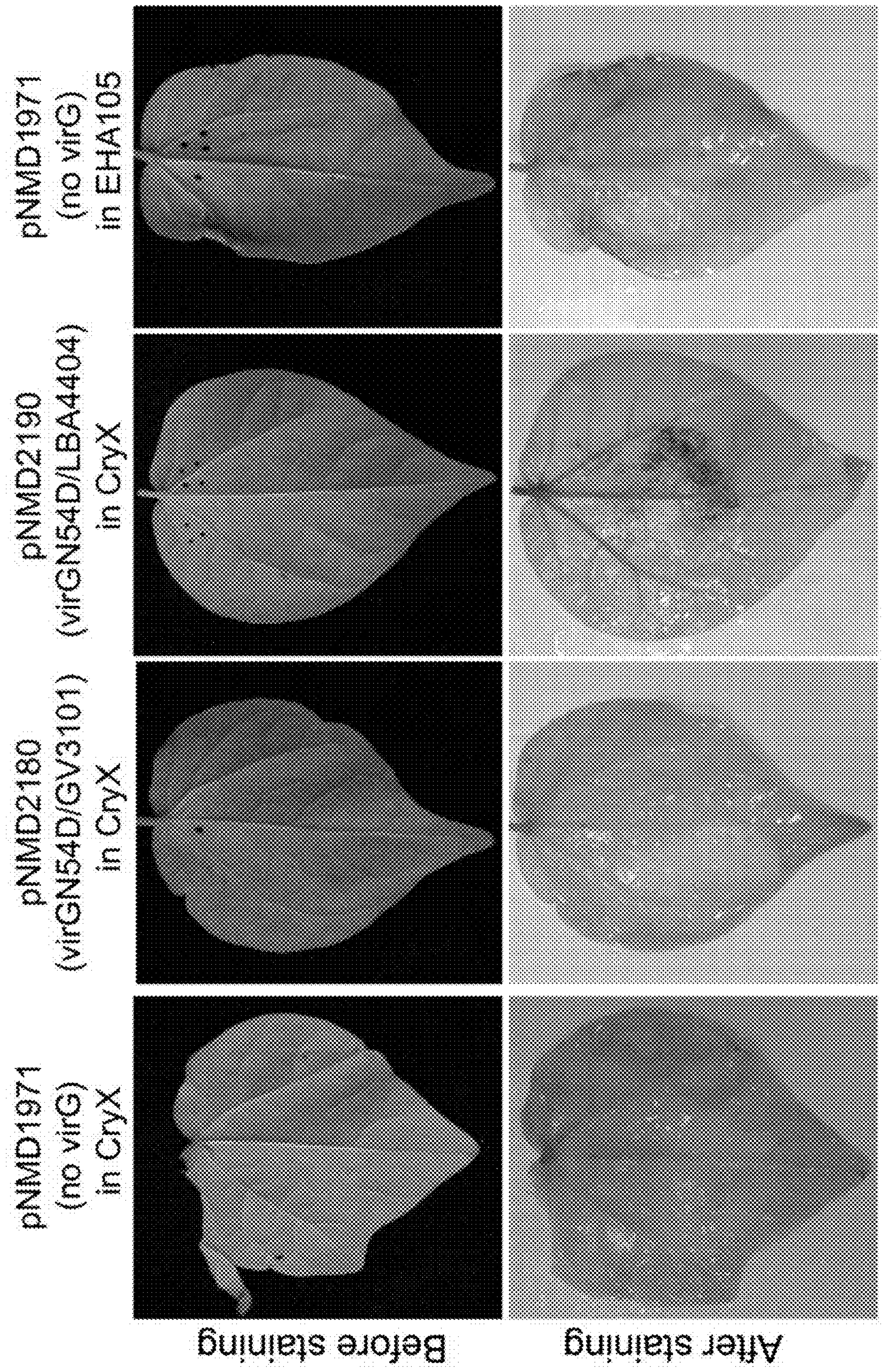

FIG. 7 shows test results of CryX and EHA105 strains for transient transfection of cotton *Gossipium hirsutum* L. using spraying with suspension of agrobacterial cells. For spraying, liquid *Agrobacterium* cultures of $OD_{600}$=1.3 were diluted in the ratio 1:10 with buffer containing 5 mM, MES pH5.3; 10 mM $MgCl_2$ and 0.25% (v/v) Silwet L-77. For testing, constructs pNMD1971 (35S:GUS; 35S:p19), pNMD2180 (35S:GUS; 35S:p19 and virGN54D/GV3101 in the plasmid backbone) and pNMD2190 (35S:GUS; 35S:p19 and virGN54D/LBA4404 in the plasmid backbone) were used. GUS activity test was performed at 6 dps.

Figure 8:
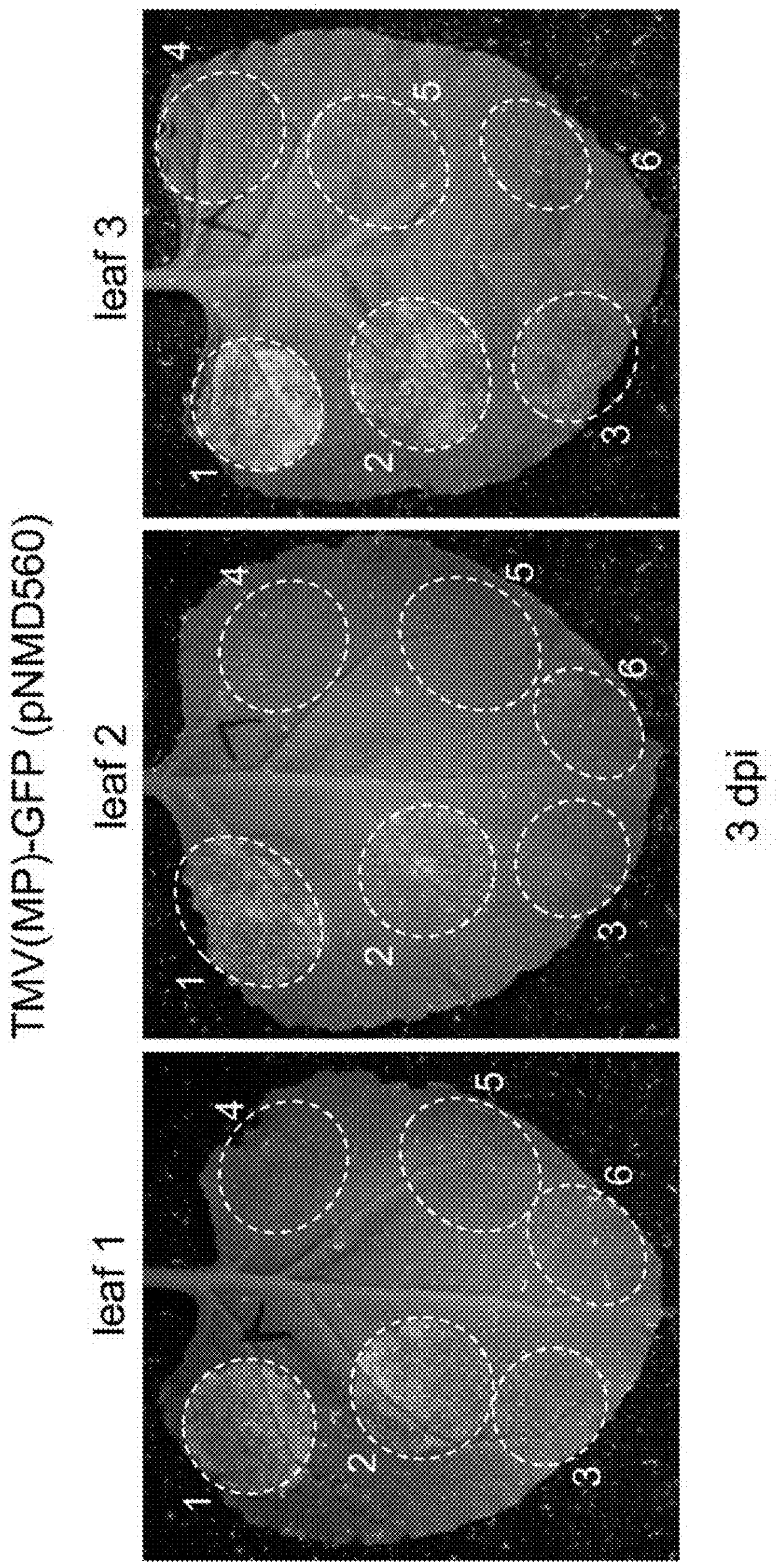

FIG. 8 shows a comparison of two accessions of *Agrobacterium tumefaciens* Chry5/KYRT1 strains received from different laboratories using a TMV-based vector capable of cell-to-cell movement (TMV-GFP, pNMD560 vector). Photographs show GFP fluorescence 4 dpi (days post infection) under uv tight due to TMV-based GFP expression after syringe infiltration of *Nicotiana benthamiana* leaves with diluted overnight agrobacterial cultures of OD=1.3 at 600 nm as described in Example 8. The strain obtained from the laboratory of Dr. G. Collins in the University of Kentucky (Lexington, USA) is infiltrated on the right-hand side of each leaf. The accession from the Institute of Cell Biology and Genetics Engineering (ICBGE, Kiev, Ukraine), is infiltrated on the left-hand side of each leaf. The composition of the buffer for infiltration is 5 mM MES, pK5.5 and 10 mM $MgSO_4$. Each infiltration was performed in triplicate using three independent leaves of the same plant.
1- ICBGE accession, concentration factor $10^{-1}$ (10-fold dilution);
2- ICBGE accession, concentration factor $10^{-2}$;
3- ICBGE accession, concentration factor $10^{-3}$;
4- Kentucky University accession, concentration factor $10^{-1}$;
5- Kentucky University accession, concentration factor $10^{-2}$;
6- Kentucky University accession, concentration factor $10^{-3}$.

DETAILED DESCRIPTION OF THE INVENTION

In the present invention, a particular class of *Agrobacterium tumefaciens* strains is used for transient transfection of plants such as leaves on a plant. This class of *Agrobacterium* comprises *A. tumefaciens* strain CryX and derivative strains thereof as defined below. Strain CryX was deposited with DSMZ-Deutsche Sammlung von Mikroorganismen und Zellkulturen GmbH, Inhoffenstraβe 7B, 38124 Braunschweig, Germany on Feb. 23, 2012 under the Budapest Treaty. Accession number DSM25686 has been assigned to it. Strain CryX has a chromosomally integrated rifampicin resistance.

Strain CryX is related to the Chrysanthemum morifolium-derived *Agrobacterium* strain Chry5 that has been identified by Busch & Puepke in 1991. It has been shown in their paper that the strain is a biotype I by traditional biotype tests and that it produces tumors on at least 10 plant species. It has been characterized as unusual because of its ability to form efficiently large tumors on soybean (*Glycine max*) and for this reason, it has been subsequently further characterized in a number of papers by various groups. Chry5 is unable to utilize octopine or mannopine as a carbon source; instead it is able to catabolize a single isomer each of nopaline and succinamopine, at the same time it is insensitive to agrocin 84 (Busch & Puepke, 1991). In addition, Chry5-strain-induced tumors produce a family of Amadori-type opines that includes deoxyfructosyl glutamine (Dfg) and its lactone, chrysopine (Chy) (Palanichelvam et al., 2000). The isolates of Chry5 have been shown to contain at least two plasmids, one with a homology with pTiB6. Torisky et at (1997) have partially disarmed the strain by removing approx. 16.5-kb segment from the 285-kb Ti plasmid of Chry5, including approx. 4 kb of the oncogenic T-DNA, through homologous recombination. This deletion mutant, named KYRT1, has been shown to be an efficient vector organism, and this partially disarmed derivative of Chry5 has since been used by some researchers. More recently, Palanichelvamet et al. (2000) have developed a fully disarmed derivative.

In research that led to the present invention, the inventors have initially tested two accessions of Chry5/KYRT1 received from different laboratories. The strain obtained from the laboratory of Dr. G. Collins (Torisky et al., 1997) did not show any superiority over standard comparator strains EHA105 and GV3101 in our transient studies and was excluded from further studies. An accession from the Institute of Cell Biology and Genetics Engineering (Kiev, Ukraine), on the other hand, has been found to be unusually active in its transient transfection and expression efficiency and has been used in the present invention. This latter accession was deposited under the Budapest treaty in the official depository DSMZ-Leibniz-Institut Deutsche Sammlung von Mikroorganismen und Zelikulturen GmbH, Braunschweig, Germany under the name CryX, to reflect the fact that there is no clear provenance information on it.

The original and subsequent papers have characterized the Chry5 strain in more detail. These studies aimed at standard characterization of molecular biology and genetics of the strain, as well as its comparative ability to induce tumors, to cause genetic transformation of different plant species, as well as its ability to cause transient expression in *Agrobacterium*-treated explants. Results of these studies are briefly summarized below.

Methods of Comparison Used to Characterize *Agrobacterium tumefaciens* Chry5

1. Data on Oncogenicity

In the original paper of Bush & Puepke (1991), it has been established that the Chry5 strain is able to cause tumors on 10 plant species representing 7 plant families. The test involved semi-quantitative evaluation of the number of plants with tumors caused by this strain versus the common laboratory strain B6. There were no significant differences in tumorigenicity between the strains in 6 out of 9 species (beets, kalanchoe, marigold, sunflower, tobacco and tomato). On collard, Chry5 has been approx. two times more efficient, and on soybean—approx. three times more efficient, whereas on pea, it was somewhat less efficient than B6. Torisky et al, (1997) provided additional data on tumor formation on stems of tobacco and tomato; in this study, the Chry5 strain and its partially disarmed derivative KYRT1 have been compared with two other *Agrobacterium* strains often used in transformation studies, including A281, a succinamopine-type strain containing Bo542 Ti plasmid in the C58 chromosomal background and its disarmed derivative EHA105 strain. It has been shown in that study that whereas the original Chry5 and the other succinamopine strain used, A281, are both highly tumorigenic, the partially disabled derivative KYRT1 and EHA105 were not active.

2. Data on Transformation Efficiency using Partially Disabled and Fully Disabled Strains Torisky et al. (1997) demonstrated that KYRT1 successfully transfers the beta-glucuronidase (GUS) gene into tobacco leaf explants, producing GUS-expressing callus which could be regenerated into viable plants. In these experiments, the transformation efficiency of KYRT1 strain was approximately the same as was shown for EHA105. Grant et al. (2003) found the KYRT1 strain to be on average threefold more efficient than AGL 1 for producing transgenic plants of pea using for evaluation cotyledonary explants of three different plant genotypes.

In the work of Palanichelvam et al. (2000), it has been shown that KYRT1 derivative is only partially disarmed and contains all of oncogenic T-right and the fragment of T-left regions. A Chry5 derivative with completely disarmed Ti plasmid, pKPSF2 (Palanichelvam et al., 2000), was, however, less efficient for the stable transformation of soybean, as the KYRT1 strain retains some hormonal effect on plant explants enhancing somatic embryogenesis in soybean (Ko et al., 2004), 3. Data Characterizing Transient Activity Again, Torisky et al (1997) were the first to study transient expression of β-glucuronidase transgene caused by the Chry5 derivative KYRT1 by using a quantitative assay of GUS expression in cotyledonary node explants of soybean. These data indicated that KYRT1 derivative was approx. 2.5 times more efficient in causing transient expression when compared to EHA105 or GV3850. KYRT1 was on average 2.8-fold more efficient than EHA105 and C58C1 for producing transient β-glucuronidase (GUS) gene (gus) expression on cotyledonary petioles of a recalcitrant legume plant, lentil (*Lens culinaris* M.) (Akcay et al., 2009), Akbulut et al. (2008) have measured GUS activity in explants derived from wounded seedlings after treatment with KYRT1 and two other common vectors, C58C1 and EHA105. The quantitative evaluation of GUS expressing spots has shown that after 16 hours of imbibition, there are no statistically significant differences between KYRT1 and C58C1, and after 40 hours, KYRT1 is better by ca. 50%, but only in one of two measurement points.

Interpretation of the above mentioned data in its entirety is difficult because different authors used different plant species, different plant explants, different strains of *Agrobacterium* for comparison, and have made their conclusions based on three different activity methods: tumorigenic activity, efficiency of genetic transformation and efficiency of transient expression. The process of interaction of a plant cell and an *Agrobacterium* is very complex, and it involves transfer of T-DNA-protein complex, transfer of proteins such as VirE2 (via a separate secretion system), transient expression of T-DNA genes in a plant cell, hormonal effect of expressed genes, integration of some T-DNA molecules into a plant chromosomal DNA, etc. Any of these intermediate processes can influence the end result; therefore, data on tumorigenicity and on transformation efficiency gives no information with regard to the efficiency of T-DNA transfer and transient expression. The presented data on transient activity are, on the other hand, limited and the slight differences observed are inconclusive or not practically relevant.

A major difference in the processes and strains described herein and the methods used in the prior art described above is the different biology of the plant material used for transient expression studies. Whereas all previous authors used in vitro cultured or excised plant explants rich in meristematic tissues (the ultimate goal being ability to transform a plant cell and to regenerate a whole plant from said transgenic cell), such as excised embryo, parts of young seedlings, etc., the present invention relates to transient transfection of intact, developed plants which interact with *Agrobacterium* differently. On entire plants, agrobacteria enter the leaf via stomata (that is absent in other organs and in meristematic tissues) and not via wounds on plant explants. As mentioned before, all authors without exception were using high bacteria densities when treating plant explants.

Strain CryX of the present invention contains a vir plasmid that is at least partially disarmed. "Disarmed" means that the vir plasmid and its host *Agrobacterium* is not oncogenic, i.e. it does not insert oncogenes or genes for the production of opines into plant cells, either because it does not contain such genes or it cannot transfer such genes. A vir plasmid comprises the vir genes (virulence genes) required for T-DNA transfer into plant cells. Vir genes and their functions in T-DNA transfer are known in the art and are e.g. summarized in the book of Slater et al., Plant Biotechnology, $2^{nd}$ edition; Oxford University Press, 2008; see also Hellens et al., Trends in Plant Science 5 (2000) 446-451.

Strain CryX of the present invention is a binary strain, i.e. the vir genes required for transfer of T-DNA into plant cells and the T-DNA are on separate plasmids (see e.g. the book of Slater et al and the article of Hellens et al. regarding binary *Agrobacterium* strains and vector systems). In the context of a binary *Agrobacterium* strain, the plasmid containing the vir genes is referred to herein as "vir plasmid" or "vir helper plasmid". The plasmid containing the T-DNA to be transfected is referred to as "vector" or "binary vector". The term "strain" or "*Agrobacterium* strain" relates to components of the *Agrobacterium* other than the binary vector. Thus, herein, a binary *Agrobacterium* strain not containing a binary vector and after introduction of a binary vector are referred to by the same strain name. Deposited strain CryX contains a vir plasmid, but does not contain a binary vector.

The invention also relates to derivative strains of strain CryX. In an embodiment (i), a derivative strain of strain CryX has the chromosomal background of strain CryX. It may have the same chromosome as CryX in another embodiment (ii), a derivative strain of strain CryX contains the vir plasmid of strain CryX. In a further embodiment (iii), a derivative strain of strain CryX contains a derivative of the vir plasmid of strain CryX, and may have the chromosome of strain CryX. In embodiment (ii), the strain is a binary strain and is used in the processes of the invention after introduction of a binary vector containing a T-DNA of interest. In embodiments (i) and (iii), the strains may be binary strains. If they are binary strains, they are used in the processes of the invention after introduction of a binary vector containing a T-DNA of interest. Alternatively, in embodiments (i) and (iii), the T-DNA to be transferred into plant cells in the processes of the invention may be inserted into the vir plasmid, such that the vir genes and the T-DNA are present on one and the same plasmid molecule. However, it is generally more convenient and thus preferred to use binary strains.

The term "chromosomal background" is a standard term in the art of *Agrobacterium* transformation or transfection (cf. Hellens et al., Trends in Plant Science 5 (2000) 446-451). It relates to genetic material of said *Agrobacterium* strain other than the Ti plasmids, vir helper plasmids and binary vectors. In one embodiment, a derivative strain of strain CryX has the same chromosome as strain CryX. A derivative strain having the chromosomal background of strain CryX may differ from CryX, for example, in the vir plasmid compared to the vir plasmid of CryX. Thus, a derivative strain of strain CryX may contain a vir plasmid that is a derivative of the vir plasmid of strain CryX.

Whether a given *Agrobacterium* strain that has a chromosome that is non-identical to that of strain CryX has a chromosomal background of strain CryX can be tested experimentally by comparing the T-DNA transfer efficiency (or transfection efficiency) from a T-DNA-containing binary vector of strain CryX with the strain to be tested that contains the vir plasmid of CryX and the same binary vector. The strain to be tested is considered having the chromosomal background of CryX if it achieves at least 70%, preferably at least 80% of the T-DNA transfer efficiency of strain CryX. Transfection efficiencies can be determined as described in Example 2. Alternatively, transfection efficiencies can be determined as in Example 2 but using a binary vector encoding a TMV-viral replicon not capable of cell-to-cell movement such as pNMD570. T-DNA transfer efficiency can also be determined by protoplast counting as described in WO 2005049839. In one embodiment, the chromosome of an *Agrobacterium* strain having the chromosomal background of strain CryX has a chromosome that is the same in base sequence as that of strain CryX.

A derivative of the vir plasmid of strain CryX achieves, when present in *Agrobacterium* cells having the same chromosome as strain CryX, a similar efficiency of T-DNA transfer into plant cells from a T-DNA-containing binary vector present in these cells. For this purpose, the derivative vir plasmid has a vir region sufficiently similar to that of the vir plasmid of strain CryX. The derivative vir plasmid may encode the virG protein of strain CryX or a closely related virG protein. Preferably, the derivative vir plasmid contains the virG gene of strain CryX. In one embodiment, the derivative vir plasmid contains genes encoding at least two of the following virulence proteins of CryX: VirA, VirG, VirB1-BirB11, VirC1, VirD1, VirD2, VirD4, VirE1, VirE2, VirF and VirJ. In a further embodiment, a derivative vir plasmid contains at least the genes encoding the following virulence proteins of CryX: VirA, VirG, VirD2, and VirE2. In a further embodiment, a derivative vir plasmid contains the entire vir region, i.e. all vir genes of the vir plasmid of strain CryX. The derivative vir plasmid may differ in the plasmid backbone from the vir plasmid of CryX. For example, the derivative vir plasmid may have a different or additional selective marker gene or may have deleted further nucleic acid portions from outside the vir region. In one embodiment, the derivative vir plasmid is pKYRT1 (U.S. Pat. No. 5,929,306), notably if the derivative strain has the same chromosome as CryX.

Whether a given vir plasmid is a derivative vir plasmid in the sense of the present invention may be tested experimentally by comparing the T-DNA transfer efficiency from a T-DNA-containing binary vector between *Agrobacterium* of strain CryX and *Agrobacterium* having the chromosome of strain CryX but the vir plasmid to be tested under otherwise identical conditions. In one embodiment, the *Agrobacterium* containing a derivative plasmid according to the invention achieves at least 70%, preferably at least 80%, more preferably at least 90% of the TDNA transfer efficiency of strain CryX. Transfection efficiencies can be determined as described in Example 2 and as mentioned above.

"Closely related virG protein" to the virG protein of CryX means a virG protein that differs from the virG protein of CryX in at most 3 non-conservative amino acid substitutions or in at most 6, preferably at most 3 conservative amino acid substitutions. The non-conservative amino acid substitutions may be at positions corresponding to positions 6, 7 or 106 of the amino add sequence of SEQ ID NO: 1 which is the VirG protein from *Agrobacterium* strain LBA4404, all other amino acid residues being as in SEQ ID NO:1. In addition, the closely related virG protein may have an asparagine to aspartate substitution at the position corresponding to position 54 of SEQ ID NO: 1. The conservative amino acid substitutions may be at positions 6, 7 and/or 106 of the amino acid sequence of SEQ ID NO: 1.

Herein, conservative substitutions are substitutions of amino acid residues within each of the following four groups:

Ala, Pro, Gly, Glu, Asp, Gin, Asn, Ser, Thr
Val, Ile, Leu, Met
Lys, Arg, His
Phe, Tyr, Trp

All other amino acid residue substitutions are considered non-conservative.

Herein, a "T-DNA of interest" is a DNA containing, between T-DNA left and right border sequences, a DNA sequence of interest. A T-DNA of interest may be present or may have been incorporated by sub-cloning into a vir plasmid such as the vir plasmid of strain CryX. In the processes of the invention, it is preferred to use a binary vector system. Therefore, a T-DNA of interest is preferably present or will have been incorporated into into a binary vector.

The binary vector to be used in the present invention is a DNA molecule comprising a DNA sequence of interest to be transfected into plant cells. The DNA sequence of interest typically encodes a protein or an RNA to be expressed in cells of the transfected plants. The binary vector is generally produced by inserting or cloning a nucleic acid construct containing the DNA sequence of interest into a cloning site within T-DNA of a precursor binary vector, as generally done in *Agrobacterium*-mediated plant transfection. After said insertion, the nucleic acid construct is flanked by T-DNA left and right border sequences for allowing transfection of said plant with said T-DNA. In the T-DNA of the binary vector, the DNA sequence of interest is present such as to be expressible in plant cells. For this purpose, the DNA sequence of interest is, e.g. in said nucleic acid construct, typically under the control of a promoter active in plant cells. Examples of the DNA sequence of interest are a DNA sequence encoding a DNA viral replicon or an RNA viral replicon or a gene to be expressed. The gene may encode an RNA of interest or a protein of interest to be expressed in cells of the plant(s). Also the viral replicons typically encode an RNA or a protein of interest to be expressed in plants. The DNA construct may comprise, in addition to the DNA sequence of interest, other sequences such as regulatory sequences for expression of the DNA sequence of interest. Binary vectors usable in the invention are known to the skilled person, e.g. from the references cited in the introduction or from text books on plant biotechnology such as Slater, Scott and Fowler, Plant Biotechnology, second edition, Oxford University Press, 2008. The binary vector typically has an antibiotic resistance gene for allowing selection in bacteria such as *E. coli.*

For increasing transfection efficiency, the binary vector may comprise, outside the T-DNA, a virG gene expressible in said *Agrobacterium* strain. Alternatively, an additional plasmid may be inserted into said *Agrobacterium* strain, whereby said additional plasmid contains a virG gene expressible in said *Agrobacterium* strain (Pazour et al., Proc. Natl. Acad. Sci. USA 88 (1991) 6941-6945). The virG gene preferably encodes a VirG protein from *Agrobacterium tumefaciens* strain LBA4404 or a closely related VirG protein. Further, the VirG protein may have the N54D mutation at the position corresponding to position 54 of SEQ ID NO: 1, i.e. the VirG protein from *A. tumefaciens* strain LBA4404. The N54D mutation in a VirG protein from another *Agroabacterium* strain was described by Jung et al., Current Microbiology 49 (2004) 334-340.

The closely related VirG protein may be (i) a protein comprising at least 235, preferably at least 239 consecutive amino acids of the amino acid sequence of SEQ ID NO: 1 or of the amino acid sequence of the N54D mutant of the amino acid sequence of SEQ ID NO: 1; or (ii) a protein comprising an amino acid sequence having not more than 3 non-conservative amino acid substitutions and not more than 10 conservative amino acid substitutions of the amino acid sequence of SEQ is NO: 1 or the N54D mutant thereof; or (iii) a protein comprising an amino acid sequence having not more than 20, preferably not more than 10, conservative amino acid substitutions of the amino acid sequence of SEQ ID NO: 1 or the N54D mutant thereof.

In items (ii) and (iii), said protein preferably has an asparagine or aspartate residue at the position corresponding to position 54 of SEQ ID NO: 1

Possible positions for the conservative amino acid substitutions in the embodiments mentioned above are positions 6, 7, 18, 35, 38, 42, 44, 66, 69, 73, 81, 86, 89, 97, 106, 107, 122, 124, 133, 135, 143, 147, 150, 165, 188, 208, 212, 213, 232, 235, and 238 of SEQ ID NO: 1, while amino acid residues at other positions are those as in SEQ ID NO:1. Possible positions for non-conservative substitutions are positions 6, 7 and 106 of the amino acid sequence of SEQ ID NO: 1.

In embodiments wherein strong expression of a protein or RNA is desired or wherein accumulation of viral nucleic acids to high amounts in cells of said plant and possible negative effects on plant health is not a concern, the nucleic acid construct or DNA sequence of interest may encode a replicating viral vector that can replicate in plant cells. In order to be replicating, the viral vector contains an origin of replication that can be recognized by a nucleic acid polymerase present in plant cells, such as by the viral polymerase expressed from the replicon. In case of RNA viral vectors, the viral replicons may be formed by transcription, under the control of a plant promoter, from the DNA construct after the latter has been introduced into plant cell nuclei. In case of DNA viral replicons, the viral replicons may be formed by recombination between two recombination sites flanking the sequence encoding the viral replicon in the DNA construct, e.g. as described in WO00/17365 and WO 99/22003. If viral replicons are encoded by the DNA construct, RNA viral replicons are preferred. Use of DNA and RNA viral replicons has been extensively described in the literature at least over the last 15 years. Some examples are the following patent publications by Icon Genetics: WO2008028661, WO2007137788, WO2006003018, WO2005071090, WO2005049839, WO02097080, WO02088369, and WO02068664. An example of DNA viral vectors are those based on geminiviruses. For the present invention, viral vectors or replicons based on plant RNA viruses, notably based on plus-sense single-stranded RNA viruses are preferred. Examples of such viral vectors are tobacco mosaic virus (TMV) and potexvirus X (PVX) used in the examples. Potexvirus-based viral vectors and expression systems are described in EP2061890. Many other plant viral replicons are described in the patent publications mentioned above.

When performing the process of the invention, the binary vector containing in T-DNA the DNA sequence of interest may be introduced into the *Agrobacterium* strain containing the vir plasmid or its derivative by conventional methods such as electroporation. A culture of the strain containing the binary vector is then grown in suitable media, typically in the presence of a selective agent for selecting *Agrobacterium* cells containing the binary vector, and, optionally, subcultured to produce the desired amount of an aqueous suspension comprising the *Agrobacterium* cells. The obtained suspension may be diluted to the desired concentration with water, a suitable buffer or media and be used for transfecting a plant or leaves on the plant. Alternatively, if the T-DNA is part of the vir plasmid, the T-DNA containing vir plasmid is introduced into *Agrobacterium* by conventional methods such as electroporation and further treated as described for the binary system.

In the processes of the invention, in planta transfection is used. In planta means that the processes are performed on whole living plants after the seedling stage, preferably on fully developed plants, rather than on excised or in vitro cultivated plant tissues or organs. Preferably, the process is applied to many plants in parallel such as plants growing on a field.

Said plants may be contacted with the suspension of *Agrobacterium* cells by infiltration with or without application of vacuum. In one embodiment, notably when applied to multiple plants in parallel, the plants may be contacted with the suspension by spraying. The aqueous suspension used in the processes of the invention may have a concentration of *Agrobacterium* cells of at most $1.1 \cdot 10^9$ cfu/ml, which corresponds approximately to an *Agrobacterium* culture in LB-medium of an optical density at 600 nm of 1. Due to the high transfection efficiency achieved in the invention, much lower concentrations may, however, be used, which allows treatment of many plants such as entire farm fields without the need for huge fermenters for *Agrobacterium* production. Thus, the concentration is preferably at most $2.2 \cdot 10^7$ cfu/ml, more preferably at most $1.1 \cdot 10^7$ cfu/ml, more preferably at most $4.4 \cdot 10^6$ cfu/ml, in one embodiment, the concentration is at most $1.1 \cdot 10^6$ cfu/ml of the suspension. In a further embodiment, the concentration is at most $4.4 \cdot 10^5$ cfu/ml of the suspension, and in a further embodiment, the concentration is at most $1.1 \cdot 10^5$ cfu/ml of the suspension For avoiding determination of cell concentrations in terms of cfu/ml, concentrations of agrobacterial suspensions are frequently assessed by measuring the apparent optical density at 600 nm using a spectrophotometer. Herein, the concentration of $1.1 \cdot 10^7$ cfu/ml corresponds to a calculated optical density at 600 nm of 0.01, whereby the calculated optical density is defined by a 100-fold dilution with water or buffer of a suspension having an optical density of 1.0 at 600 nm. Similarly, the concentrations of $4.4 \cdot 10^6$ cfu/ml, $1.1 \cdot 10^6$ cfu/ml, $4.4 \cdot 10^5$ cfu/ml and $1.1 \cdot 10^5$ cfu/ml of the suspension correspond to a calculated optical density at 600 nm of 0.004, 0.001, 0.0004, and 0.0001 respectively, whereby the calculated optical densities are defined by a 250-fold, 1000-fold, 2600-fold, or 10000-fold, respectively, dilution with water or buffer of a suspension having an optical density of 1.0 at 600 nm.

Thus, in a particularly preferred embodiment, the invention provides a process, and *Agrobacterium* cell suspension therefor, of transiently expressing a DNA sequence of interest in a plant, comprising contacting said plant or said leaves on said plant with a suspension comprising *Agrobacterium* cells of strain CryX or a derivative strain of strain CryX, wherein said derivative strain has the chromosomal background of strain CryX or said derivative strain contains the vir plasmid of strain CryX or a derivative of said vir plasmid, wherein said suspension has any of the maximum *Agrobacterium* cell concentrations mentioned in any one of the preceding two paragraphs. In this embodiment, the *Agrobacterium* strain is preferably a binary strain containing a binary vector comprises a virG gene expressible in said strain CryX or said derivative strain. Said virG gene may encodes a VirG protein from *Agrobacterium tumefaciens* strain LBA4404 of SEQ ID NO: 1, or is an N54D mutant of the VirG protein encoded by the virG gene from *A. tumefaciens* strain LBA4404.

It is possible to include an abrasive into the suspension for increasing the transfection efficiency. The abrasive is a particulate material that is essentially insoluble in the aqueous suspension of *Agrobacterium* cells. The abrasive is believed to weaken, notably if used together with a wetting agent, the surface of plant tissue such as leaves, and thereby facilitates penetration of *Agrobacterium* cells into the intercellular space of plant tissue. Regarding possible abrasive usable in the presence invention, particle sizes thereof, concentrations and possible commercial products, reference is made to International patent application published as WO 2012/019669 and disclosure regarding abrasives of this publication is incorporated herein.

The aqueous suspension of the invention may contain an agricultural spray adjuvant. The spray adjuvant may be a surfactant or wetting agent. The surfactant and wetting agent has multiple advantages in the present invention. It reduces the surface tension of the water of the aqueous suspension and makes the waxy surface of plant leaves more permeable for agrobacteria. It further improves the stability of the suspension and reduces settling of the abrasive in the suspension. Surfactants usable in the processes of the present invention are not particularly limited, and are disclosed in International patent application published as WO 2012/019669. Preferred surfactants are nonionic surfactants of an HLB value of 12 or greater, preferably at least 13. As noninionic surfactants, organo-silicone surfactants such as polyalkyleneoxide-modified heptamethyltrisiloxane are most preferred in the present invention. A commercial product is Silwet L77™ spray adjuvant from GE Advanced Materials.

Surfactants such as those disclosed in WO 2012/019669 may be used singly or in combination of two or more surfactants. Notably, the preferred organo-silicone surfactants may be combined with other surfactants. The total concentration of surfactants in the aqueous suspension of the invention may be easily tested by conducting comparative spraying experiments, similarly as done in the examples. However, in general, the total concentration of surfactants may be between 0.005 and 2 volume- %, preferably between 0.01 and 0.5 volume- %, more preferably between 0.025 and 0.2 volume- %, of said suspension. Since the density of surfactants is generally close to 1.0 g/ml, the total concentration of surfactants may be defined as being between 0.05 and 20 g per liter of said suspension, preferably between 0.1 and 5.0 g, more preferably between 0.25 and 2.0 g per liter of said suspension (including abrasive). If the above organo-silicone surfactants such as polyalkyleneoxide-modified heptamethyltrisiloxane are used, the concentration of the organo-silicone surfactant in the agrobacterial suspension used for spraying may be between 0.01 and 0.5 volume- %, preferably between 0.05 and 0.2 volume- %. Alternatively, the concentration of the organo-silicone surfactant in the agrobacterial suspension used for spraying may be defined as being between 0.1 and 5.0 g, preferably between 0.5 and 2.0 g per liter of said suspension.

In order to improve the physical properties of the aqueous suspension, it is possible to add highly dispersed sub-micron size silicic acid (silica) or porous polymers such as urea/formaldehyde condensate (Pergopak™). Notably, where the median particle size of the abrasive is between 0.1 and 30 μm, or in one of the preferred sub-ranges of this range given above, it is possible to add a highly dispersed sub-micron size silica to the suspension. Herein, sub-micron size silica is silica having a median particle size between 0.01 and 0.5 μm, preferably between 0.02 and 0.5 μm, more preferably between 0.02 and 0.1 μm. Highly dispersed silicic acid such as Hi-Sil™ 233 (PPG Industries) can contribute to the abrasive properties of the aqueous suspension (see Jensen et al., Bull. Org. mond. Sante, Bull. Wld Hlth Org. 41 (1969) 937-940). These agents may be incorporated in an amount of from 1 to 10 g per liter of the suspension of the invention.

Further possible additives to the agrobacterial suspension are buffer substances to maintain the pH of the suspension used for spraying at a desired pH, typically between 4.5 and 6.5, preferably between 5.0 and 5.5. Further, inorganic soluble salts such as sodium chloride may be added to adjust the ionic strength of the suspension. Nutrient broth such as LB medium may also be contained in the suspension.

The aqueous suspension for contacting with plants may be produced as follows. In one method, the *Agrobacterium* strain or cells containing the desired binary vector to be used in the process of the invention is inoculated into culture medium and grown to a high cell concentration. Larger cultures may be inoculated with small volumes of a highly concentrated culture medium for obtaining large amounts of the culture medium. Agrobacteria are generally grown up to a cell concentration corresponding to an OD at 600 nm of at least 1, typically of about 1.5. Such highly concentrated agrobacterial suspensions are then diluted to achieve the desired cell concentration. For diluting the highly concentrated agrobacterial suspensions, water is used. The water may contain a buffer. The water may further contain the surfactant of the invention. Alternatively, the concentrated agrobacterial suspensions may be diluted with water, and any additives such as the surfactant and the optional buffer substances are added after or during the dilution process. The abrasive may be added before, during or after dilution. It is however preferred to agitate the suspension during addition of the abrasive to uniformly disperse the abrasive in the agrobacterial suspension. The step of diluting the concentrated agrobacterial suspension may be carried out in the spray tank of the sprayer used for spraying the diluted suspensions.

Said plants, notably leaves on said plant are then contacted with the suspension of *Agrobacterium* cells to effect transient transfection of cells of the plant. As explained above, contacting may be done by spraying. The sprayer to be used in the process of the invention mainly depends on the number of plants or the area to be sprayed. For one or a small number of plants to be sprayed, pump sprayers as widely used in household and gardening can be used. These may have volumes of the spray tank of between 0.5 and 2 liters. For applications on a medium scale, manually operated hydraulic sprayers such as lever-operated knapsack sprayers or manually operated compression sprayers may be used. However, the high transfection efficiency achieved in the invention has its full potential in the transfection of many plants such as plants growing on a farm field or in a greenhouse. For this purpose, power-operated hydraulic sprayers such as tractor-mounted hydraulic sprayers equipped with spray booms can be used. Aerial application techniques using helicopters or airplanes are also possible for large fields. All these types of sprayers are known in the art and are described for example in the book "Pesticide Application Methods" by G. A. Matthews, third edition, Blackwell Science, 2000. In order to ensure a homogeneous suspension in the spray tanks of the sprayers, small or medium size sprayers may be shaken at regular intervals or continuously during spraying. Large sprayers such as the tractor-mounted sprayers should be equipped with an agitator in the spray tank.

Considering the presence of agrobacterial cells and abrasive in the suspensions to be sprayed, sprayers used in the invention should produce spray of a droplet size at least of fine spray. Also, medium spray or coarse spray in the classification of sprays used in "Pesticide Application Methods" by G. A. Matthews, third edition, Blackwell Science, 2000, page 74, may be used. The main purpose of the spraying in the invention is wetting of plant tissue with the suspension. Thus, the exact droplet size is not critical. However, the transfection efficiency may be further improved by providing the spray to plant surfaces with increased pressure.

In the process of the invention, at least parts of plants are sprayed. In an important embodiment, plants growing in soil on a field are sprayed, i.e. plants not growing in movable pots or containers. Such plants cannot be turned upside down and dipped into agrobacterial suspension for vacuum infiltration. At least parts of plants are sprayed such as leaves. Preferably, most leaves are sprayed or entire plants.

The present invention is used for transient transfection of plants or for transient with a DNA sequence of interest that may then be transiently expressed. The term "transient" means that the no selection methods are used for selecting cells or plants transfected with the DNA sequence of interest in the background of non-transfected cells or plants using, e.g. selectable agents and selectable marker genes capable of detoxifying the selectable agents. As a result, the transfected DNA sequence of interest is generally not stably introduced into plant chromosomal DNA. Instead, transient methods make use of the effect of transfection in the very plants transfected.

The invention is generally used for transfecting multicellular plants, notably, higher plants. Both monocot and dicot plants can be transfected, whereby dicot plants are preferred. Plants for the use in this invention include any plant species with preference given to agronomically and horticulturally important crop species. Common crop plants for the use in present invention include alfalfa, barley, beans, canola, cowpeas, cotton, corn, clover, lotus, lentils, lupine, millet, oats, peas, peanuts, rice, rye, sweet clover, sunflower, sweetpea, soybean, sorghum triticale, yam beans, velvet beans, vetch, wheat, wisteria, and nut plants. The plant species preferred for practicing this invention include, but not restricted to, representatives of *Gramineae, Compositeae, Solanaceae* and *Rosaceae.*

Further preferred species for the use in this invention are plants from the following genera: *Arabidopsis, Agrostis, Allium, Antirrhinum, Apium, Arachis, Asparagus, Atropa, Avena, Bambusa, Brassica, Bromus, Browaalia, Camellia, Cannabis, Capsicum, Cicer, Chenopodium, Chichorium, Citrus, Coffee, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pelargonium, Pennisetum, Petunia, Pisurn, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum, Stenotaphrum, Theobroma, Trifolium, Trigonelia, Triticum, Vicia, Vigna, Vitis, Zea*, and the *Olyreae*, the *Pharoidese* and others.

Preferably, the processes of the invention are applied to dicot plant such as *Nicotiana benthamiana*, tobacco, cotton, soybean, rapeseed, pepper, potato, or tomato.

In one embodiment, the process of the invention can be used for producing a protein of interest in a plant or in many plants growing on a field. For this purpose, the plants may be sprayed with the suspension comprising the *Agrobacterium* cells containing the desired binary vector at a desired growth state of the plants. If the main aim is to achieve the highest possible expression levels followed by harvesting plants for obtaining plant material containing high amounts of the protein, viral vectors may be used, since they generally give the highest expression levels.

In another embodiment, the process of the invention is used for generating or altering a trait in a plant such as an input trait. In this embodiment, excessive expression of a protein or RNA of interest may not be desired for avoiding deleterious effects on plant health. For such embodiments, non-replicating vectors (also referred to herein as "transcriptional vectors"), i.e. vectors lacking a functional origin of replication recognised by a nucleic acid polymerase present in the plant cells are preferred. Another application of the invention is RNA expression, e.g. for RNA interference, wherein the interference signal can spread in the plant from cells having expressed the signal to other cells. An example is the targeting of undesired viral DNA in plants as described by Pooggin in Nat. Biotech. 21 (2003) 131. An example of oncogene silencing that can be adapted to a transient system is described by Escobar et al. Proc. Natl. Acad. Sci. USA 98 (2001) 13437-13442. A further example is the control of coleopteran insect pests through RNA interference similar as described by Baum et al., Nat. Biotech. 25 (2007) 1322-

1326 that can be adapted to the transient process of the invention by transiently transfecting pest-infested plants with a DNA sequence of interest encoding the dsRNA such that it can be expressed. Further methods applicable to the transient process of the invention are those described by Huang et al., Proc. Natl. Acad. Sci. USA 103 (2006) 14302-14306; Chuang et al., Proc. Natl. Acad. Sci. USA 97 (2000) 4985-4990.

Further, the process of the invention allows altering at a desired point in time traits relating to the regulation of flowering time or fruit formation such as tuberisation in potato (Martinez-Garcia et al., Proc. Natl. Acad. Sci, USA 99 (2002) 15211-15216) or the regulation of the flavonoid pathway using a transcription factor (Deluc et al., Plant Physical. 147 (2008) 2041-2053). Flowering may be induced by transiently expressing the movable florigen protein FT (Zeevaart, Current Opinion in Plant Biology 11 (2008) 541-547; Corbesier et al., Science 316 (2007) 1030-1033). Parthenocarpic fruits in tomatoes may by produced on a large scale using the invention and the method described by Pandolfini et al., BMC Biotechnology 2 (2002). Further applications of the invention are in the context of altering cotton fiber development by way of MYB transcription factors as described by Lee et al., Annals of Botany 100 (2007) 1391-1401 or activation of plant defensive genes (Bergey et al., Proc. Natl. Acad. Sd. USA 93 (1996) 12053-12058.

The invention also provides a process of protecting crop plants on a field from a pest. In such process, infestation of at least one of the plants from a plurality of plants growing in a lot or farm field may be determined. Due to the rapidness of the process of the invention expression of a protein or RNA detrimental to the pest needs to be caused only if infestation by the pest is determined. Thus, strong and constitutive expression of pest toxins or dsRNA for RNAi even in the absence of a risk of infestation is not necessary. Transient expression of *Bacillus thuringiensis* endotoxins after the spraying with diluted agrobacterial cultures harbouring corresponding PVX-based expression vectors protected *Nicotiana benthamiana* plants from feeding damage by larvae of the tobacco hornworm Manduca sexta (cf. FIG. 30 of WO 2012/019660).

EXAMPLES

Reference Example 1 Determination of *Agrobacterium* Cell Concentration in Liquid Culture in Terms of Colony Forming Units (cfu)

The concentration of *Agrobacterium* cells in liquid suspension in terms of colony forming units per ml (cfu/ml) of liquid suspensions can be determined using the following protocol. Cells of *Agrobacterium tumefaciens* strain ICF 320 transformed with construct pNMD620 were grown in 7.5 ml of liquid LBS medium containing 25 mg/L kanamycin (AppliChem, A1493) and 50 mg/L rifampicin (Carl Roth, 4163.2). The bacterial culture was incubated at 28° C. with continuous shaking. Absorbance or optical density of bacterial culture expressed in absorbance units (AU) was monitored in 1-ml aliquots of the culture using a spectrophotometer at 600 nm wavelength (OD600). The cell concentration estimated as a number of colony-forming units per milliliter of liquid culture (cfu/ml) can be analyzed at OD600 values 1; 1.3; 1.5; 1.7 and 1.8. For this purpose 25 μl aliquots of liquid culture were diluted with LBS-medium to achieve a final volume of 25 ml (dilution 1:100). 2.5 ml of such 1:100 dilution were mixed with 22.5 ml of LBS to achieve the dilution 1:1000. Liquid culture dilutions 1:100; 1:1,000; 1:10,000; 1:100,000; 1; 1,000,000; 1:10,000,000 and 1:100,000,000 were prepared similarly. Aliquots of last three dilutions were spread on agar-solidified LBS medium supplemented with 26 mg/L kanamycin and 60 mg/L rifampicin (250 μl of bacterial culture per plate of 90 mm diameter). Plating of aliquots for each dilution was performed in triplicate. After 2 days incubation at 28° C., bacterial colonies were counted for each plate. Plating of 1:1,000,000 and 1:10,000,000 dilutions resulted in few hundred and few dozen colonies per plate, respectively. So far as dilution 1:100,000,000 provided just few colonies per plate, this dilution was not used for calculation of cell concentration. The cell concentration was estimated according to the formula: cfu/ml=4×number of colonies per plate× dilution factor.

For transforming cell concentrations as measured by absorbance measurements at 600 nm (in LB medium) and in terms of cell-forming units, the following relation is used herein: an OD600 of 1.0 corresponds to $1.1 \times 10^9$ cfu/ml.

LBS Medium (Liquid)

1% soya peptone (papaic hydrolysate of soybean meal; Duchefa, S1330)

0.5% yeast extract (Duchefa, Y1333)

1% sodium chloride (Carl Roth, 9265.2)

dissolved in water, and the is adjusted to pH 7.6 with 1M NaOH (Carl Roth, 6771.2)

To prepare the solid LBS medium, liquid LBS medium was supplemented with 1.5% agar (Carl Roth, 2266.2). Media were autoclaved at 121° C. for 20 min.

Example 1: Vectors Used in the Following Examples

In this study we used TMV- and PVX-based viral vectors as well as standard transcriptional vectors based on 35S CaMV promoter.

TMV-based vectors with cell-to-cell movement ability pNMD560, pNMD062, pNMD063 and pNMD064 (FIG. 1A) were created on the basis of vectors described in Marillonnet et at (2006). All these vectors are designed for the expression of GFP as a reporter gene; they contain the insertion of a coding sequence of sGFP that is modified green fluorescent protein (GFP) from jelly fish *Aequorea victoria* (GeneBank accession no. EF030489). The pNMD560 construct contains, in sequential order, a fragment from the *Arabidopsis* actin 2 (ACT2) promoter (GenBank accession no. AB026654); the 5' end of TVCV (GenBank accession no. BRU03387, base pairs 1-5455) and a fragment of cr-TMV [GenBank accession no. 229370, base pairs 5457-5677, both together containing 16 intron insertions]; a sGFP coding sequence; cr-TMV 3' nontranslated region (3' NTR; GenBank accession no. Z29370), and the nopaline synthase (Nos) terminator. The entire fragment was cloned between the T-DNA left and right borders of binary vector.

The pNMD062 plasmid was created on the basis of pNMD560 construct. For this purpose, a DNA fragment comprising the coding sequence and a 5'-upstream genomic region of a virG gene of octopine-type Ti-plasmid from LBA4404 strain of *Agrobacterium tumefaciens* (GenBank accession no. AF242881.1, base pairs 160603-161600) flanked by the sequence ctgtcgatc from the 5'-terminus and the sequence aagatcgacag (SEQ ID NO: 8) from the 3' terminus was amplified by PCR and inserted into the plasmid backbone using Afel restriction site.

The pNMD063 construct was identical to pNMD062 except for the N54D mutation.

To create pNMD064 construct, a DNA fragment comprising the coding sequence containing the N54D mutation and 5'-upstream genomic region of virG gene of nopaline-type Ti-plasmid from GV3101 strain of *Agrobacterium tumefaciens* (GenBank accession no. AE007871.2, base pairs 194307-193333) was amplified by PCR and inserted into the plasmid backbone of pNMD560 construct using Afel restriction site.

Figure 1A:
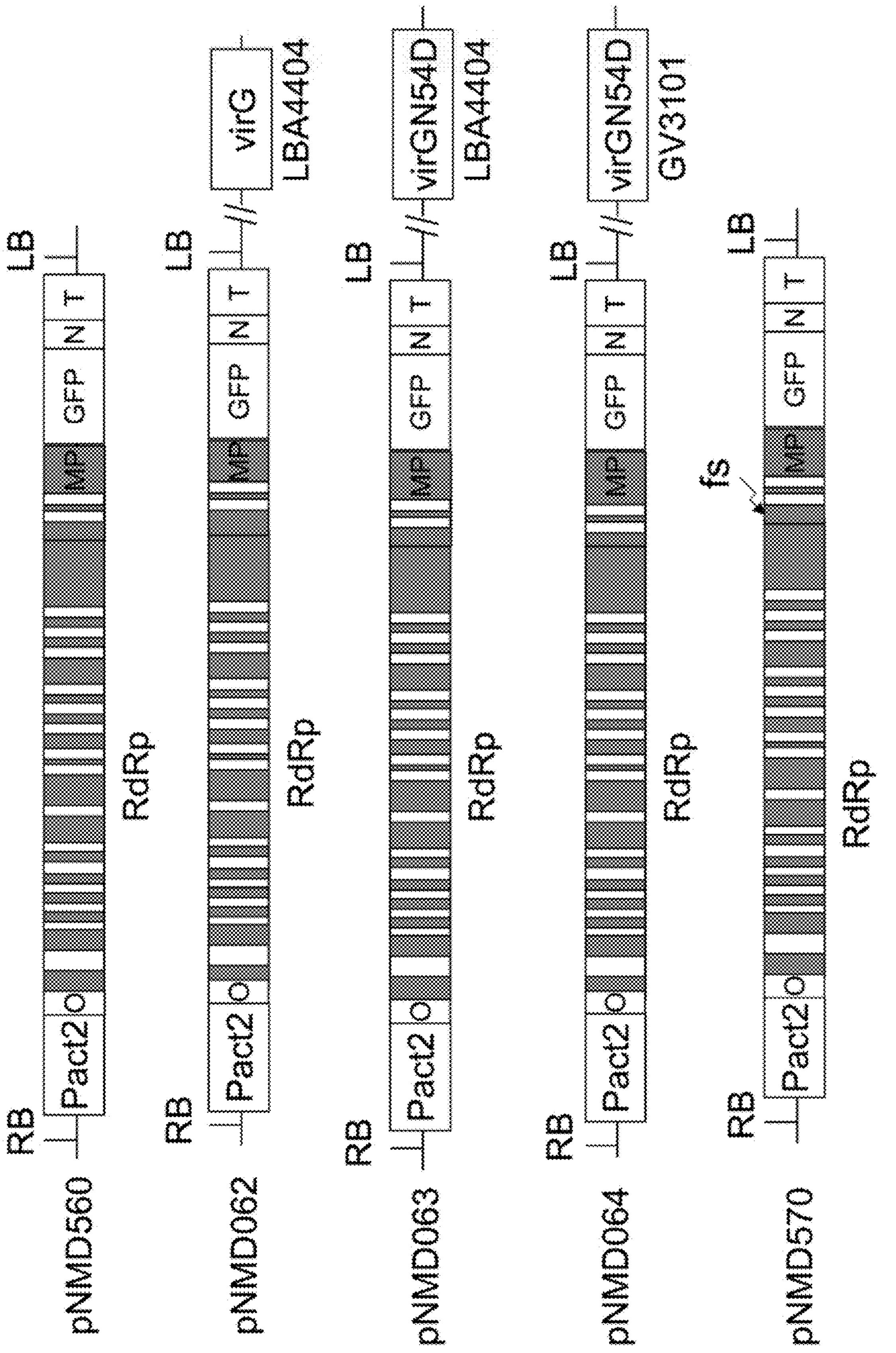
FIGS. 1A and 1B show T-DNA regions with DNA sequences of interest of vectors used in the examples. Pact2: promoter of *Arabidopsis* actin2 gene; o: 5'-end from TVCV (turnip vein clearing virus); RdRp: RNA-dependent RNA polymerase open reading frame (ORF) from cr-TMV (crucifer-infecting tobamovirus); MP; movement protein ORF from cr-TMV; N: 3'-non-translated region from cr-TMV; Tnos or nos: nopaline synthase terminator; white segments interrupting grey segments in the RdRp and MP ORFs indicate introns inserted into these ORFs for increasing the likelihood of RNA replicon formation in the cytoplasm of plant cells, which is described in detail in WO2005049839; GUS: coding sequence of GUS protein; GFP: green fluorescent protein coding sequence; fs: frame-shift deleting cell-to-cell movement ability; P35S: 35S promoter; P19; gene silencing suppressor of tomato bushy stunt virus (cf. Plant J. 33, 949-56); Tocs: ocs terminator; LB: left T-DNA border; RB: right T-DNA border.

The pNMD570 construct (TMV-based vectors lacking cell-to cell movement ability) was identical to pNMD560 except for a point mutation in the MP-coding sequence leading to an open reading frame shift that distorts MP translation (FIG. 1A).

Figure 1B:
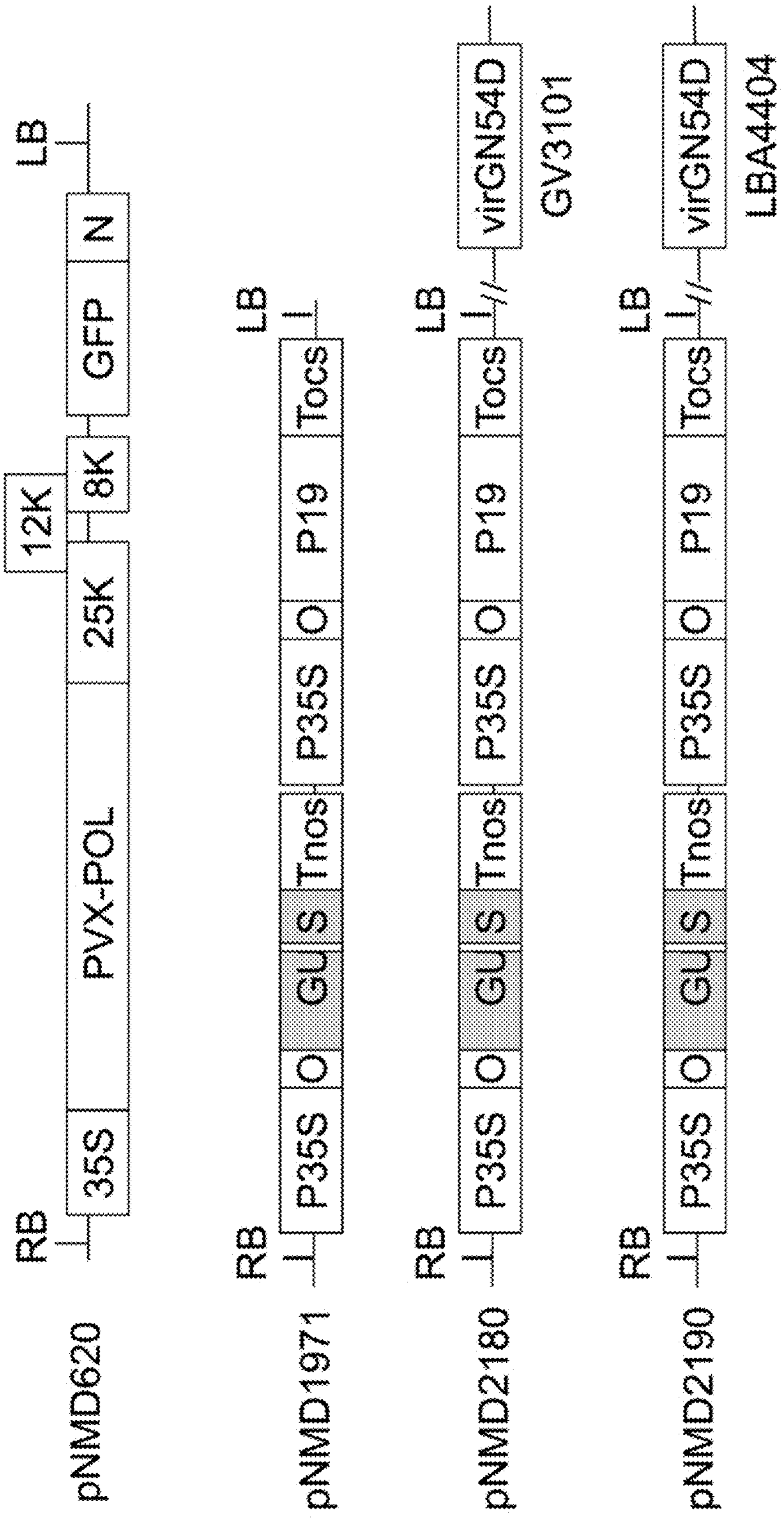

The pNMD620 construct, a PVX-based vector without cell-to-cell and systemic movement abilities for GFP expression, contained, in sequential order, a 35S CaMV promoter, coding sequences of the RNA-dependent RNA polymerase, triple gene block modules comprising 25 kDa, 12 kDa and 8 kDa proteins, an sGFP coding sequence and a 3'-untranslated region. The entire fragment was cloned between the T-DNA left and right borders of binary vector (FIG. 1B).

All transcriptional vectors were created on the basis of pICBV10, a pBIN19-derived binary vector (Marillonnet et al., 2004, 2006). They contained two expression cassettes inserted within right and left borders of the same T-DNA region (FIG. 1B). In the case of the pNMD1971 construct, an expression cassette adjacent to the right border comprised, in sequential order, the Cauliflower mosaic virus (CAMV) 35S promoter, omega translational enhancer from Tobacco Mosaic Virus, coding sequence of beta-glucuronidase from *Escherichia coli* (GenBank accession no. 569414) containing the intron from *Petunia hybrids* PSK7 gene (GenBank accession no. AJ224165.1, base pairs 44114484), and the terminator from the nopaline synthase gene of *Agrobacterium tumefaciens*. The second expression cassette was inserted between the first one and the T-DNA left border. It contained, in sequential order, the Cauliflower mosaic virus (CAMV) 35S promoter, omega translational enhancer from Tobacco Mosaic Virus, coding sequence of P19 suppressor of silencing from Tomato Bushy Stunt Virus (TBSV) (GenBank accession no. CAB56483.1) and terminator from octopine synthase gene of *Agrobacterium tumefaciens.*

The pNMD2180 construct was created on the basis of the pNMD1971 vector. For this purpose, the Notl/Ndel fragment of the pNMD1971 construct was replaced with same fragment of pNMD064 construct containing virGN54D gene of nopaline-type Ti-plasmid from GV3101 strain of *Agrobacterium tumefaciens* flanked by 5'-upstream genomic region.

The pNMD2190 was created in a similar way. The Notl/Ndel fragment of pNMD1971 construct was replaced with same fragment of pNMD063 vector containing virGN54D gene of octopine-type Ti-plasmid from LBA4404 strain of *Agrobacterium tumefaciens* flanked by 5'-upstream genomic region.

Figure 2A:
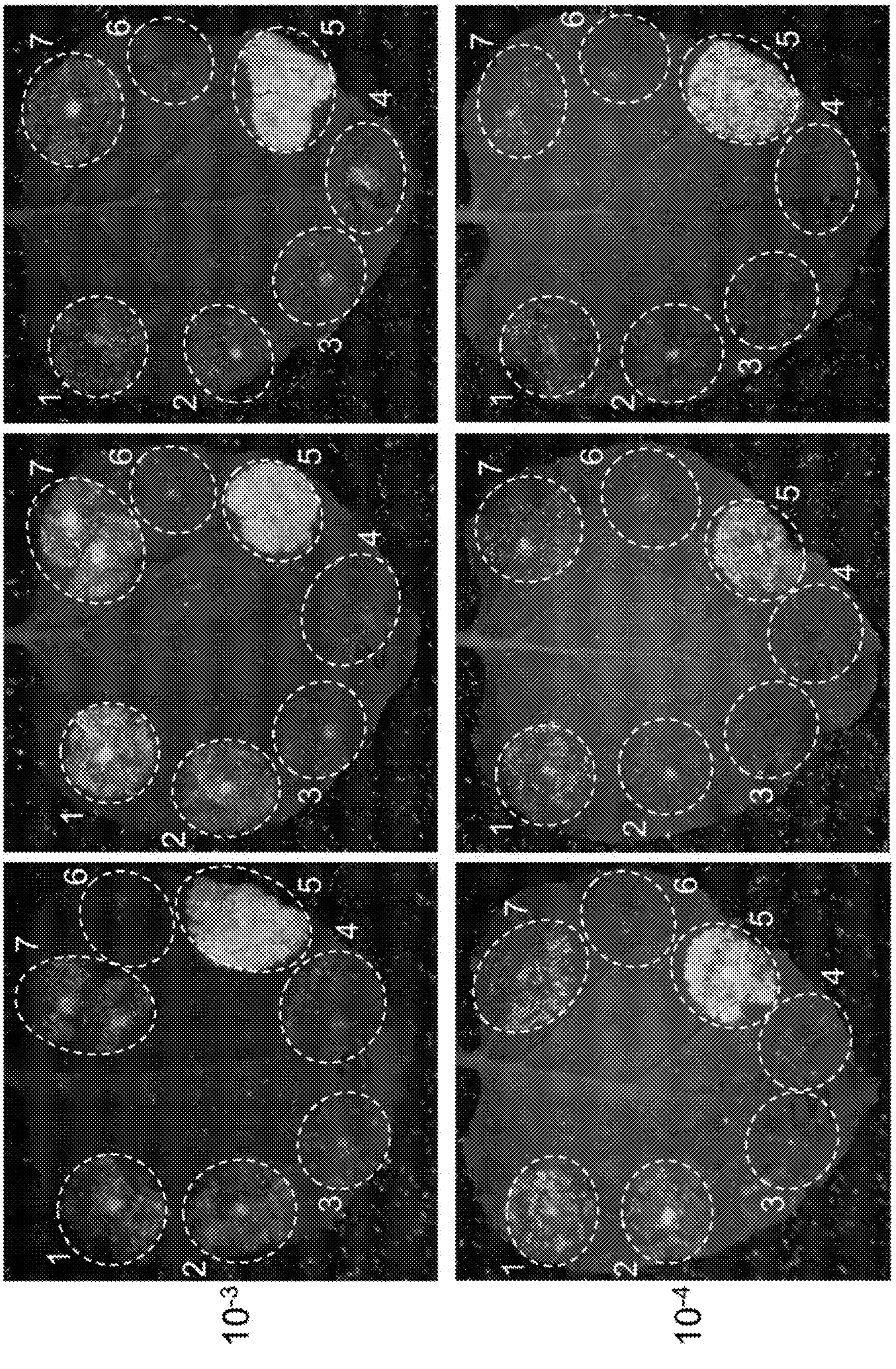
FIG. 2 shows a comparison of different *Agrobacterium tumefaciens* strains for their transient transfection efficiency. Photographs show GFP fluorescence 4 dpi (days post infection) under uv light due to TMV-based GFP expression after syringe infiltration of *Nicotiana benthamiana* leaves with diluted agrobacterial cultures as described in Example 2. Numerals $10^{-2}$, $10^{-3}$ and $10^{-4}$ show the concentration factors of the overnight agrobacterial cultures of OD=1.3 at 600 nm that correspond to $10^2$-fold, $10^3$-fold and $10^4$-fold dilutions, respectively. The composition of the buffer for infiltration is 5 mM MES, pH5.5 and 10 mM $MgSO_4$. Each infiltration was performed in triplicate using three independent leaves of the same plant.
Figure 2B:
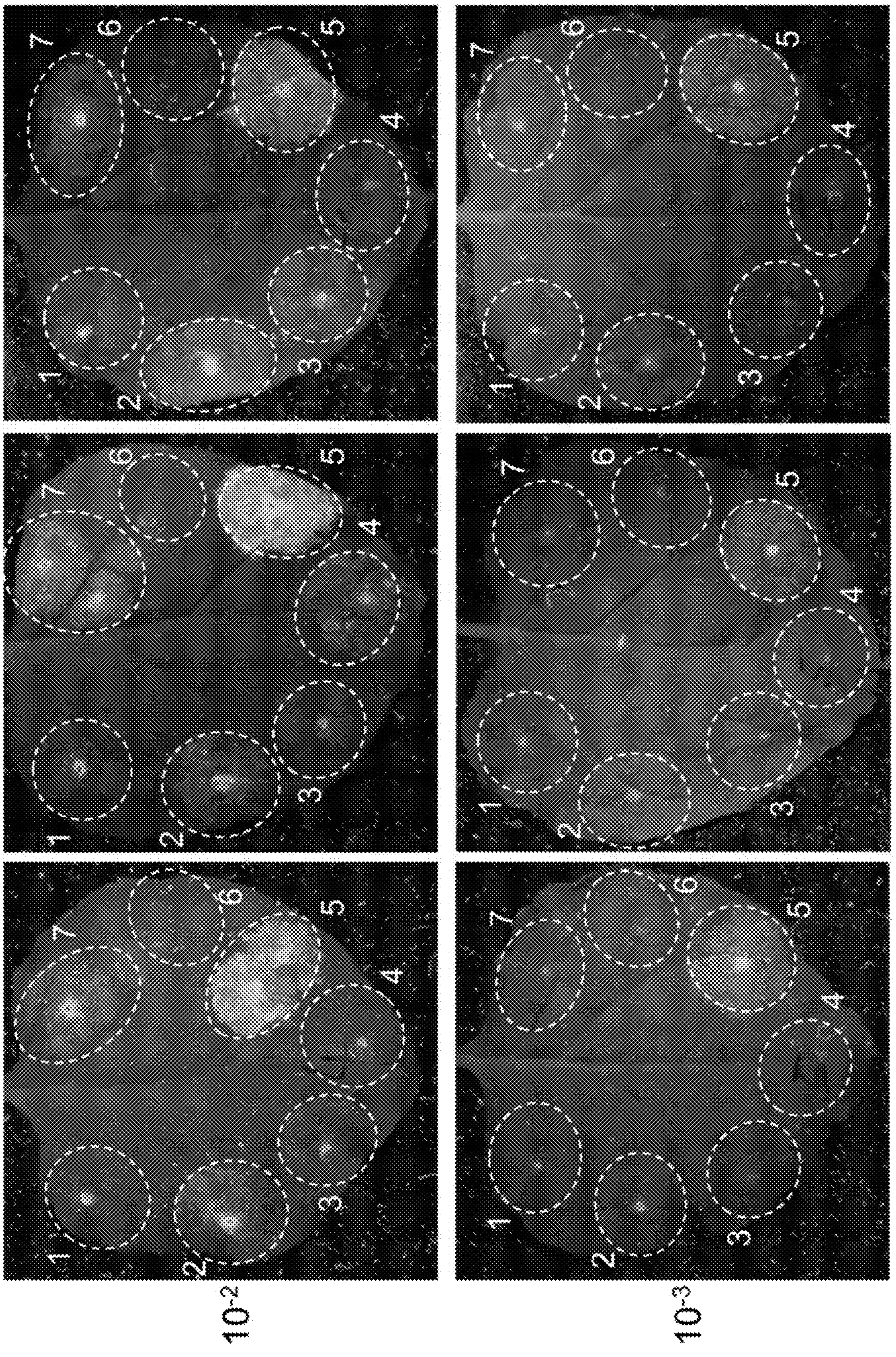

Example 2: Strain CryX Shows Stronger Transient Transfection of *Nicotiana benthamiana* if Compared with Commonly Used *Agrobacterium tumefaciens* Strains We tested the number of *Agrobacterium tumefaciens* strains including AGL1, EHA105, GV3101, ICF320, CryX, LBA4404 and LBA9402 for the transient transfection of *Nicotiana benthamiana* plants. For this purpose plant leaves were infiltrated using a needleless syringe with $10^{-3}$ and $10^{-4}$ dilutions of $OD_{600}$=1.3 of agrobacterial cultures of the seven above-mentioned strains harboring a GFP expression TMV-based vector capable of cell-to-cell movement (TMV-GFP, pNMD560 construct) as it is shown in FIG. 2A. In parallel, leaves were infiltrated with $10^{-2}$ and $10^{-3}$ dilutions of the overnight agrobacterial cultures of same strains carrying TMV-based vector lacking cell-to-cell movement ability (TMV(fsMP)-GFP, pNMD570 construct) as it is shown in FIG. 2B.

Based on the density of fluorescing spots and the intensity of GFP fluorescence, we proved the efficient transient transfection for several strains (e.g., AGL1, EHA105, and LBA9402) however the transient transfection efficiency of CryX strain was significantly higher for both constructs with all tested dilutions of agrobacterial cultures if compared with any other tested strain.

To provide a quantitative evaluation of transient transfection efficiency for the CryX strain, we estimated the ratio between the number of cells in the bacterial suspension infiltrated in leaves and the number of produced GFP fluorescent spots considered as a single transfection event. For this purpose, leaves of 6-weeks old *Nicotiana benthamiana* plants were infiltrated using a syringe without needle with 200 μl of agrobacterial cultures of OD600=1.3 diluted by dilution factors of $10^{-5}$, $10^{-5}$ and $10^{-7}$ with a buffer consisting of 5 mM MES, pH 5.3 and 10 mM $MgCl_2$. CryX, EHA105, GV3101 and ICF320 agrobacterial cells carried constructs pNMD560 (TMV-GFP vector). For the scoring of bacterial cells, 100 μl aliquots of bacterial suspensions used for leaf infiltration were plated in triplicate on LB-agar plates containing 50 μl/l rifampicin and 50 μl/l kanamycin. Plates were incubated for 2 days at 28° C. and after that the number of cfu (colony forming units) was counted. According to our estimation, 100 μl of bacterial cultures of CryX, EHA105, GV3101 and 1CF320 contained 7.38+/−1.72, 5.00+/−1.50, 2.53+/−0.87 and 6.17+/−1.37 cfu (Table 1). In parallel at 4 dpi *Nicotiana benthamiana* leaves were scored for GFP fluorescent spots. On average, 7.38+/−1.72, 5.00+/−1.50, 2.53+/−0.87 and 6.17+/−1.37 fluorescent spots were produced per 100 μl of $10^{-7}$ dilution of infiltrated agrobacterial culture for CryX, EHA105, GV3101 and 1CF320 strains, respectively. Each agrobacterial cell produced 0.46 transfection loci for CryX strain and 0.01 transfection loci for all other tested strains, CryX strain being 46 times more efficient than EHA105, GV3101 and ICF320 strains.

TABLE 1

Transfection efficiency of CryX in comparison with other strains at concentration factor $10^{-7}$ of agrobacterial culture (pNMD560 construct, 4 dpi).

| | CryX | EHA105 | GV3101 | ICF320 |
|---|---|---|---|---|
| GFP spots/100 µl input culture | 2.85 +/− 0.83 | 0.06 +/− 0.02 | 0.03 +/− 0.01 | 0.06 +/− 0.02 |
| cfu/100 µl input culture | 7.38 +/− 1.72 | 5.00 +/− 1.50 | 2.53 +/− 0.87 | 6.17 +/− 1.37 |
| GFP spots/cfu of input culture | 0.46 | 0.01 | 0.01 | 0.01 |

Example 3. Overexpression of virG Gene from LBA4404 Strain Increases the Transient Transfection Efficiency of CryX Strain We tested the influence of overexpression of virG genes on the transient transfection efficiency of several *Agrobacterium* strains. For this purpose we created TMV-based vectors carrying the insertion of virG genes either from GV3101 or LBA4404 strains in their plasmid backbones (FIG. 1A). First, we tested AGL1, EHA105, ICF320 and GV3101 strains using vectors harboring virGN54D genes from GV3101 and LBA404 strains (pNMD063 and pNMD064, respectively) as well as a vector with native virG gene sequence from LBA4404 strain (pNMD062). *Nicotiana benthamiana* leaves were infiltrated using syringe without needle with $10^2$, $10^3$ and $10^4$-fold dilutions of $OD_{600}$=1.3 of agrobacterial cultures. Photographs showing GFP fluorescence in the uv light were taken at 4th (FIG. 3A) and 6th dpi (FIG. 3B). Based on the visual evaluation, we demonstrated the strain-specific increase of the transient transfection efficiency. As it is summarized in Table 2, overexpression of virGN54D from GV3101 strain increased the transient transfection efficiency for GV3101 and 1CF320 strains; virGN540 from LBA4404 strain improved the transient transfection efficiency of AGA1, EHA105 and LBA4404 strains.

The CryX strain was tested similarly, as shown in FIG. 4. *Nicotiana benthamiana* leaves were infiltrated using syringe without needle with liquid CryX and GV3101 agrobacterial cultures of OD600=1.3 diluted $10^{-4}$ and $10^{-5}$ with buffer for infiltration. GFP expression TMV-based vectors containing virGN54D genes from GV3101 and LBA404 strains in the plasmid backbone (pNMD063 and pNMD064, respectively) were compared with pNMD560 vector containing no virG gene insertion. FIG. 4A depicts the GFP fluorescence for the dilution $10^{-4}$ at 3 and 4 dpi FIG. 4B shows the GFP fluorescence for the dilution $10^{-5}$ at 4 and 5 dpi. We demonstrated a significant increase of transient transfection efficiency for CryX strain in combination with virGN54D gene from LBA4404; in contrast, the overexpression of virGN54D gene from GV3101 strain had a negative impact on CryX-mediated transient transfection.

TABLE 2

Effect of virG overexpression on the T-DNA transfer efficiency

| *Agrobacterium* strain | virGN54D/GV3101 | virGN54D/LBA4404 |
|---|---|---|
| AGL1 | no effect | increase |
| GV3101 | increase | no effect |
| ICF320 | increase | no effect |
| EHA105 | no effect | increase |
| LBA4404 | no effect | increase |

Example 4. CryX in Combinations with virGIV54D/LBA4404 Provides Efficient Transient Transfection of *Nicotiana benthamiana* in Up to $10^7$-Fold Dilutions Using Leaf Infiltration To find the maximal effective dilutions of CryX liquid cultures for transient transfection of *Nicotiana benthamiana* plants, we performed syringe infiltration of leaves with liquid CryX and GV3101 agrobacterial cultures of OD600=1.3 diluted to $10^{-3}$, $10^{-4}$, $10^{-5}$, $10^{-6}$ and $10^{-7}$ with buffer for infiltration.

In our experiments, *Agrobacterium tumefaciens* strain CryX in combination with virGN54D from LBA4404 strain provided the most efficient transfection of *Nicotiana benthamiana* plants we ever observed, resulting in the reasonable number of fluorescing spots even at the $10^{-7}$ concentration factor of overnight culture (FIG. 5). It allows increasing the dilution of agrobacterial culture used for plant infiltration approx. 100 to 1000-fold compared with $10^3$-fold dilution typically used in Magnicon® system.

To provide a quantitative evaluation of transient transfection efficiency for CryX strain, we estimated the ratio between the number of cells in the bacterial suspension infiltrated in leaves and the number of produced GFP fluorescent spots considered as a single transfection event. For this purpose leaves of 6-weeks old *Nicotiana benthamiana* plants were infiltrated using syringe without needle with 200 µl of agrobacterial cultures of OD600=1.3 diluted $10^{-7}$ with an aqueous buffer containing 5 mM MES, pH 5.3 and 10 mM $MgCl_2$. CryX agrobacterial cells carried constructs pNMD560 (TMV-GFP vector) and pNMD062 (TMV-GFP vector containing virGN54D from LBA4404 strain in the plasmid backbone). For scoring of bacterial cells, 100 µl aliquots of bacterial suspensions used for leaf infiltration were plated in triplicate on LB-agar plates containing 50 µl/l rifampicin and 50 µl/l kanamycin. Plates were incubated for 2 days at 28° C. and after that the number of cfu (colony forming units) was counted. According to our estimation. 100 µl of bacterial cultures contained 14.7+/−4.4 and 13.9+/−3.4 cfu for pNM0560 and pNMD062 constructs, respectively (Table 3). In parallel at 5 dpi *Nicotiana benthamiana* leaves were scored for GFP fluorescent spots. In average, 16.3+/−1.5 and 24.0+/−0.0 fluorescent spots were produced per 100 µl of infiltrated agrobacterial culture for pNMD560 and pNMD062 constructs, respectively. In other words, each agrobacterial cell harboring the pNMD560 construct produced about 1.1 transfection loci; for the pNMD062 construct, this value was higher, 1.7, showing an increase of the transfection efficiency due to the overexpression of virG gene.

Figure 6A:
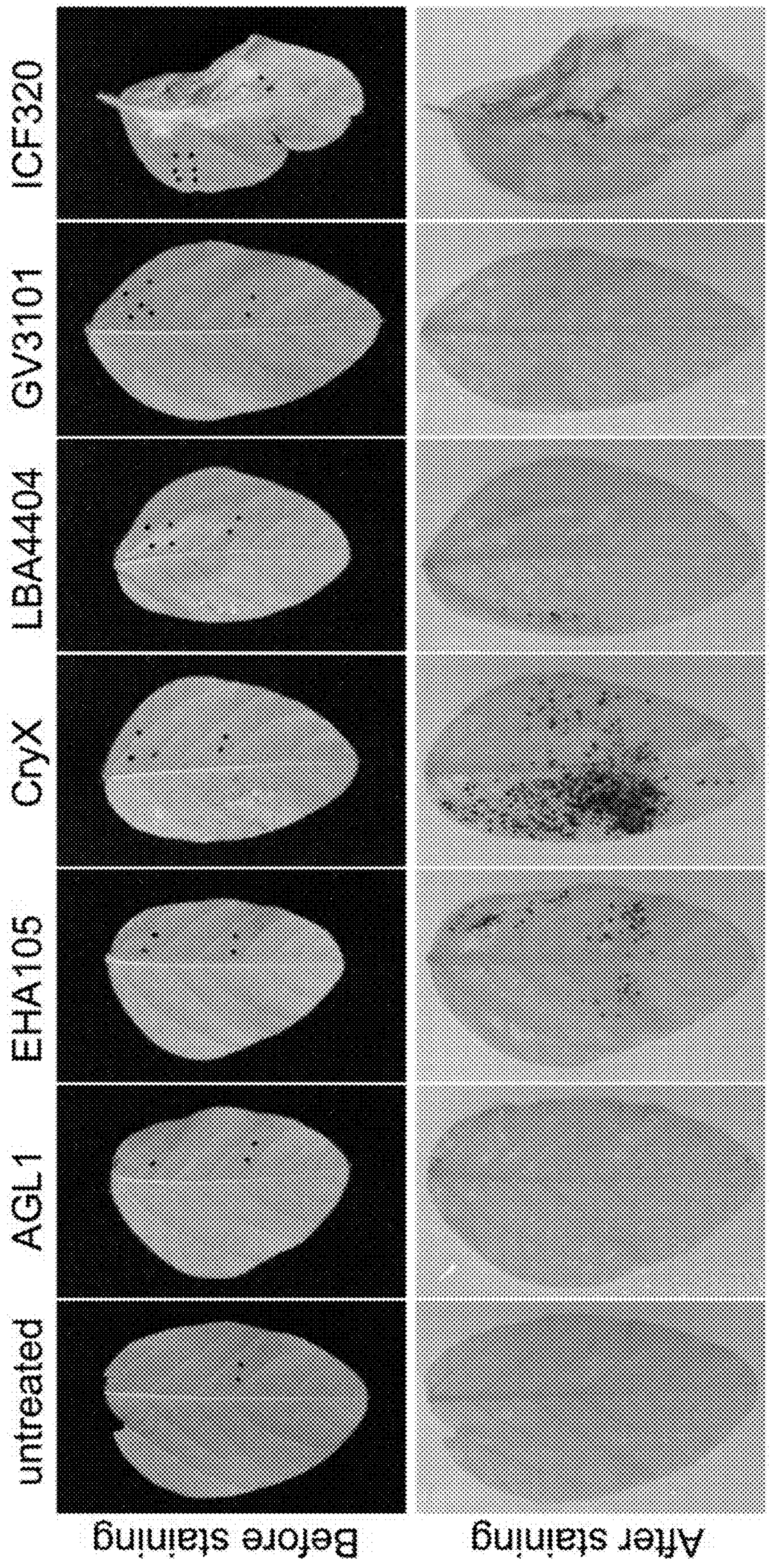

Example 5, *Agrobacterium Tumefaciens* Strain CryX in Combination with virGN54D/LBA4404 Shows High Spraying Transfection Efficiency for Soybean We tested the number of *Agrobacterium tumefaciens* strains including AGL1, EHA105, GV3101, ICF320, CryX and LBA4404 for the transient transfection of soybean *Glycine max* L. using spraying of plants with suspension of agrobacterial cells. For this purpose, liquid cultures harboring GUS expression vectors were grown to OD600=1.3 and diluted for spraying with buffer containing 5 mM MES pH5.3; 10 mM $MgCl_2$ and 0.05% (v/v) Tween®20 in the ratio 1:10. For testing of AGL1, EHA105, CryX and LBA4404 strains, we used pNMD2190 construct (35S:GUS; 35S:p19 and virGN54D/LBA4404 in the plasmid backbone). GV3101 and ICF320 strains were tested with pNMD2180 vector (35S:GUS; 35S:p19 and virGN54D/GV3101 in the plasmid backbone). Staining of leaves for the GUS activity was performed at 11 days post spraying. Compared to other tested strains which showed no or little transfection, CryX provided significantly higher transient transfection rate as revealed by GUS staining (FIG. 6A).

Figure 6B:
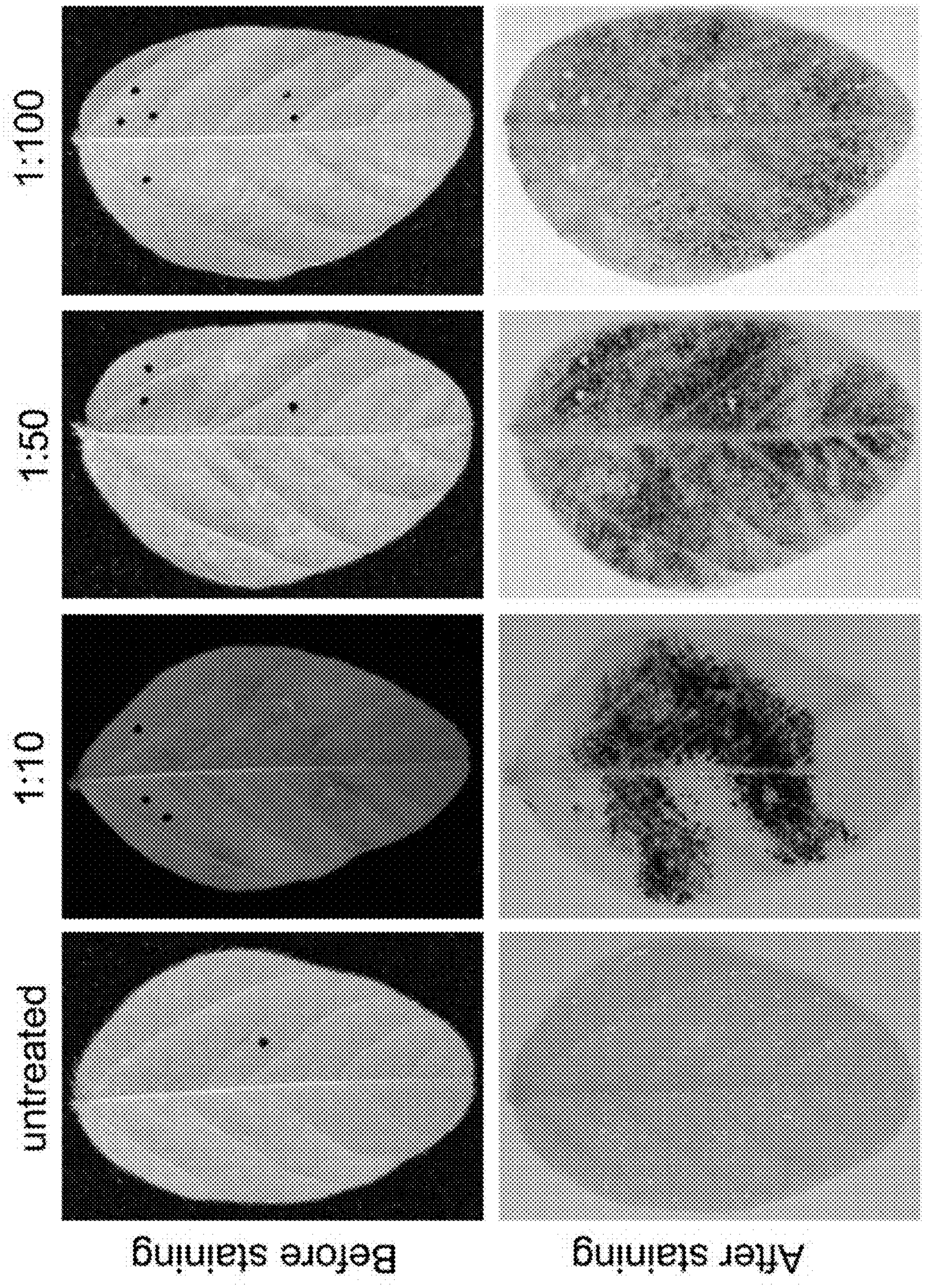

Combining surfactant and abrasive treatment, we achieved efficient transient transfection of soybean with CryX strain for up to $10^{-2}$ dilutions of agrobacterial cultures when GUS expression transcriptional vector pNMD2190 was used (FIG. 6B).

Example 6. *Agrobacterium Tumefaciens* Strain CryX in Combination with virGN54D/LBA4404 Shows Enhanced Transient Spraying Transfection for Cotton We tested the transient transfection of cotton with EHA105, GV3101, ICF320, and CryX strains using spraying. For this purpose liquid *Agrobacterium* cultures of $OD_{600}$=1.3 were diluted in the ratio 1:10 with buffer containing 5 mM MES, pH5.3; 10 mM $MgCl_2$ and 0.25% (v/v) Silwet. L-77. pNMD2180 construct (35S:GUS; 35S:p19 and virGN54D/GV3101 in the plasmid backbone) was used with GV3101 and ICF320 strains, and pNMD2190 (35S:GUS; 35S:p19 and virGN54D/LBA4404 in the plasmid backbone) was used with EHA105 and CryX strains. pNMD1971 construct (35S:GUS; 35S:p19) was applied as a control with all strains. GUS staining test was performed at 6 days post spraying. After the staining, few blue dots were found for GV3101 and ICF320 strains (data not shown). Very low transfection efficiency was shown also for EHA105 and CryX strains used with pNMD1971 construct. Compared with all other tested strains, CryX in combination with virGN54D from LBA4404 strain (pNM02190) demonstrated increased transient transfection efficiency (FIG. 7).

TABLE 3

Transfection efficiency of CryX in combination with virGN54D/LBA4404 (pNMD062 construct)

| | pNMD560 (no virG) | pNMD062 (virGN54D/ LBA4404) |
|---|---|---|
| Dilution of input agrobacterial culture | 10 − 7 | 10 − 7 |
| cfu/100 µl input culture | 14.7 +/− 4.4 | 13.9 +/− 3.4 |
| GFP spots/100 µl input culture, 5 dpi | 16.3 +/− 1.5 | 24.0 +/− 0.0 |
| GFP spots/cfu of input culture | 1.1 | 1.7 |

Example 7. ICBGE Accession of *Agrobacterium tumefaciens* Chry5/KYRT1 Strain Shows Stronger Transient Transfection of *Nicotiana benthamiana* Compared to Kentucky University Accession of Same Strain We tested two accessions of *Agrobacterium tumefaciens* Chry5/KYRT1 strain received from different laboratories, the laboratory of Dr. G. Collins in the University of Kentucky (Lexington, USA) and the accession from the Institute of Cell Biology and Genetics Engineering (ICBGE, Kiev, Ukraine) for the transient transfection of *Nicotiana benthamiana* plants. For this purpose, plant leaves were infiltrated using needleless syringe with dilutions using concentration factors of $10^{-1}$, $10^{-2}$ and $10^{-3}$ of an $OD_{600}$=1.3 of agrobacterial cultures of both strain accessions harboring GFP expression TMV-based vector capable of cell-to-cell movement (TMV-GFP, pNMD560 construct) as it is shown in FIG. 8. Based on the density of fluorescing spots and the intensity of GFP fluorescence, we showed higher transient transfection efficiency for ICBGE accession if compared with Kentucky University accession.

The content of European patent application No. 12 002 402.1 filed on Apr. 3, 2012 is herein incorporated by reference in its entirety, including description, claims, figures and sequence listing.

REFERENCES

Akcay et al., Plant Cell Rep 28 (2009) 407-47.

Akbulut et al, African Journal of Biotechnology 7(8) 1011-1017, 2008

Andrews, L. B. & Curtis, W. R. (2005). Biotechnol Prog 21, 946-52.

Barton, K. A., Binns, A, N., Matzke, A. J. & Chilton, M. D. (1983). Cell 32, 1033-43.

Bush A L, Pueppke S G. Appl Environ Microbial. 1991 September; 57(9):2468-72.

Chung, M. H., Chen, M. K. & Pan, S. M, (2000). Transgenic Res 9, 471-6.

Clough, S. J. & Bent, A. F. (1998). Plant J 16, 735-43.

D'Aoust, M. A., Lavoie, P. O., Belles-Isles. J., Bechtold, N., Martel, M. & Vezina, L. P. (2009). Methods Mol Biol 483, 41-50.

D'Aoust, M. A. Lavoie, P. O., Couture, M. M., Trepanier, S., Guay, J. M., Dargis, M., Mongrand, S., Landry, N., Ward, B. J. & Vezina, L. P. (2008). Plant Biotechnol J 6, 930-40.

De Buck, S., Jacobs, A., Van Montagu, M. & Depicker, A. (1998). Mol Plant Microbe Interact 11, 449-57.

De Buck, S., De Wilde, C., Van Montagu, M. & Depicker, A. (2000). Mol Plant Microbe Interact 13, 658-65.

de Felippes, F. F. & Weigel, D. (2010). Methods Mol Biol 592, 255-64.

Fraley, R. T., Rogers, S. G., Horsch, R. B., Sanders, P. R., Flick, J. S., Adams, S. P., Bittner, M. L., Brand, L. A., Fink, C, L., Fry, J. S., Galluppi, G. R., Goldberg, S. B., Hoffmann, N. L. & Woo, S. C. (1983), Proc Natl Acad Sci USA 80, 4803-7.

Gleba Y. Y. and Giritch A. (2011) Plant Viral Vectors for Protein Expression. In Recent Advances in Plant Virology, Caister Academic Press. ISBN 978-1-904455-75-2; pp. 387-412.

Gleba Y. Y. and Giritch A. (2011) Vaccines, antibodies, and pharmaceutical proteins. In Plant Biotechnology and Agriculture. Prospects for the 21st Century. Elsevier Inc. ISBN: 978-0-12-381466-1; pp. 465-476.

Gleba, Y., Klimyuk. V. & Marillonnet, S. (2007). Curr Opin Biotechnol 18, 13441.
Gleba, Y., Marillonnet, S. & Klimyuk, V. (2004). Curr Opin Plant Biol 7, 182-8.
Gleba, Y., Marillonnet, S. & Kiirnyuk, V. (2008). Plant virus vectors (gene expression systems). In Encyclopedia of Virology, Third Edition. M. H. V, van Regenmortel, Mahy. B. W. J., eds. (San Diego, Calif.: Elsevier Academic Press), vol. 4, pp. 229-237.
Giritch, A., Marillonnet, S., Engler, C., van Eldik, a, Botterman, J., Klimyuk, V. & Gleba, Y. (2006). Proc Natl Acad Sci USA 103, 14701-6.
Grant et al., Plant Cell Rep 21 (2003) 1207-1210.
Green, B. J., Fujiki, M., Mett, V., Kaczmarczyk, J., Shamloul, M., Musiychuk, K., Underkoffler, S., Yusibov, V. & Mett, V. (2009). Biotechnol J 4, 230-7.
Huang, Z., Santi, L., LePore, K., Kilbourne, J., Arntzen, C. J. & Mason, H. S. (2006). Vaccine 24, 2506-13.
Jones, H. D., Doherty, A. & Sparks, C. A. (2009). Methods Mol Biol 513, 131-52.
Ko et al, Planta 218 (2004) 536-541.
Lee, M. W. & Yang, Y. (2006). Methods Mol Biol 323, 225-9.
Li, X. Q., Liu, C. N., Ritchie, S. W., Peng, J. Y., Gelvin, S. B. & Hodges, T. K. (1992). Plant Mol Biol 20, 1037-48,
Li, J. F., Park, E., von Arnim, A. G. & Nebenfuhr, A. (2009). Plant Methods 5, 6.
Lindbo, J. A. (2007). TRBO: a high-efficiency tobacco mosaic virus RNA-based overexpression vector. Plant Physiol 145, 1232-40.
Lindbo, J. A. (2007). BMC Biotechnol 7, 52.
Liu, C. N., Li, X. Q. & Gelvin, S. B. (1992). Plant Mol Biol 20, 1071-87.
Lico, C., Chen, Q. & Santi, L (2008). J Cell Physiol 216, 366-77.
Lindbo, J. A. (2007). BMC Biotechnol 7, 52.
Marillonnet, S., Giritch, A., Gils, M., Kandzia, R., Klimyuk, V. & Gleba, Y. (2004). Proc Natl Acad Sci USA 101, 6852-7.
Marillonnet, S., Thoeringer, C Kandzia, R., Klimyuk, V. & Gleba, Y. (2005). Nat Biotechnol 23, 718-23.
Mett, V., Lyons, J., Musiychuk, K., Chichester, J. A., Brasil, T., Couch, R., Sherwood, R., Palmer, G. A., Streatfield, S. J. & Yusibov, V. (2007. Vaccine 25, 3014-7.
Palanichelvam K. et al., Mol Plant Microbe Interact, 2000 October; 13(10):1081-91.
Plesha, M. A., Huang, T. K, Dandekar, A. M., Falk, B. W. & McDonald, K. A. (2007). Biotechnol Prog 23, 1277-85.
Plesha, M. A., Huang, T. K., Dandekar, A. M., Falk, B. W. & McDonald, K. A. (2009). Biotechnol Prog 25, 722-34.
Regnard, G. L., Halley-Stott, R. P., Tanzer, F. L., Hitzeroth, II & Rybicki, E. P. (2010). Plant Biotechnol J 8, 38-46.
Ryu, C. M., Anand, A., Kang, L. & Mysore, K. S. (2004). Plant J 40, 322-31.
Santi, L, Giritch, A., Roy, C. J., Marillonnet, S., Klimyuk, V., Gleba, Y., Webb, R., Arntzen, C. J. & Mason, H. S. (2006). Proc Natl Acad Sci USA 103, 861-6.
Shang, Y., Schwinn, K. E., Bennett, M. J., Hunter, D. A., Waugh, T. L., Pathirana, N. N., Brummell, D. A., Jameson, P. E. & Davies, K. M. (2007). Plant Methods 3, 1.
Shiboleth, Y. M., Arazi, T., Wang, Y. & Gal-On, A. (2001). J Biotechnol 92, 37-46.
Shoji, Y., Farrance, C. E., Bi, H., Shamloul, M., Green, B., Manceva, S., Rhee, A., Ugulava, N., Roy, G., Musiychuk, K., Chichester, J. A., Mett, V. & Yusibov, V. (2009). Vaccine 27, 3467-70.
Simmons, C. W., VanderGheynst, J. S. & Upadhyaya, S. K. (20),Biotechnol Bioeng 102, 965-70.
Sudarshana, M. R., Plesha, M. A., Uratsu, S. L., Falk, B. W., Dandekar, A. M., Huang, T. K. & McDonald, K A. (2006). Plant Biotechnol J 4, 551-9.
Torisky et al, Plant Cell Reports 17 (1997) 102-108.
Vaquero, C., Sack, M., Chandler, J., Drossard, J., Schuster, F., Monecke, M. Schillberg, S. & Fischer, R. (1999). Proc Natl Acad Sci USA 96, 11128-33.
Vezina, L. P., Faye, L, Lerouge, P., D'Aoust, M. A., Marquet-Blouin, E., Burel, C., Lavoie, P. O., Bardor, M. & Gomord, V. (2009). Plant Biotechnol J 7, 442-55.
Voinnet, O., Rivas, S., Mestre, P. & Baulcombe, D. (2003). Plant J 33, 949-56.
Wroblewski, T., Tomczak, A. & Michelmore, R. (2005). Plant Biotechnol J 3, 259-73.
Yang, Y., Li, R & Qi, M. (2000). Plant J 22, 543-51.
Yang, L., Wang, H., Liu, J., Li, L., Fan, Y., Wang, X., Song, Y., Sun, S., Wang, L., Zhu, X. & Wang, X. (2008). J Biotechnol 134, 320-4.
Zambre, M., Terryn, N., De Clercq. J., De Buck, S., Dillon, W., Van Montagu, M., Van Der Straeten, D. & Angenon, G. (2003). Light strongly promotes gene transfer from *Agrobacterium tumefaciens* to plant cells. Planta 216, 580-6.
Zhang, C. & Ghabrial, S. A. (2006). Virology 344, 401-11.
Zhao, M. M., An, D. R., Zhao, J., Huang, G. H., He, Z. H. & Chen. J. Y. (2006). Acta Biochim Biophys Sin (Shanghai) 38, 22-8.

ANNEX

SEQ ID NO: 1:
Amino acid sequence from Agrobacterium LBA4404 virG protein. N54 is shown in bold.
LKHVLLVDDDVANIRHLIIEYLTIHAFKVTAVADSTQFTRVLSSATVDVVV
VDLNLGREDGLEIVRNLAAKSDIPIIIISGDRLEETDKVVALELGASDA
AKPFSIREFLARIRVALRURPNWRSKORRSFCRDWUNLRORRLMSEA
GGEVKLTAGEFNLLLAFLEKPRDVLSREQLLIASRVRDEEVYDRSIDVLI
LRLRRKLEADPSSPOLIKTARGAGYFFDADVQVSHGGTMAA SEQ ID NO: 2:
T-DNA region sequences of pNMD560, pNMD062, pNMD063 pNMD064
cctgtggttggcacatacaaatggacgaacggataaaccttttcacgcccttttaaatatccgattattctaataaacgctcttttctcttaggtttacccgc
caatatatcctgtcaaacactgatagtttaaactgaaggcgggaaacgacaatctgatctaagctagcttggaattggtaccacgcgtttcgacaaa
atttagaacgaacttaattatgatctcaaatacattgatacatatctcatctagatctaggttatcattatgtaagaaagttttgacgaatatggcacgaca
aaatggctagactcgatgtaattggtatctcaactcaacattatacttataccaaacattagttagacaaaatttaaacaactatttttatgtatgcaaga
gtcagcatatgtataattgattcagaatcgttttgacgagttcggatgtagtagtagccattatttaatgtacatactaatcgtgaatagtgaatatgatga
aacattgtatcttattgtataaatatccataaacacatcatgaaagacactttctttcacggtctgaattaattatgatacaattctaatagaaaacgaatt
aaattacgttgaattgtatgaaatctaattgaacaagccaaccacgacgacgactaacgttgcctggattgactcggtttaagttaaccactaaaaaa
acggagctgtcatgtaacacgcggatcgagcaggtcacagtcatgaagccatcaaagcaaaagaactaatccaagggctgagatgattaattag
tttaaaaattagttaacacgagggaaaaggctgtctgacagccaggtcacgttatctttacctgtggtcgaaatgattcgtgtctgtcgattttaattattttt
ttgaaaggccgaaaataaagttgtaagagataaacccgcctatataaattcatatattttcctctccgctttgaagttttagttttattgcaacaacaaca
acaaattacaataacaacaaacaaaatacaaacaacaacaacatggcacaatttcaacaaacaattgacatgcaaactctccaagccgctgcg
ggacgcaacagcttggtgaatgatttggcatctcgtcgcgtttacgataatgcagtcgaggagctgaatgctcgttccagacgtcccaaggtaatag
gaactttctggatctactttatttgctggatctcgatcttgttttctcaatttccttgagatctggaattcgtttaatttggatctgtgaacctccactaaatcttttg
gttttactagaatcgatctaagttgaccgatcagttagctcgattatagctaccagaatttggcttgaccttgatggagagatccatgttcatgttacctgg
gaaatgatttgtatatgtgaattgaaatctgaactgttgaagttagattgaatctgaacactgtcaatgttagattgaatctgaacactgtttaaggttagat
gaagtttgtgtatagattcttcgaaactttaggatttgtagtgtcgtacgttgaacagaaagctatttctgattcaatcagggtttatttgactgtattgaactct
ttttgtgtgtttgcaggtccacttctccaaggcagtgtctacggaacagaccctgattgcaacaaacgcatatccggagttcgagatttcctttactcata
cgcaatccgctgtgcactccttggccggaggccttcggtcacttgagttggagtatctcatgatgcaagttccgttcggttctctgacgtacgacatcgg
cggtaacttttccgcgcaccttttcaaagggcgcgattacgttcactgctgcatgcctaatctggatgtacgtgacattgctcgccatgaaggacacaa
ggaagctatttacagttatgtgaatcgtttgaaaaggcagcagcgtcctgtgcctgaataccagagggcagctttcaacaactacgctgagaaccc
gcacttcgtccattgcgacaaacctttccaacagtgtgaattgacgacagcgtatggcactgacacctacgctgtagctctccatagcatttatgatat
ccctgttgaggagttcggttctgcgctactcaggaagaatgtgaaaacttgtttcgcggcctttcatttccatgagaatatgcttctagattgtgatacagt
cacactcgatgagattggagctacgttccagaaatcaggtaacattccttagttacctttcttttctttttccatcataagtttatagattgtacatgctttgag
atttttctttgcaaacaatctcaggtgataacctgagcttcttcttccataatgagagcactctcaattacacccacagcttcagcaacatcatcaagtac
gtgtgcaagacgttcttccctgctagtcaacgcttcgtgtaccacaaggagttcctggtcactagagtcaacacttggtactgcaagttcacgagagtg
gatacgttcactctgttccgtggtgtgtaccacaacaatgtggattgcgaagagttttacaaggctatggacgatgcgtggcactacaaaaagacgtt
agcaatgcttaatgccgagaggaccatcttcaaggataacgctgcgttaaacttctggttcccgaaggtgctcttgaaattggaagtcttcttttgttgtct
aaacctatcaatttctttgcggaaatttatttgaagctgtagagttaaaattgagtcttttaaacttttgtaggtgagagacatggttatcgtccctctcttga
cgcttctatcacaactggtaggatgtctaggagagaggttatggtgaacaaggacttcgtctacacggtcctaaatcacatcaagacctatcaagct
aaggcactgacgtacgcaaacgtgctgagcttcgtggagtctattaggtctagagtgataattaacggtgtcactgccaggtaagttgttacttatgatt
gttttcctctctgctacatgtatttgttgttcatttctgtaagatataagaattgagttttcctctgatgatattattaggtctgaatgggacacagacaaggca
attctaggtccattagcaatgacattcttcctgatcacgaagctgggtcatgtgcaagatgaaataatcctgaaaaagttccagaagttcgacagaac
caccaatgagctgatttggacaagtctctgcgatgccctgatggggttattccctcggtcaaggagacgcttgtgcgcggtggttttgtgaaagtagc
agaacaagccttagagatcaaggttagtatcatatgaagaaatacctagtttcagttgatgaatgctattttctgacctcagttgttctcttttgagaattatt
tctttctaatttgcctgatttttctattaattcattaggttcccgagctatactgtaccttcgccgaccgattggtactacagtacaagaaggcggaggagtt
ccaatcgtgtgatctttccaaacctctagaagagtcagagaagtactacaacgcattatccgagctatcagtgcttgagaatctcgactcttttgactta
gaggcgtttaagactttatgtcagcagaagaatgtggacccggatatggcagcaaaggtaaatcctggtccacacttttacgataaaaacacaag
attttaaactatgaactgatcaataatcattcctaaaagaccacacttttgttttgtttctaaagtaatttttactgttataacaggtggtcgtagcaatcatga
agtcagaattgacgttgcctttcaagaaacctacagaagaggaaatctcggagtcgctaaaaccaggagaggggtcgtgtgcagagcataagg -continued

| ANNEX |
|---|
| aagtgttgagcttacaaaatgatgctccgttcccgtgtgtgaaaaatctagttgaaggttccgtgccggcgtatggaatgtgtcctaagggtggtggttt |
| cgacaaattggatgtggacattgctgatttccatctcaagagtgtagatgcagttaaaaagggaactatgatgtctgcggtgtacacagggtctatca |
| aagttcaacaaatgaagaactacatagattacttaagtgcgtcgctggcagctacagtctcaaacctctgcaaggtaagaggtcaaaaggtttccg |
| caatgatccctctttttttgtttctctagtttcaagaatttgggtatatgactaacttctgagtgttccttgatgcatatttgtgatgagacaaatgtttgttctatgtt |
| ttaggtgcttagagatgttcacggcgttgacccagagtcacaggagaaatctggagtgtgggatgttaggagaggacgttggttacttaaacctaatg |
| cgaaaagtcacgcgtggggtgtggcagaagacgccaaccacaagttggttattgtgttactcaactgggatgacggaaagccggtttgtgatgag |
| acatggttcagggtggcggtgtcaagcgattccttgatatattcggatatgggaaaacttaagacgctcacgtcttgcagtccaaatggtgagccacc |
| ggagcctaacgccaaagtaattttggtcgatggtgttcccggttgtggaaaaacgaaggagattatcgaaaaggtaagttctgcatttggttatgctcc |
| ttgcattttaggtgttcgtcgctcttccatttccatgaatagctaagatttttttctctgcattcattcttcttgcctcagttctaactgtttgtggtatttttgttttaatt |
| attgctacaggtaaacttctctgaagacttgattttagtccctgggaaggaagcttctaagatgatcatccggagggccaaccaagctggtgtgataa |
| gagcggataaggacaatgttagaacggtggattccttcttgatgcatccttctagaagggtgtttaagaggttgtttatcgatgaaggactaatgctgca |
| tacaggttgtgtaaatttcctactgctgctatctcaatgtgacgtcgcatatgtgtatggggacacaaagcaaattccgttcatttgcagagtcgcgaact |
| ttccgtatccagcgcattttgcaaaactcgtcgctgatgagaaggaagtcagaagagttacgctcaggtaaagcaactgtgttttaatcaatttcttgtc |
| aggatatatggattataacttaattttgagaaatctgtagtatttggcgtgaaatgagtttgctttttggtttctcccgtgttataggtgcccggctgatgttac |
| gtatttccttaacaagaagtatgacggggcggtgatgtgtaccagcgcggtagagagatccgtgaaggcagaagtggtgagaggaaagggtgca |
| ttgaacccaataaccttaccgttggagggtaaaattttgaccttcacacaagctgacaagttcgagttactggagaagggttacaaggtaaagtttcc |
| aactttcctttaccatatcaaactaaagttcgaaactttttatttgatcaacttcaaggccacccgatctttctattcctgattaatttgtgatgaatccatattg |
| acttttgatggttacgcaggatgtgaacactgtgcacgaggtgcaaggggagacgtacgagaagactgctattgtgcgcttgacatcaactccgtta |
| gagatcatatcgagtgcgtcacctcatgttttggtggcgctgacaagacacacaacgtgttgtaaatattacaccgttgtgttggacccgatggtgaat |
| gtgatttcagaaatggagaagttgtccaatttccttcttgacatgtatagagttgaagcaggtctgtctttcctatttcatatgtttaatcctaggaatttgatc |
| aattgattgtatgtatgtcgatcccaagactttcttgttcacttatatcttaactctctcttgctgtttcttgcaggtgtccaatagcaattacaaatcgatgca |
| gtattcaggggacagaacttgtttgttcagacgcccaagtcaggagattggcgagatatgcaattttactatgacgctcttcttcccggaaacagtact |
| attctcaatgaatttgatgctgttacgatgaatttgagggatatttccttaaacgtcaaagattgcagaatcgacttctccaaatccgtgcaacttcctaaa |
| gaacaacctattttcctcaagcctaaaataagaactgcggcagaaatgccgagaactgcaggtaaaatattggatgccagacgatattctttctttg |
| atttgtaactttttcctgtcaaggtcgataaatttttattttttttggtaaaaggtcgataatttttttttggagccattatgtaattttcctaattaactgaaccaaaat |
| tatacaaaccaggtttgctggaaaatttggttgcaatgatcaaaagaaacatgaatgcgccggatttgacagggacaattgacattgaggatactgc |
| atctctggtggttgaaaagttttgggattcgtatgttgacaaggaatttagtggaacgaacgaaatgaccatgacaagggagagcttctccaggtaag |
| gacttctcatgaatattagtggcagattagtgttgttaaagtctttggttagataatcgatgcctcctaattgtccatgttttactggtttctacaattaaaggt |
| ggctttcgaaacaagagtcatctacagttggtcagttagcggactttaactttgtggatttgccggcagtagatgagtacaagcatatgatcaagagtc |
| aaccaaagcaaaagttagacttgagtattcaagacgaatatcctgcattgcagacgatagtctaccattcgaaaaagatcaatgcgattttcggtcc |
| aatgttttcagaacttacgaggatgttactcgaaaggattgactcttcgaagtttctgttctacaccagaaagacacctgcacaaatagaggacttcttt |
| ctgacctagactcaacccaggcgatggaaattctggaactcgacatttcgaagtacgataagtcacaaaacgagttccattgtgctgtagagtaca |
| agatctgggaaaagttaggaattgatgagtggctagctgaggtctggaaacaaggtgagttcctaagttccatttttttgtaatccttcaatgttattttaac |
| ttttcagatcaacatcaaaattaggttcaattttcatcaaccaaataatatttttcatgtatatataggtcacagaaaaacgaccttgaaagattatacgg |
| ccggaatcaaaacatgtctttggtatcaaaggaaaagtggtgatgtgacaacctttattggtaataccatcatcattgccgcatgtttgagctcaatgat |
| ccccatggacaaagtgataaaggcagctttttgtggagacgatagcctgatttacattcctaaaggtttagacttgcctgatattcaggcgggcgcga |
| acctcatgtggaacttcgaggccaaactcttcaggaagaagtatggttacttctgtggtcgttatgttattcaccatgatagaggagccattgtgtattac |
| gatccgcttaaactaatatctaagttaggttgtaaacatattagagatgttgttcacttagaagagttacgcgagtctttgtgtgatgtagctagtaacttaa |
| ataattgtgcgtattttcacagttagatgaggccgttgccgaggttcataagaccgcggtaggcggttcgtttgctttttgtagtataattaagtatttgtca |
| gataagagattgtttagagatttgttctttgtttgataatgtcgatagtctcgtacgaacctaaggtgagtgatttcctcaatctttcgaagaaggaagaga |
| tcttgccgaaggctctaacgaggttaaaaaccgtgtctattagtactaaagatattatatctgtcaaggagtcggagactttgtgtgatatagatttgttaa |
| tcaatgtgccattagataagtatagatatgtgggtatcctaggagccgtttttaccggagagtggctagtgccagacttcgttaaaggtggagtgacga |
| taagtgtgatagataagcgtctggtgaactcaaaggagtgcgtgattggtacgtacagagccgcagccaagagtaagaggttccagttcaaattgg |
| ttccaaattactttgtgtccaccgtggacgcaaagaggaagccgtggcaggtaaggatttttatgatatagtatgcttatgtattttgtactgaaagcatat |
| cctgcttcattgggatattactgaaagcatttaactacatgtaaactcacttgatgatcaataaacttgattttgcaggttcatgttcgtatacaagacttga |
| agattgaggcgggttggcagccgttagctctggaagtagtttcagttgctatggtcaccaataacgttgtcatgaagggtttgagggaaaaggtcgtc |
| gcaataaatgatccggacgtcgaaggtttcgaaggtaagccatcttcctgcttatttttataatgaacatagaaataggaagttgtgcagagaaacta |
| attaacctgactcaaaatctaccctcataattgttgtttgatattggtcttgtattttgcaggtgtggttgacgaattcgtcgattcggttgcagcatttaaagc |
| ggttgacaactttaaaagaaggaaaaagaaggttgaagaaaagggtgtagtaagtaagtataagtacagaccggagaagtacgccggtcctga |
| ttcgtttaatttgaaagaagaaaacgtcttacaacattacaaacccgaataatcgataactcgagtatttttacaacaattaccaacaacaacaaaca |
| acaaacaacattacaattacatttacaattatcatggtgagcaagggcgaggagctgttcaccggggtggtgcccatcctggtcgagctggacggc |

-continued

ANNEX gacgtaaacggccacaagttcagcgtgtccggcgagggcgagggcgatgccacctacggcaagctgaccctgaagttcatctgcaccaccggc
aagctgcccgtgccctggcccaccctcgtgaccaccttcagctacggcgtgcagtgcttcagccgctaccccgaccacatgaagcagcacgactt
cttcaagtccgccatgcccgaaggctacgtccaggagcgcaccatcttcttcaaggacgacggcaactacaagacccgcgccgaggtgaagttc
gagggcgacaccctggtgaaccgcatcgagctgaagggcatcgacttcaaggaggacggcaacatcctggggcacaagctggagtacaact
acaacagccacaacgtctatatcatggccgacaagcagaagaacggcatcaaggtgaacttcaagatccgccacaacatcgaggacggcag
cgtgcagctcgccgaccactaccagcagaacacccccatcggcgacggccccgtgctgctgcccgacaaccactacctgagcacccagtccg
ccctgagcaaagaccccaacgagaagcgcgatcacatggtcctgctggagttcgtgaccgccgccgggatcactcacggcatggacgagctgt
acaagtaaagcggcccctagagcgtggtgcgcacgatagcgcatagtgtttttctctccacttgaatcgaagagatagacttacggtgtaaatccgt
aggggtggcgtaaaccaaattacgcaatgttttgggttccatttaaatcgaaaccccttatttcctggatcacctgttaacgcacgtttgacgtgtattac
agtgggaataagtaaaagtgagaggttcgaatcctccctaaccccgggtaggggcccagcggccgctctagctagagtcaagcagatcgttcaa
acatttggcaataaagtttcttaagattgaatcctgttgccggtcttgcgatgattatcatataatttctgttgaattacgttaagcatgtaataattaacatgt
aatgcatgacgttatttatgagatgggtttttatgattagagtcccgcaattatacatttaatacgcgatagaaaacaaaatatagcgcgcaaactagg
ataaattatcgcgcgcggtgtcatctatgttactagatcgacctgcatccaccccagtacattaaaaacgtccgcaatgtgttattaagttgtcataagcg
tcaatttgfttacacc matatatcctgccaccagccaccac ccc ac gcagctcggcac atcaccactcgatacaggcagc
ccatcac SEQ ID NO: 3:
Sequence of T-DNA region of pNMD570
cctgtggttggcacatacaaatggacgaacggataaaccttttcacgcccttttaaatatccgattattctaataaacgctcttttctcttaggtttacccgc
caatatatcctgtcaaacactgatagtttaaactgaaggcgggaaacgacaatctgatctaagctagcttggaattggtaccacgcgtttcgacaaa
atttagaacgaacttaattatgatctcaaatacattgatacatatctcatctagatctaggttatcattatgtaagaaagttttgacgaatatggcacgaca
aaatggctagactcgatgtaattggtatctcaactcaacattatacttataccaaacattagttagacaaaatttaaacaactatttttatgtatgcaaga
gtcagcatatgtataattgattcagaatcgttttgacgagttcggatgtagtagtagccattatttaatgtacatactaatcgtgaatagtgaatatgatga
aacattgtatcttattgtataaatatccataaacacatcatgaaagacactttctttcacggtctgaattaattatgatacaattctaatagaaaacgaatt
aaattacgttgaattgtatgaaatctaattgaacaagccaaccacgacgacgactaacgttgcctggattgactcggtttaagttaaccactaaaaaa
acggagctgtcatgtaacacgcggatcgagcaggtcacagtcatgaagccatcaaagcaaaagaactaatccaagggctgagatgattaattag
tttaaaaattagttaacacgagggaaaaggctgtctgacagccaggtcacgttatctttacctgtggtcgaaatgattcgtgtctgtcgattttaattattttt
ttgaaaggccgaaaataaagttgtaagagataaacccgcctatataaattcatatattttcctctccgctttgaagttttagttttattgcaacaacaaca
acaaattacaataacaacaaacaaaatacaaacaacaacaacatggcacaatttcaacaaacaattgacatgcaaactctccaagccgctgcg
ggacgcaacagcttggtgaatgatttggcatctcgtcgcgtttacgataatgcagtcgaggagctgaatgctcgttccagacgtcccaaggtaatag
gaactttctggatctactttatttgctggatctcgatcttgttttctcaatttccttgagatctggaattcgtttaatttggatctgtgaacctccactaaatcttttg
gttttactagaatcgatctaagttgaccgatcagttagctcgattatagctaccagaatttggcttgaccttgatggagagatccatgttcatgttacctgg
gaaatgatttgtatatgtgaattgaaatctgaactgttgaagttagattgaatctgaacactgtcaatgttagattgaatctgaacactgtttaaggttagat
gaagtttgtgtatagattcttcgaaactttaggatttgtagtgtcgtacgttgaacagaaagctatttctgattcaatcagggtttatttgactgtattgaactct
ttttgtgtgtttgcaggtccacttctccaaggcagtgtctacggaacagaccctgattgcaacaaacgcatatccggagttcgagatttcctttactcata
cgcaatccgctgtgcactccttggccggaggccttcggtcacttgagttggagtatctcatgatgcaagttccgttcggttctctgacgtacgacatcgg
cggtaacttttccgcgcaccttttcaaagggcgcgattacgttcactgctgcatgcctaatctggatgtacgtgacattgctcgccatgaaggacacaa
ggaagctatttacagttatgtgaatcgtttgaaaaggcagcagcgtcctgtgcctgaataccagagggcagctttcaacaactacgctgagaaccc
gcacttcgtccattgcgacaaacctttccaacagtgtgaattgacgacagcgtatggcactgacacctacgctgtagctctccatagcatttatgatat
ccctgttgaggagttcggttctgcgctactcaggaagaatgtgaaaacttgtttcgcggcctttcatttccatgagaatatgcttctagattgtgatacagt
cacactcgatgagattggagctacgttccagaaatcaggtaacattccttagttacctttcttttctttttccatcataagtttatagattgtacatgctttgag
atttttctttgcaaacaatctcaggtgataacctgagcttcttcttccataatgagagcactctcaattacacccacagcttcagcaacatcatcaagtac
gtgtgcaagacgttcttccctgctagtcaacgcttcgtgtaccacaaggagttcctggtcactagagtcaacacttggtactgcaagttcacgagagtg
gatacgttcactctgttccgtggtgtgtaccacaacaatgtggattgcgaagagttttacaaggctatggacgatgcgtggcactacaaaaagacgtt
agcaatgcttaatgccgagaggaccatcttcaaggataacgctgcgttaaacttctggttcccgaaggtgctcttgaaattggaagtcttcttttgttgtct
aaacctatcaatttctttgcggaaatttatttgaagctgtagagttaaaattgagtcttttaaacttttgtaggtgagagacatggttatcgtccctctctttga
cgcttctatcacaactggtaggatgtctaggagagaggttatggtgaacaaggacttcgtctacacggtcctaaatcacatcaagacctatcaagct
aaggcactgacgtacgcaaacgtgctgagcttcgtggagtctattaggtctagagtgataattaacggtgtcactgccaggtaagttgttacttatgatt
gttttcctctctgctacatgtattttgttgttcatttctgtaagatataagaattgagttttcctctgatgatattattaggtctgaatgggacacagacaaggca
attctaggtccattagcaatgacattcttctgatcacgaagctgggtcatgtgcaagatgaaataatcctgaaaagttccgaagttcgacagaac
caccaatgagctgatttggacaagtctctgcgatgccctgatggggttattccctcggtcaaggagacgcttgtgcgcggtggttttgtgaaagtagc -continued

| ANNEX |
|---|
| agaacaagccttagagatcaaggttagtatcatatgaagaaatacctagtttcagttgatgaatgctattttctgacctcagttgttctcttttgagaattatt |
| tcttttctaatttgcctgattttctattaattcattaggttcccgagctatactgtaccttcgccgaccgattggtactacagtacaagaaggcggaggagtt |
| ccaatcgtgtgatctttccaaacctctagaagagtcagagaagtactacaacgcattatccgagctatcagtgcttgagaatctcgactcttttgatta |
| gaggcgtttaagactttatgtcagcagaagaatgtggacccggatatggcagcaaaggtaaatcctggtccacacttttacgataaaaacacaag |
| attttaaactatgaactgatcaataatcattcctaaaagaccacacacttttgttttgtttctaaagtaatttttactgttataacaggtggtcgtagcaatcatga |
| agtcagaattgacgttgcctttcaagaaacctacagaagaggaaatctcggagtcgctaaaaccaggagaggggtcgtgtgcagagcataagg |
| aagtgttgagcttacaaaatgatgctccgttcccgtgtgtgaaaaatctagttgaaggttccgtgccggcgtatggaatgtgtcctaagggtggtggttt |
| cgacaaattggatgtggacattgctgatttccatctcaagagtgtagatgcagttaaaaagggaactatgatgtctgcggtgtacacagggtctatca |
| aagttcaacaaatgaagaactacatagattacttaagtgcgtcgctggcagctacagtctcaaacctctgcaaggtaagaggtcaaaaggtttccg |
| caatgatccctctttttttgtttctctagtttcaagaatttgggtatatgactaacttctgagtgttccttgatgcatatttgtgatgagacaaatgtttgttctatgtt |
| ttaggtgcttagagatgttcacggcgttgacccagagtcacaggagaaatctggagtgtgggatgttaggagaggacgttggttacttaaacctaatg |
| cgaaaagtcacgcgtggggtgtggcagaagacgccaaccacaagttggttattgtgttactcaactgggatgacggaaagccggtttgtgatgag |
| acatggttcagggtggcggtgtcaagcgattccttgatatattcggatatgggaaaacttaagacgctcacgtcttgcagtccaaatggtgagccacc |
| ggagcctaacgccaaagtaattttggtcgatggtgttcccggttgtggaaaaacgaaggagattatcgaaaaggtaagttctgcatttggttatgctcc |
| ttgcatttaggtgttcgtcgctcttccatttccatgaatagctaagatttttttctctgcattcattcttcttgcctcagttctaactgtttgtggtatttttgttttaatt |
| attgctacaggtaaacttctctgaagacttgattttagtccctgggaaggaagcttctaagatgatcatccggagggccaaccaagctggtgtgataa |
| gagcggataaggacaatgttagaacggtggattccttcttgatgcatccttctagaagggtgtttaagaggttgtttatcgatgaaggactaatgctgca |
| tacaggttgtgtaaatttcctactgctgctatctcaatgtgacgtcgcatatgtgtatggggacacaaagcaaattccgttcatttgcagagtcgcgaact |
| ttccgtatccagcgcattttgcaaaactcgtcgctgatgagaaggaagtcagaagagttacgctcaggtaaagcaactgtgttttaatcaatttcttgtc |
| aggatatatggattataacttaattttgagaaatctgtagtatttggcgtgaaatgagtttgctttttggtttctcccgtgttataggtgcccggctgatgttac |
| gtatttccttaacaagaagtatgacggggcggtgatgtgtaccagcgcggtagagagatccgtgaaggcagaagtggtgagaggaaagggtgca |
| ttgaacccaataaccttaccgttggagggtaaaatttgaccttcacacaagctgacaagttcgagttactggagaagggttacaaggtaaagtttcc |
| aactttcctttaccatatcaaactaaagttcgaaacttttatttgatcaacttcaaggccacccgatctttctattcctgattaatttgtgatgaatccatattg |
| acttttgatggttacgcaggatgtgaacactgtgcacgaggtgcaaggggagacgtacgagaagactgctattgtgcgcttgacatcaactccgtta |
| gagatcatatcgagtgcgtcacctcatgttttggtggcgctgacaagacacacaacgtgttgtaaatattacaccgttgtgttggacccgatggtgaat |
| gtgatttcagaaatggagaagttgtccaatttccttcttgacatgtatagagttgaagcaggtctgtctttcctatttcatatgtttaatcctaggaatttgatc |
| aattgattgtatgtatgtcgatcccaagactttcttgttcacttatatcttaactctctctttgctgtttcttgcaggtgtccaatagcaattacaaatcgatgca |
| gtattcaggggacagaacttgtttgttcagacgcccaagtcaggagattggcgagatatgcaattttactatgacgctcttcttcccggaaacagtact |
| attctcaatgaatttgatgctgttacgatgaatttgagggatatttccttaaacgtcaaagattgcagaatcgacttctccaaatccgtgcaacttcctaaa |
| gaacaacctattttcctcaagcctaaaataagaactgcggcagaaatgccgagaactgcaggtaaaatattggatgccagacgatattctttcttttg |
| atttgtaactttttcctgtcaaggtcgataaattttatttttttggtaaaaggtcgataattttttttggagccattatgtaattttcctaattaactgaaccaaaat |
| tatacaaaccaggtttgctggaaaatttggttgcaatgatcaaaagaaacatgaatgcgccggatttgacagggacaattgacattgaggatactgc |
| atctctggtggttgaaaagttttgggattcgtatgttgacaaggaatttagtggaacgaacgaaatgaccatgacaagggagagcttctccaggtaag |
| gacttctcatgaatattagtggcagattagtgttgttaaagtctttggttagataatcgatgcctcctaattgtccatgttttactggttttctacaattaaaggt |
| ggctttcgaaacaagagtcatctacagttggtcagttagcggactttaactttgtggatttgccggcagtagatgagtacaagcatatgatcaagagtc |
| aaccaaagcaaaagttagacttgagtattcaagacgaatatcctgcattgcagacgatagtctaccattcgaaaaagatcaatgcgattttcggtcc |
| aatgttttcagaacttacgaggatgttactcgaaaggattgactcttcgaagtttctgttctacaccagaaagacacctgcacaaatagaggacttctttt |
| ctgacctagactcaacccaggcgatggaaattctggaactcgacatttcgaagtacgataagtcacaaaacgagttccattgtgctgtagagtaca |
| agatctgggaaaagttaggaattgatgagtggctagctgaggtctggaaacaaggtgagttcctaagttccatttttttgtaatccttcaatgttattttaac |
| ttttcagatcaacatcaaaattaggttcaattttcatcaaccaaataatatttttcatgtatatataggtcacagaaaaacgaccttgaaagattatacgg |
| ccggaatcaaaacatgtctttggtatcaaaggaaaagtggtgatgtgacaacctttattggtaataccatcatcattgccgcatgtttgagctcaatgat |
| ccccatggacaaagtgataaaggcagctttttgtggagacgatagcctgatttacattcctaaaggtttagacttgcctgatattcaggcgggcgcga |
| acctcatgtggaacttcgaggccaaactcttcaggaagaagtatggttacttctgtggtcgttatgttattcaccatgatagaggagccattgtgtattac |
| gatccgcttaaactaatatctaagttaggttgtaaacatattagagatgttgttcacttagaagagttacgcgagtctttgtgtgatgtagctagtaacttaa |
| ataattgtgcgtatttttcacagttagatgaggccgttgccgaggttcataagaccgcggtaggcggttcgtttgctttttgtagtataattaagtatttgtca |
| gataagagattgtttagagattgttctttgtttgataatgtcgatagtctcgtacgaacctaaggtgagtgatttcctcaatctttcgaagaaggaagaga |
| tcttgccgaaggctctaacgaggttaaaaaccgtgtctattagtactaaagatattatatctgtcaaggagtcggagactttgtgtgatatagatttgttaa |
| tcaatgtgccattagataagtatagatatgtgggtatcctagctaggagccgtttttaccggagagtggctagtgccagacttcgttaaaggtggagtg |
| acgataagtgtgatagataagcgtctggtgaactcaaaggagtgcgtgattggtacgtacagagccgcagccaagagtaagaggttccagttcaa |
| attggttccaaattactttgtgtccaccgtggacgcaaagaggaagccgtggcaggtaaggattttatgatatagtatgcttatgtattttgtactgaaag |
| catatcctgcttcattgggatattactgaaagcatttaactacatgtaaactcacttgatgatcaataaacttgattttgcaggttcatgttcgtatacaaga |

-continued

ANNEX cttgaagattgaggcgggttggcagccgttagctctggaagtagtttcagttgctatggtcaccaataacgttgtcatgaagggtttgagggaaaaggt
cgtcgcaataaatgatccggacgtcgaaggtttcgaaggtaagccatcttcctgcttatttttataatgaacatagaaataggaagttgtgcagagaa
actaattaacctgactcaaaatctaccctcataattgttgtttgatattggtcttgtattttgcaggtgtggttgacgaattcgtcgattcggttgcagcattta
aagcggttgacaactttaaaagaaggaaaaagaaggttgaagaaaagggtgtagtaagtaagtataagtacagaccggagaagtacgccggt
cctgattcgtttaatttgaaagaagaaaacgtcttacaacattacaaacccgaataatcgataactcgagtatttttacaacaattaccaacaacaac
aaacaacaaacaacattacaattacatttacaattatcatggtgagcaagggcgaggagctgttcaccggggtggtgcccatcctggtcgagctgg
acggcgacgtaaacggccacaagttcagcgtgtccggcgagggcgagggcgatgccacctacggcaagctgaccctgaagttcatctgcacc
accggcaagctgcccgtgccctggcccaccctcgtgaccaccttcagctacggcgtgcagtgcttcagccgctaccccgaccacatgaagcagc
acgacttcttcaagtccgccatgcccgaaggctacgtccaggagcgcaccatcttcttcaaggacgacggcaactacaagacccgcgccgaggt
gaagttcgagggcgacaccctggtgaaccgcatcgagctgaagggcatcgacttcaaggaggacggcaacatcctggggcacaagctggagt
acaactacaacagccacaacgtctatatcatggccgacaagcagaagaacggcatcaaggtgaacttcaagatccgccacaacatcgaggac
ggcagcgtgcagctcgccgaccactaccagcagaacacccccatcggcgacggccccgtgctgctgcccgacaaccactacctgagcaccc
agtccgccctgagcaaagaccccaacgagaagcgcgatcacatggtcctgctggagttcgtgaccgccgccgggatcactcacggcatggacg
agctgtacaagtaaagcggcccctagagcgtggtgcgcacgatagcgcatagtgtttttctctccacttgaatcgaagagatagacttacggtgtaa
atccgtaggggtggcgtaaaccaaaattacgcaatgttttgggttccatttaaatcgaaaccccttatttcctggatcacctgttaacgcacgtttgacgtg
tattacagtgggaataagtaaaagtgagaggttcgaatcctccctaaccccgggtaggggcccagcggccgctctagctagagtcaagcagatc
gttcaaacatttggcaataaagtttcttaagattgaatcctgttgccggtcttgcgatgattatcatataatttctgttgaattacgttaagcatgtaataatta
acatgtaatgcatgacgttatttatgagatgggtttttatgattagagtcccgcaattatacatttaatacgcgatagaaaacaaaatatagcgcgcaaa
ctaggataaattatcgcgcgcggtgtcatctatgttactagatcgacctgcatccaccccagtacattaaaaacgtccgcaatgtgttattaagttgtct
aagcgtcaatttgtttacaccacaatatatcctgccaccagccagccaacagctccccgaccggcagctcggcacaaaatcaccactcgataca
ggcagcccatcag SEQ ID NO: 4:
Sequence of T-DNA region of pNMD620
cctgtggttggcacatacaaatggacgaacggataaaccttttcacgcccttttaaatatccgattattctaataaacgctcttttctcttaggtttacccgc
caatatatcctgtcaaacactgatagtttaaactgaaggcgggaaacgacaatctgatctaagctaggcatgcctgcaggtcaacatggtggagca
cgacacgcttgtctactccaaaaatatcaaagatacagtctcagaagaccaaagggcaattgagacttttcaacaaagggtaatatccggaaacc
tcctcggattccattgcccagctatctgtcactttattgtgaagatagtggaaaaggaaggtggctcctacaaatgccatcattgcgataaaggaaac
gccatcgttgaagatgcctctgccgacagtggtcccaaagatggacccccacccacgaggagcatcgtggaaaaagaagacgttccaaccac
gtcttcaaagcaagtggattgatgtgatatctccactgacgtaagggatgacgcacaatcccactatccttcgcaagacccttcctctatataaggaa
gttcatttcatttggagaggagaaaactaaaccatacaccaccaacacaaccaaacccaccacgcccaattgttacacacccgcttgaaaaaga
aagtttaacaaatggccaaggtgcgcgaggtttaccaatcttttacagactccaccacaaaaactctccatccaagatgaggcttatagaaacattcg
ccccatcatggaaaaacacaaactagctaacccttacgctcaaacggttgaagcggctaatgatctagaggggttcggcatagccaccaatccct
atagcattgaattgcatacacatgcagccgctaagaccatagagaataaacttctagaggtgcttggttccatcctaccacaagaacctgttacattt
atgtttcttaaacccagaaagctaaactacatgagaagaaacccgcggatcaaggacattttccaaaatgttgccattgaaccaagagacgtagc
caggtaccccaaggaaacaataattgacaaactcacagagatcacaacggaaacagcatacattagtgacactctgcacttcttggatccgagct
acatagtggagacattccaaaactgcccaaaattgcaaacattgtatgcgaccttagttctccccgttgaggcagcctttaaaatggaaagcactca
cccgaacatatacagcctcaaatacttcggagatggtttccagtatataccaggcaaccatggtggcggggcataccatcatgaattcgctcatcta
caatggctcaaagtgggaaagatcaagtggagggaccccaaggatagctttctcggacatctcaattacacgactgagcaggttgagatgcaca
cagtgacagtacagttgcaggaatcgttcgcggcaaaccacttgtactgcatcaggagaggagacttgctcacaccggaggtgcgcactttcggc
caacctgacaggtacgtgattccaccacagatcttcctcccaaaagttcacaactgcaagaagccgattctcaagaaaactatgatgcagctcttct
tgtatgttaggacagtcaaggtcgcaaaaaaattgtgacatttttgccaaagtcagacaattaattaaatcatctgacttggacaaatactctgctgtgga
actggtttacttagtaagctacatggagttccttgccgatttacaagctaccacctgcttctcagacacactttctggtggcttgctaacaaagacccttg
caccggtgagggcttggatacaagagaaaaagatgcagctgtttggtcttgaggactacgcgaagttagtcaaagcagttgatttccacccggtgg
atttttctttcaaagtggaaacttgggacttcagattccaccccttgcaagcgtggaaagccttccgaccaagggaagtgtcggatgtagaggaaatg
gaaagtttgttctcagatggggacctgcttgattgcttcacaagaatgccagcttatgcggtaaacgcagaggaagatttagctgcaatcaggaaaa
cgcccgagatggatgtcggtcaagaagttaaagagcctgcaggagacagaaatcaatactcaaaccctgcagaaactttcctcaacaagctcca
caggaaacacagtagggaggtgaaacaccaggccgcaaagaaagctaaacgcctagctgaaatccaggagtcaatgagagctgaaggtga
tgccgaaccaaatgaaataagcgggacgatgggggcaatacccagcaacgccgaacttcctggcacgaatgatgccagacaagaactcaca
ctcccaaccactaaacctgtccctgcaaggtgggaagatgcttcattcacagattctagtgtggaagaggagcaggttaaactccttggaaaagaa
accgttgaaacagcgacgcaacaagtcatcgaaggacttccttggaaacactggattcctcaattaaatgctgttggattcaaggcgctggaaattc -continued

| ANNEX |
| --- |
| agagggataggagtggaacaatgatcatgcccatcacagaaatggtctccgggctggaaaaagaggacttccctgaaggaactccaaaagag |
| ttggcacgagaattgttcgctatgaacagaagccctgccaccatccctttggacctgcttagagccagagactacggcagtgatgtaaagaacaa |
| gagaattggtgccatcacaaagacacaggcaacgagttggggcgaatacttgacaggaaagatagaaagcttaactgagaggaaagttgcga |
| cttgtgtcattcatggagctggaggttctggaaaaagtcatgccatccagaaggcattgagagaaattggcaagggctcggacatcactgtagtcct |
| gccgaccaatgaactgcggctagattggagtaagaaagtgcctaacactgagccctatatgttcaagacctctgaaaaggcgttaattgggggaa |
| caggcagcatagtcatctttgacgattactcaaaacttcctcccggttacatagaagccttagtctgtttctactctaaaatcaagctaatcattctaaca |
| ggagatagcagacaaagcgtctaccatgaaactgctgaggacgcctccatcaggcatttgggaccagcaacagagtacttctcaaaatactgcc |
| gatactatctcaatgccacacaccgcaacaagaaagatcttgcgaacatgcttggtgtctacagtgagagaacgggagtcaccgaaatcagcat |
| gagcgccgagttcttagaaggaatcccaactttggtaccctcggatgagaagagaaagctgtacatgggcaccgggaggaatgacacgttcaca |
| tacgctggatgccaggggctaactaagccgaaggtacaaatagtgttggaccacaacacccaagtgtgtagcgcgaatgtgatgtacacggcac |
| tttctagagccaccgataggattcacttcgtgaacacaagtgcaaattcctctgccttctgggaaaagttggacagcaccccttacctcaagactttcc |
| tatcagtggtgagagaacaagcactcagggagtacgagccggcagaggcagagccaattcaagagcctgagccccagacacacatgtgtgtc |
| gagaatgaggagtccgtgctagaagagtacaaagaggaactcttggaaaagtttgacagagagatccactctgaatcccatggtcattcaaactg |
| tgtccaaactgaagacacaaccattcagttgttttcgcatcaacaagcaaaagatgagaccctcctctgggcgactatagatgcgcggctcaagac |
| cagcaatcaagaaacaaacttccgagaattcctgagcaagaaggacattggggacgttctgtttttaaactaccaaaaagctatgggtttacccaa |
| agagcgtattcctttttcccaagaggtctgggaagcttgtgcccacgaagtacaaagcaagtacctcagcaagtcaaagtgcaacttgatcaatgg |
| gactgtgagacagagcccagacttcgatgaaaataagattatggtattcctcaagtcgcagtgggtcacaaaggtggaaaaactaggtctaccca |
| agattaagccaggtcaaaccatagcagccttttaccagcagactgtgatgcttttggaactatggctaggtacatgcgatggttcagacaggctttcc |
| agccaaaagaagtcttcataaactgtgagaccacgccagatgacatgtctgcatgggccttgaacaactggaatttcagcagacctagcttggcta |
| atgactacacagctttcgaccagtctcaggatggagccatgttgcaatttgaggtgctcaaagccaaacaccactgcataccagaggaaatcattc |
| aggcatacatagatattaagactaatgcacagattttcctaggcacgttatcaattatgcgcctgactggtgaaggtcccacttttgatgcaaacactg |
| agtgcaacatagcttacacccatacaaagtttgacatcccagccggaactgctcaagtttatgcaggagacgactccgcactggactgtgttccag |
| aagtgaagcatagtttccacaggcttgaggacaaattactcctaaagtcaaagcctgtaatcacgcagcaaaagaagggcagttggcctgagtttt |
| gtggttggctgatcacaccaaaaggggtgatgaaagacccaattaagctccatgttagcttaaaattggctgaagctaagggtgaactcaagaaat |
| gtcaagattcctatgaaattgatctgagttatgcctatgaccacaaggactctctgcatgacttgttcgatgagaaacagtgtcaggcacacacactc |
| acttgcagaacactaatcaagtcagggagaggcactgtctcactttcccgcctcagaaactttctttcaaccgttaagttaccttgagatttgaataag |
| atggatattctcatcagtagtttgaaaagtttaggttattctaggacttccaaatctttagattcaggacctttggtagtacatgcagtagccggagccggt |
| aagtccacagccctaaggaagttgatcctcagacacccaacattcaccgtgcatacactcggtgtccctgacaaggtgagtatcagaactagagg |
| catacagaagccaggacctattcctgagggcaacttcgcaatcctcgatgagtatactttggacaacaccacaaggaactcataccaggcactttttt |
| gctgacccttatcaggcaccggagtttagcctagagccccacttctacttggaaacatcatttcgagttccgaggaaagtggcagatttgatagctgg |
| ctgtggcttcgatttcgagacgaactcaccggaagaagggcacttagagatcactggcatattcaaagggcccctactcggaaaggtgatagcca |
| ttgatgaggagtctgagacaacactgtccaggcatggtgttgagtttgttaagccctgccaagtgacgggacttgagttcaaagtagtcactattgtgt |
| ctgccgcaccaatagaggaaattggccagtccacagctttctacaacgctatcaccaggtcaaagggattgacatatgtccgcgcagggccatag |
| gctgaccgctccggtcaattctgaaaagtgtacatagtattaggtctatcatttgctttagtttcaattacctttctgctttctagaaatagcttaccccacg |
| tcggtgacaacattcacagcttgccacacggaggagcttacagagacggcaccaaagcaatcttgtacaactccccaaatctagggtcacgagt |
| gagtctacacaacggaaagaacgcagcatttgctgccgttttgctactgactttgctgatctatggaagtaaatacatatctcaacgcaatcatacttgt |
| gcttgtggtaacaatcatagcagtcattagcacttccttagtgaggactgaaccttgtgtcatcaagattactggggaatcaatcacagtgttggcttgc |
| aaactagatgcagaaaccataagggccattgccgatctcaagccactctccgttgaacggttaagtttccattgatactcgaaagaggtcagcacc |
| agctagcaacaaacaagaaaggtatggtgagcaagggcgaggagctgttcaccggggtggtgcccatcctggtcgagctggacggcgacgta |
| aacggccacaagttcagcgtgtccggcgagggcgagggcgatgccacctacggcaagctgaccctgaagttcatctcgcaccaccggaagctg |
| cccgtgccctggcccaccctcgtgaccaccttcagctacggcgtgcagtgcttcagccgctaccccgaccacatgaagcagcacgacttcttcaa |
| gtccgccatgcccgaaggctacgtccaggagcgcaccatcttcttcaaggacgacggcaactacaagacccgcgccgaggtgaagttcgaggg |
| cgacaccctggtgaaccgcatcgagctgaagggcatcgacttcaaggaggacggcaacatcctggggcacaagctggagtacaactacaaca |
| gccacaacgtctatatcatggccgacaagcagaagaacggcatcaaggtgaacttcaagatccgccacaacatcgaggacggcagcgtgcag |
| ctcgccgaccactaccagcagaacacccccatcggcgacggccccgtgctgctgcccgacaaccactacctgagcacccagtccgccctgag |
| caaagaccccaacgagaagcgcgatcacatggtcctgctggagttcgtgaccgccgccgggatcactcacggcatggacgagctgtacaagta |
| agcttggtcgtatcactggaacaacaaccgctgaggctgttgtcactctaccaccaccataactacgtctacataaccgacgcctaccccagtttcat |
| agtattttctggtttgattgtatgaataatataaataaaaaaaaaaaaaaaaaaaaaactagtgagctcttctgtcagcgggcccactgcatccac |
| cccagtacattaaaaacgtccgcaatgtgttattaagttgtctaagcgtcaatttgtttacaccacaatatatcctgccaccagccagccaacagctcc |
| ccgaccggcagctcggcacaaaatcaccactcgatacaggcagcccatcag |

-continued

ANNEX

SEQ ID NO: 5:
Plasmid backbone insertion containing virG gene of pNMD062
ctgtcgatcagatctggctcgcggcggacgcacgacgccggggcgagaccataggcgatctcctaaatcaatagtagctgtaacctcgaagcgtt
tcacttgtaacaacgattgagaatttttgtcataaaattgaaatacttggttcgcatttttgtcatccgcggtcagccgcaattctgacgaactgcccattta
gctggagatgattgtacatccttcacgtgaaaatttctcaagcgctgtgaacaagggttcagattttagattgaaaggtgagccgttgaaacacgttctt
cttgtcgatgacgacgtcgctatgcggcatcttattattgaataccttacgatccacgccttcaaagtgaccgcggtagccgacagcacccagttcac
aagagtactctcttccgcgacggtcgatgtcgtggttgttgatctaaatttaggtcgtgaagatgggctcgagatcgttcgtaatctggcggcaaagtct
gatattccaatcataattatcagtggcgaccgccttgaggagacggataaagttgttgcactcgagctaggagcaagtgattttatcgctaagccgttc
agtatcagagagtttctagcacgcattcgggttgccttgcgcgtgcgccccaacgttgtccgctccaaagaccgacggtctttttgttttactgactgga
cacttaatctcaggcaacgtcgcttgatgtccgaagctggcggtgaggtgaaacttacggcaggtgagttcaatcttctcctcgcgtttttagagaaac
cccgcgacgttctatcgcgcgagcaacttctcattgccagtcgagtacgcgacgaggaggtttatgacaggagtatagatgttctcattttgaggctg
cgccgcaaacttgaggcggatccgtcaagccctcaactgataaaaacagcaagaggtgccggttatttctttgacgcggacgtgcaggtttcgcac
ggggggacgatggcagcctaagatcgacag SEQ ID NO: 6:
Plasmid backbone insertion containing virG gene of pNMD063, pNMD2190
ctgtcgatcagatctggctcgcggcggacgcacgacgccggggcgagaccataggcgatctcctaaatcaatagtagctgtaacctcgaagcgtt
tcacttgtaacaacgattgagaatttttgtcataaaattgaaatacttggttcgcatttttgtcatccgcggtcagccgcaattctgacgaactgcccattta
gctggagatgattgtacatccttcacgtgaaaatttctcaagtgctgtgaacaagggttcagattttagattgaaaggtgagccgttgaaacacgttctt
cttgtcgatgacgacgtcgctatgcggcatcttattattgaataccttacgatccacgccttcaaagtgaccgcggtagccgacagcacccagttcac
aagagtactctcttccgcgacggtcgatgtcgtggttgttgatctagatttaggtcgtgaagatgggctcgagatcgttcgtaatctggcggcaaagtct
gatattccaatcataattatcagtggcgaccgccttgaggagacggataaagttgttgcactcgagctaggagcaagtgattttatcgctaagccgttc
agtatcagagagtttctagcacgcattcgggttgccttgcgcgtgcgccccaacgttgtccgctccaaagaccgacggtctttttgttttactgactgga
cacttaatctcaggcaacgtcgcttgatgtccgaagctggcggtgaggtgaaacttacggcaggtgagttcaatcttctcctcgcgtttttagagaaac
cccgcgacgttctatcgcgcgagcaacttctcattgccagtcgagtacgcgacgaggaggtttatgacaggagtatagatgttctcattttgaggctg
cgccgcaaacttgaggcggatccgtcaagccctcaactgataaaaacagcaagaggtgccggttatttctttgacgcggacgtgcaggtttcgcac
ggggggacgatggcagcctaagatcgacag SEQ ID NO: 7:
full-length nucleotide sequence of pNMD1971
ttaagattgaatcctgttgccggtcttgcgatgattatcatataatttctgttgaattacgttaagcatgtaataattaacatgtaatgcatgacgttatttatga
gatgggtttttatgattagagtcccgcaattatacatttaatacgcgatagaaaacaaaatatagcgcgcaaactaggataaattatcgcgcgcggtg
tcatctatgttactagatcgacctgcaggcatgccaattccaatcccacaaaaatctgagcttaacagcacagttgctcctctcagagcagaatcgg
gtattcaacaccctcatatcaactactacgttgtgtataacggtccacatgccggtatatacgatgactggggttgtacaaaggcggcaacaaacgg
cgttcccggagttgcacacaagaaatttgccactattacagaggcaagagcagcagctgacgcgtacacaacaagtcagcaaacagacaggtt
gaacttcatccccaaaggagaagctcaactcaagcccaagagctttgctaaggccctaacaagcccaccaaagcaaaaagcccactggctca
cgctaggaaccaaaaggcccagcagtgatccagccccaaaagagatctcctttgccccggagattacaatggacgatttcctctatctttacgatct
aggaaggaagttcgaaggtgaaggtgacgacactatgttcaccactgataatgagaaggttagcctcttcaatttcagaaagaatgctgacccac
agatggttagagaggcctacgcagcaggtctcatcaagacgatctacccgagtaacaatctccaggagatcaaataccttcccaagaaggttaa
agatgcagtcaaaagattcaggactaattgcatcaagaacacagagaaagacatatttctcaagatcagaagtactattccagtatggacgattca
aggcttgcttcataaaccaaggcaagtaatagagattggagtctctaaaaaggtagttcctactgaatctaaggccatgcatggagtctaagattca
aatcgaggatctaacagaactcgccgtgaagactggcgaacagttcatacagagtcttttacgactcaatgacaagaagaaaatcttcgtcaacat
ggtggagcacgacactctggtctactccaaaaatgtcaaagatacagtctcagaagaccaaagggctattgagacttttcaacaaaggataatttc
gggaaacctcctcggattccattgcccagctatctgtcacttcatcgaaaggacagtagaaaaggaaggtggctcctacaaatgccatcattgcgat
aaaggaaaggctatcattcaagatctctctgccgacagtggtcccaaagatggacccccacccacgaggagcatcgtggaaaaagaagacgtt
ccaaccacgtcttcaaagcaagtggattgatgtgacatctccactgacgtaagggatgacgcacaatcccactatccttcgcaagacccttcctctat
ataaggaagttcatttcatttggagaggacacgctcgagtataagagctctatttttacaacaattaccaacaacaacaaacaacaaacaacattac
aattacatttacaattaccatggaacgagctatacaaggaaacgatgctagggaacaagcttatggtgaacgttggaatggaggatcaggaagttc
cacttctcccttcaaacttcctgacgaaagtccgagttggactgagtggcggctacataacgatgagacgatttcgaatcaagataatccccttggttt
caaggaaagctggggtttcgggaaagttgtatttaagagatatctcagatacgacgggacggaaacttcactgcacagagtccttggatcttggac
gggagattcggttaactatgcagcatctcgatttctcggtttcgaccagatcggatgtacctatagtattcggtttcgaggagttagtgtcaccatttctgg -continued

| ANNEX |
| --- |
| agggtcgcgaactcttcagcatctcagtgaaatggcaattcggtctaagcaagaactgctacagcttaccccagtcaaagtggaaagtgatgtatc |
| aagaggatgccctgaaggtgttgaaaccttcgaagaagaaagcgagtaaggatcctctagagtcctgctttaatgagatatgcgagacgcctatg |
| atcgcatgatatttgctttcaattctgttgtgcacgttgtaaaaaacctgagcatgtgtagctcagatccttaccgccggtttcggttcattctaatgaatata |
| tcacccgttactatcgtatttttatgaataatattctccgttcaatttactgattgtaccctactacttatatgtacaatattaaaatgaaaacaatatattgtgct |
| gaataggtttatagcgacatctatgatagagcgccacaataacaaacaattgcgttttattattacaaatccaattttaaaaaaagcggcagaaccg |
| gtcaaacctaaaagactgattacataaatcttattcaaatttcaaaagtgccccaggggctagtatctacgacacaccgagcggcgaactaataac |
| gctcactgaagggaactccggttccccgccggcgcgcatgggtgagattccttgaagttgagtattggccgtccgctctaccgaaagttacgggca |
| ccattcaacccggtccagcacggcggccgggtaaccgacttgctgccccgagaattatgcagcatttttttggtgtatgtgggccccaaatgaagtg |
| caggtcaaaccttgacagtgacgacaaatcgttgggcgggtccagggcgaattttgcgacaacatgtcgaggctcagcaggacctgcataagct |
| cttctgtcagcgggcccactgcatccaccccagtacattaaaaacgtccgcaatgtgttattaagttgtctaagcgtcaatttgtttacaccacaatatat |
| cctgccaccagccagccaacagctccccgaccggcagctcggcacaaaatcaccactcgatacaggcagcccatcagtcagatcaggatctc |
| ctttgcgacgctcaccgggctggttgccctcgccgctgggctggcggccgtctatggccctgcaaacgcgccagaaacgccgtcgaagccgtgtg |
| cgagacaccgcggccgccggcgttgtggatacctcgcggaaaacttggccctcactgacagatgaggggcggacgttgacacttgaggggccg |
| actcacccggcgcggcgttgacagatgaggggcaggctcgatttcggccggcgacgtggagctggccagcctcgcaaatcggcgaaaacgcc |
| tgattttacgcgagtttcccacagatgatgtggacaagcctggggataagtgccctgcggtattgacacttgaggggcgcgactactgacagatgag |
| gggcgcgatccttgacacttgaggggcagagtgctgacagatgaggggcgcacctattgacatttgaggggctgtccacaggcagaaaatccag |
| catttgcaagggtttccgcccgtttttcggccaccgctaacctgtcttttaacctgcttttaaaccaatatttataaaccttgtttttaaccagggctgcgccct |
| gtgcgcgtgaccgcgcacgccgaaggggggtgcccccccttctcgaaccctcccggcccgctaacgcgggcctcccatccccccaggggctgc |
| gcccctcggccgcgaacggcctcaccccaaaaatggcagcgctggccaattcgtgcgcggaacccctatttgtttatttttctaaatacattcaaatat |
| gtatccgctcatgagacaataaccctgataaatgcttcaataatattgaaaaaggaagagtatggctaaaatgagaatatcaccggaattgaaaaa |
| actgatcgaaaaataccgctgcgtaaaagatacggaaggaatgtctcctgctaaggtatataagctggtgggagaaaatgaaaacctatatttaaa |
| aatgacggacagccggtataaagggaccacctatgatgtggaacgggaaaaggacatgatgctatggctggaaggaaagctgcctgttccaaa |
| ggtcctgcactttgaacggcatgatggctggagcaatctgctcatgagtgaggccgatggcgtcctttgctcggaaggtatgaagatgaacaaag |
| ccctgaaaagattatcgagctgtatgcggagtgcatcaggctctttcactccatcgacatatcggattgtccctatacgaatagcttagacagccgctt |
| agccgaattggattacttactgaataacgatctggccgatgtggattgcgaaaactgggaagaagacactccatttaaagatccgcgcgagctgtat |
| gatttttaaagacggaaaagcccgaagaggaacttgtcttttcccacggcgacctgggagacagcaacatctttgtgaaagatggcaaagtaagt |
| ggctttattgatcttgggagaagcggcagggcggacaagtggtatgacattgccttctgcgtccggtcgatcagggaggatatcggggaagaaca |
| gtatgtcgagctatttttgacttactggggatcaagcctgattgggagaaaataaaatattatattttactggatgaattgttttagctgtcagaccaagttt |
| actcatatatactttagattgatttaaaacttcatttttaatttaaaaggatctaggtgaagatcctttttgataatctcatgaccaaaatcccttaacgtgagt |
| tttcgttccactgagcgtcagaccccgtagaaaagatcaaaggatcttcttgagatcctttttttctgcgcgtaatctgctgcttgcaaacaaaaaaacc |
| accgctaccagcggtggtttgtttgccggatcaagagctaccaactctttttccgaaggtaactggcttcagcagagcgcagataccaaatactgtcc |
| ttctagtgtagccgtagttaggccaccacttcaagaactctgtagcaccgcctacatacctcgctctgctaatcctgttaccagtggctgctgccagtgg |
| cgataagtcgtgtcttaccgggttggactcaagacgatagttaccggataaggcgcagcggtcgggctgaacggggggttcgtgcacacagccc |
| agcttggagcgaacgacctacaccgaactgagatacctacagcgtgagctatgagaaagcgccacgcttcccgaagggagaaaggcggaca |
| ggtatccggtaagcggcagggtcggaacaggagagcgcacgagggagcttccagggggaaacgcctggtatctttatagtcctgtcgggtttcgc |
| cacctctgacttgagcgtcgatttttgtgatgctcgtcaggggggcggagcctatggaaaaacgccagcaacgcggcctttttacggttcctggcaga |
| tcctagatgtggcgcaacgatgccggcgacaagcaggagcgcaccgacttcttccgcatcaagtgttttggctctcaggccgaggcccacggcaa |
| gtatttgggcaaggggtcgctggtattcgtgcagggcaagattcggaataccaagtacgagaaggacggccagacggtctacggaccgacttc |
| attgccgataaggtggattatctggacaccaaggcaccaggcgggtcaaatcaggaataagggcacattgccccggcgtgagtcggggcaatc |
| ccgcaaggagggtgaatgaatcggacgtttgaccggaaggcatacaggcaagaactgatcgacgcggggttttccgccgaggatgccgaaac |
| catcgcaagccgcaccgtcatgcgtgcgccccgcgaaaccttccagtccgtcggctcgatggtccagcaagctacggccaagatcgagcgcga |
| cagcgtgcaactggctccccctgccctgcccgcgccatcggccgccgtggagcgttcgcgtcgtctcgaacaggaggcggcaggtttggcgaag |
| tcgatgaccatcgacacgcgaggaactatgacgaccaagaagcgaaaaaccgccggcgaggacctggcaaaacaggtcagcgaggccaa |
| gcaggccgcgttgctgaaacacacgaagcagcagatcaaggaaatgcagctttccttgttcgatattgcgccgtggccggacacgatgcgagcg |
| atgccaaacgacacggcccgctctgcccgctctgccctgttcaccacgcgcaacaagaaaatcccgcgcgaggcgctgcaaaacaaggtcattttccacgtc |
| aacaaggacgtgaagatcacctacaccggcgtcgagctgcgggccgacgatgacgaactggtgtggcagcaggtgttggagtacgcgaagcg |
| caccccctatcggcgagccgatcaccttcacgttctacgagctttgccaggacctgggctggtcgatcaatggccggtattacacgaaggccgagga |
| atgcctgtcgcgcctacaggcgacggcgatgggcttcacgtccgaccgcgttgggcacctggaatcggtgtcgctgctgcaccgcttccgcgtcct |
| ggaccgtggcaagaaaacgtcccgttgccaggtcctgatcgacgaggaaatcgtcgtgctgtttgctggcgaccactacacgaaattcatatggg |
| agaagtaccgcaagctgtcgccgacggcccgacggatgttcgactatttcagctcgcaccgggagccgtacccgctcaagctggaaaccttccg |
| cctcatgtgcggatcggattccacccgcgtgaagaagtggcgcgagcaggtcggcgaagcctgcgaagagttgcgaggcagcggcctggtgg |

-continued

| ANNEX |
| --- |
| aacacgcctgggtcaatgatgacctggtgcattgcaaacgctagggccttgtggggtcagttccggctgggggttcagcagccagcgcctgatctg |
| gggaaccctgtggttggcacatacaaatggacgaacggataaaccttttcacgcccttttaaatatccgattattctaataaacgctcttttctcttaggtt |
| tacccgccaatatatcctgtcaaacactgatagtttaaactgaaggcgggaaacgacaatctgatctaagctaggcatggaattccaatcccacaa |
| aaatctgagcttaacagcacagttgctcctctcagagcagaatcgggtattcaacaccctcatatcaactactacgttgtgtataacggtccacatgc |
| cggtatatacgatgactggggttgtacaaaggcggcaacaaacggcgttcccggagttgcacacaagaaatttgccactattacagaggcaaga |
| gcagcagctgacgcgtacacaacaagtcagcaaacagacaggttgaacttcatccccaaaggagaagctcaactcaagcccaagagctttgct |
| aaggccctaacaagcccaccaaagcaaaaagcccactggctcacgctaggaaccaaaaggcccagcagtgatccagccccaaaagagatc |
| tcctttgccccggagattacaatggacgatttcctctatctttacgatctaggaaggaagttcgaaggtgaaggtgacgacactatgttcaccactgat |
| aatgagaaggttagcctcttcaatttcagaaagaatgctgacccacagatggttagagaggcctacgcagcaggtctcatcaagacgatctaccc |
| gagtaacaatctccaggagatcaaataccttcccaagaaggttaaagatgcagtcaaaagattcaggactaattgcatcaagaacacagagaa |
| agacatatttctcaagatcagaagtactattccagtatggacgattcaaggcttgcttcataaaccaaggcaagtaatagagattggagtctctaaaa |
| aggtagttcctactgaatctaaggccatgcatggagtctaagattcaaatcgaggatctaacagaactcgccgtgaagactggcgaacagttcata |
| cagagtcttttacgactcaatgacaagaagaaaatcttcgtcaacatggtggagcacgacactctggtctactccaaaaatgtcaaagatacagtct |
| cagaagaccaaagggctattgagacttttcaacaaaggataatttcgggaaacctcctcggattccattgcccagctatctgtcacttcatcgaaag |
| gacagtagaaaaggaaggtggctcctacaaatgccatcattgcgataaaggaaaggctatcattcaagatctctctgccgacagtggtcccaaag |
| atggacccccacccacgaggagcatcgtggaaaaagaagacgttccaaccacgtcttcaaagcaagtggattgatgtgacatctccactgacgt |
| aagggatgacgcacaatcccactatccttcgcaagacccttcctctatataaggaagttcatttcatttggagaggacacgctcgagtataagagctc |
| atttttacaacaattaccaacaacaacaaacaacaaacaacattacaattacatttacaattatcgatgggtcagtcccttatgttacgtcctgtagaa |
| accccaacccgtgaaatcaaaaaactcgacggcctgtgggcattcagtctggatcgcgaaaactgtggaattgatcagcgttggtgggaaagcg |
| cgttacaagaaagccgggcaattgctgtgccaggcagttttaacgatcagttcgccgatgcagatattcgtaattatgcgggcaacgtctggtatcag |
| cgcgaagtctttataccgaaaggtaagtagtgtttttggataactgagtttgcctatgattttgtatttactgagatgtttgtcctctttgtgcaggttgggcag |
| gccagcgtatcgtgctgcgtttcgatgcggtcactcattacggcaaagtgtgggtcaataatcaggaagtgatggagcatcagggcggctatacgc |
| catttgaagccgatgtcacgccgtatgttattgccgggaaaagtgtacgtatcaccgtttgtgtgaacaacgaactgaactggcagactatcccgcc |
| gggaatggtgattaccgacgaaaacggcaagaaaaagcagtcttacttccatgatttctttaactatgccggaatccatcgcagcgtaatgctctac |
| accacgccgaacacctgggtggacgatatcaccgtggtgacgcatgtcgcgcaagactgtaaccacgcgtctgttgactggcaggtggtggcca |
| atggtgatgtcagcgttgaactgcgtgatgcggatcaacaggtggttgcaactggacaaggcactagcgggactttgcaagtggtgaatccgcacc |
| tctggcaaccgggtgaaggttatctctatgaactgtgcgtcacagccaaaagccagacagagtgtgatatctacccgcttcgcgtcggcatccggtc |
| agtggcagtgaagggccaacagttcctgattaaccacaaaccgttctactttactggctttggtcgtcatgaagatgcggacttacgtggcaaaggat |
| tcgataacgtgctgatggtgcacgaccacgcattaatggactggattggggccaactcctaccgtacctcgcattacccttacgctgaagagatgct |
| cgactgggcagatgaacatggcatcgtggtgattgatgaaactgctgctgtcggctttaacctctctttaggcattggtttcgaagcgggcaacaagc |
| cgaaagaactgtacagcgaagaggcagtcaacggggaaactcagcaagcgcacttacaggcgattaaagagctgatagcgcgtgacaaaaa |
| ccacccaagcgtggtgatgtggagtattgccaacgaaccggatacccgtccgcaaggtgcacgggaatatttcgcgccactggcggaagcaac |
| gcgtaaactcgacccgacgcgtccgatcacctgcgtcaatgtaatgttctgcgacgctcacaccgataccatcagcgatctctttgatgtgctgtgcct |
| gaaccgttattacggatggtatgtccaaagcggcgatttggaaacggcagagaaggtactggaaaaagaacttctggcctggcaggagaaactg |
| catcagccgattatcatcaccgaatacggcgtggatacgttagccgggctgcactcaatgtacaccgacatgtggagtgaagagtatcagtgtgca |
| tggctggatatgtatcaccgcgtctttgatcgcgtcagcgccgtcgtcggtgaacaggtatggaatttcgccgattttgcgacctcgcaaggcatattgc |
| gcgttggcggtaacaagaaagggatcttcactcgcgaccgcaaaccgaagtcggcggcttttctgctgcaaaaacgctggactggcatgaacttc |
| ggtgaaaaaccgcagcagggaggcaaacaatgaatcaacaactctcctggcgcaccatcgtcggctacagcctcgggaattgggatcctctag |
| agtcaagcagatcgttcaaacatttggcaataaagtttc |

The invention claimed is:

1. A process of transiently transfecting a *Nicotiana* plant or leaves on said plant, comprising contacting said plant or said leaves with a suspension comprising *Agrobacterium* cells of strain CryX having accession no. DSM25686, wherein the transient transfection efficiency obtainable with strain CryX is higher than with strain KYRT1 when infiltrating *Nicotiana benthamiana* leaves using needleless syringe with dilutions of agrobacterial cultures of both strains harboring a green fluorescent protein (GFP) expression tobacco mosaic virus (TMV)-based vector and comparing the intensity of GFP fluorescence.

2. A process of transiently expressing a DNA sequence of interest in a *Nicotiana* plant, comprising contacting said plant or leaves on said plant with a suspension comprising *Agrobacterium* cells of strain CryX having accession no. DSM25686, wherein the transient transfection efficiency obtainable with strain CryX is higher than with strain KYRT1 when infiltrating *Nicotiana benthamiana* leaves using needleless syringe with dilutions of agrobacterial cultures of both strains harboring a GFP expression TMV-based vector and comparing the intensity of GFP fluorescence.

3. The process according to claim 1, wherein said strain CryX contains a binary vector having T-DNA comprising a DNA sequence of interest to be transfected into cells of said plant or leaves.

4. The process according to claim 3, wherein said binary vector comprises a virG gene expressible in said strain CryX.

5. The process according to claim 4, wherein said virG gene encodes a VirG protein from *Agrobacterium tumefaciens* strain LBA4404 of SEQ ID NO: 1, or is an N54D mutant of the VirG protein encoded by the virG gene from *A. tumefaciens* strain LBA4404.

6. The process according to claim 1, wherein said *Nicotiana* plant or leaves on said plant are contacted with said suspension by spraying or by vacuum infiltrating said plant or leaves on said plant with said suspension.

7. The process according to claim 1, wherein said *Nicotiana* plant is a *Nicotiana benthamiana*.

* * * * *